US009752136B2

(12) United States Patent
Mayer et al.

(10) Patent No.: US 9,752,136 B2
(45) Date of Patent: Sep. 5, 2017

(54) POLYPEPTIDES HAVING ENDOLYSIN ACTIVITY AND USES THEREOF

(71) Applicant: PLANT BIOSCIENCE LIMITED, Norwich (GB)

(72) Inventors: Melinda Mayer, Wreningham Norfolk (GB); Arjan Narbad, Norwich Norfolk (GB)

(73) Assignee: PLANT BIOSCIENCE LIMITED, Norwich (GB)

( * ) Notice: Subject to any disclaimer, the term of this patent is extended or adjusted under 35 U.S.C. 154(b) by 0 days.

(21) Appl. No.: 14/818,927

(22) Filed: Aug. 5, 2015

(65) Prior Publication Data
US 2016/0017307 A1 Jan. 21, 2016

Related U.S. Application Data

(63) Continuation-in-part of application No. PCT/GB2014/050275, filed on Jan. 31, 2014.

(30) Foreign Application Priority Data

Feb. 5, 2013 (GB) .................................. 1302042.5

(51) Int. Cl.

| C12N 9/24 | (2006.01) |
| C12N 1/21 | (2006.01) |
| C12N 9/36 | (2006.01) |
| C12N 9/80 | (2006.01) |
| A23K 50/00 | (2016.01) |
| A23K 50/75 | (2016.01) |
| A23K 50/30 | (2016.01) |
| A23K 50/40 | (2016.01) |
| A23K 50/80 | (2016.01) |
| A61K 38/00 | (2006.01) |

(52) U.S. Cl.
CPC ............ *C12N 9/2462* (2013.01); *A23K 50/00* (2016.05); *A23K 50/30* (2016.05); *A23K 50/40* (2016.05); *A23K 50/75* (2016.05); *A23K 50/80* (2016.05); *C12N 9/80* (2013.01); *C12Y 305/01028* (2013.01); *A61K 38/00* (2013.01); *C12Y 302/01017* (2013.01)

(58) Field of Classification Search
None
See application file for complete search history.

(56) References Cited

U.S. PATENT DOCUMENTS

| 7,371,375 B2 | 5/2008 | Zimmer et al. |
| 8,962,297 B2 | 2/2015 | Seal et al. |
| 2005/0153415 A1 | 7/2005 | Zimmer et al. |
| 2012/0052546 A1* | 3/2012 | Seal .................. C12N 9/80 435/183 |
| 2012/0134972 A1* | 5/2012 | Mayer .................. C12N 1/06 424/93.21 |
| 2016/0040148 A1 | 2/2016 | Mayer et al. |

FOREIGN PATENT DOCUMENTS

| WO | 03/066845 | 8/2003 |
| WO | 2010/003943 | 1/2010 |
| WO | 2010/136754 | 12/2010 |
| WO | 2012/030535 | 3/2012 |

OTHER PUBLICATIONS

Gervasi et al., Arch. Virol. 158:2015-2017, Apr. 2013.*
Zimmer et al., Appl. Environ. Microbiol. 68:5311-5317, 2002.*
Gervasi et al., Appl. Microbiol. Biotechnol. 98:2495-2505, Aug. 2013.*
GenBank Accession No. KC237729, Apr. 2013, 17 pages.*
Sang, H., Mechanisms of Development 121:1179-1186, 2004.*
International Search Report dated Jun. 2, 2014, which issued during prosecution of International Application No. PCT/GB2014/050275.
Database UniProt "Subname: Full=Putative N-acetylmuramoyl-L-alanine amidase" retrieved from EBI Accession No. UNIPROT: H7CV24, May 16, 2012.
Gervasi, et al. "Expression and delivery of an endolysin to combat Clostridium perfringens" Applied Microbiology and Biotechnology, Aug. 2013, 98(6):2495-2505.
Nariya, et al. "Identification and characterization of a putative endolysin encoded by episomal phage phiSM101 of Clostridium perfringens" Applied Microbiology and Biotechnology, Apr. 2011, 90(6):1973-1979.
Nowell, et al. "Genome Sequencing and Analysis of a Type A Clostridium perfringens Isolate from a Case of Bovine Clostridial Abomasitis" PLOS One, Mar. 2012, 7(3):e32271.
Schmitz, et al. "Lytic enzyme discovery through multigenomic sequence analysis in Clostridium perfringens" Applied Microbiology and Biotechnology, Mar. 2011, 89(6):1783-1795.
Simm

(56) References Cited

OTHER PUBLICATIONS

Annex B: Comparison between Seq Id No. 1 (i.e. CP51L) and D2 (i.e. plyS9) Apr. 20, 2017.
Annex C: Comparison between Seq Id No. 1 (i.e. CP51L) and plyCP39O of D3 and D4, Apr. 20, 2017.
Annex D: Comparison between Seq Id No. 1 (i.e. CP51L) and plyCP26F of D3 and D4, Apr. 20, 2017.
Annex E: Comparison between Seq Id No. 1 (i.e. CP51L) and D6 (i.e. plyCM), Apr. 20, 2017.

* cited by examiner

| | | |
|---|---|---|
| CP51L | ----------------------------YINQSN KFNGLRY DPNK I A AT CSV D W | 40 |
| EIA17471 | ----------------------------YINQSN KFNGLNY NPNK I NA HPNCSV D W | 40 |
| ZP_02633232 | --------------------------MN TDL NYRNGRN S DY C FTGNQN KAS NANY | 42 |
| ZP_02640305 | --------------------------MK N RL TNVT--LNA NPKH I ET NT KGAGAETHC | 40 |
| ZP_02636955 | ------MKIAVRGGHNFQAKGASALIDETIED VKD ILNLRKE HE LD TPG C VN LR A | 65 |
| ZP_02630819 | MSKNIKKIAVRGGHNFQATGAVALIGETSED VKD IVYLRQE YQ LD TPG C QI LR KA | 70 |
| ZP_02953092 | ------MKIAVRGGHNFQATGAAALIGETSED VKD IECLRQE HQ LD TPG C QI LR A | 65 |

| | | |
|---|---|---|
| CP51L | HKGNG--WSG GYD RKEGS---------- - RPENAI AHT GQNSSSI C AFMRE PTRA | 98 |
| EIA17471 | HKGNG--WSG GY RK GS---------- - RPENAK AHT GQNSSSI C ALMRE PTRA | 98 |
| ZP_02633232 | FRCVN---RQA A DD EIVQV RE DTS HC DGNGR ITNS ------G MCA GD S K | 103 |
| ZP_02640305 | KAQANGNIGKA DDTGVYQ EHKHAT NC DGNNR INNK ------S I CVNSDSD NK | 104 |
| ZP_02636955 | EEWGA--DLF DKAY SYNG GT TW CGA GQAEV ARRI IANGT RNF VK P L | 133 |
| ZP_02630819 | EEWGA--DLF DKAY SYNG GT TW G KAEV ARRI IASGT KNF VK S L | 138 |
| ZP_02953092 | EEWGA--DLF DKAY SYNG GT TW G KAEV ARRI IANGT KNF VK S L | 133 |

| | | |
|---|---|---|
| CP51L | N YE AD RARR---GNLP YG FNN--------T CPGINFPLE FKN SYRPTGG-EI D | 157 |
| EIA17471 | N YY AD RARR---GNLP YG FNN--------T CPGANFPLE FKN SYRPTGGTEI D | 158 |
| ZP_02633232 | T ENTLW KS MNKYGIDIDH VR Y ASR CCPSPFSP NWSR WWEE RLKGTVEN-IEVT T | 172 |
| ZP_02640305 | A DNTVE RY KNGY-YSNC VR Y ASR NCPRR A --GYWNTFL RVNSKDSSSQTPANT YK | 171 |
| ZP_02636955 | RKT PA IE CFCE--ATTD SIY AKGSN----- GELIAEGICN DIKT NIPSQT-QS L | 195 |
| ZP_02630819 | RNT PA VE CFCE--ATTD AIY AKGP ----- GELIAEGICN DIHT NTPSLTPQD LI | 201 |
| ZP_02953092 | RNT PA VE CFCE--ATTD AIY SKGP ----- GELIAEGICN DISS NTTNQTEQP LE | 196 |

| | | |
|---|---|---|
| CP51L | R DE KV E S AS GNE S | 227 |
| EIA17471 | I N E KGNV QG HS RNH GK K S | 228 |
| ZP_02633232 | DIE DK VK S RN GK K | 242 |
| ZP_02640305 | S RE NH SG R G G | 241 |
| ZP_02636955 | A S P PN L GSE M | 265 |
| ZP_02630819 | P L ASG M | 271 |
| ZP_02953092 | P L SG M | 266 |

FIG. 3

```
CP51L        ...                                              297
EIA17471     ...                                              298
ZP_02633232  ...                                              312
ZP_02640305  ...                                              311
ZP_02636955  ...                                              335
ZP_02630819  ...                                              341
ZP_02953092  ...                                              336

CP51L        ...AV...EEE.I.EGI..VNTY.NVRDSI.GNI...K.FNG.E.S..WTKD......D..NH....  367
EIA17471     ......--..GEVVN..TSL..RAGAGT.YSA......EP...D..GKAE........KNE....   366
ZP_02633232  ...SV...EEG.I.DGI..VNTY.NVRDSICGNI...K.FNG.E.S..WTKD......D..NH....  382
ZP_02640305  ...S.NK..EN--IQYGI..VNS..NVRENP.GEV....YK...Q..KEEN..C....S..SK..F.   379
ZP_02636955  ...K.K.....--IC----------------------------------------------------- 349
ZP_02630819  ...E.T....--.GEVVN..TSL..RKGPGT.YSN......EP...D..EMIGE......NK....   409
ZP_02953092  ...K.E....--.G.VVN..TSL..RKGPGT.YSN......EP...D..EKVE........ARNE... 404

CP51L        ..S...E.- 377
EIA17471     ..E...I.Q 377
ZP_02633232  ..S...E.- 392
ZP_02640305  ..S...L.- 389
ZP_02636955  ----------
ZP_02630819  ..A...KE.- 419
ZP_02953092  ..E...I.Q 415
```

FIG. 3 (continued)

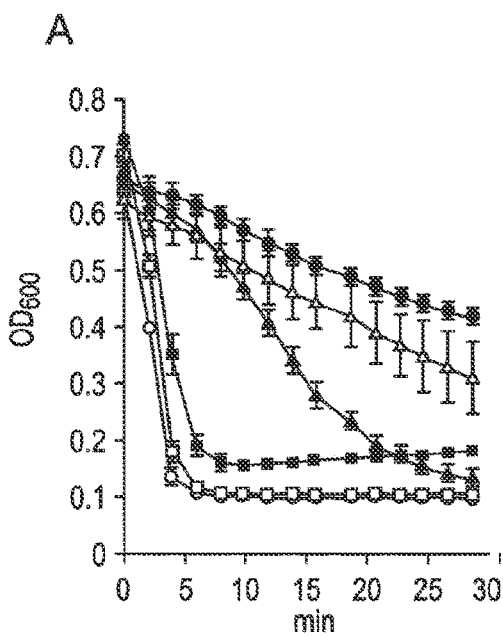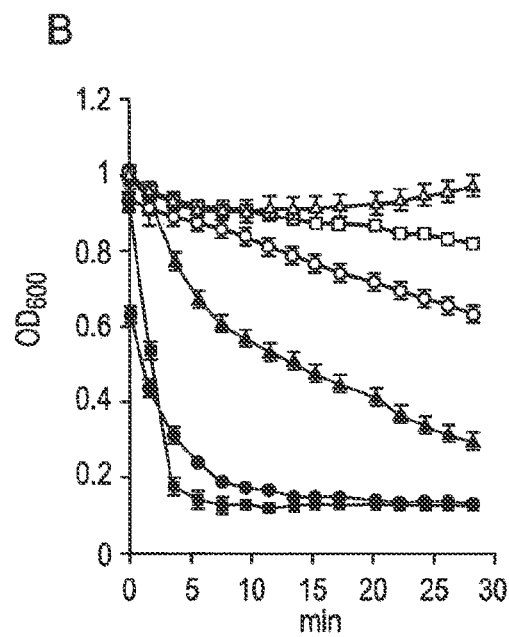
FIG. 5A
FIG. 5B

FIG. 8A
FIG. 8B
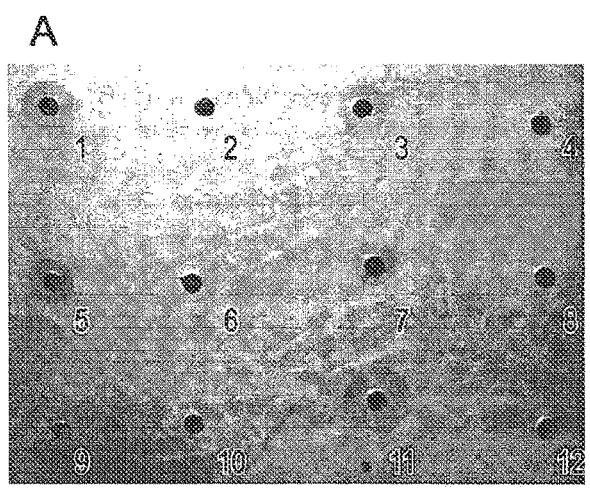
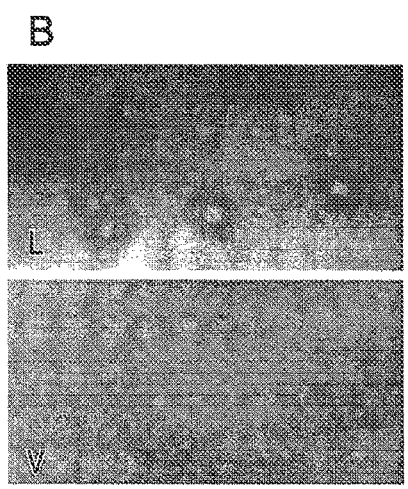

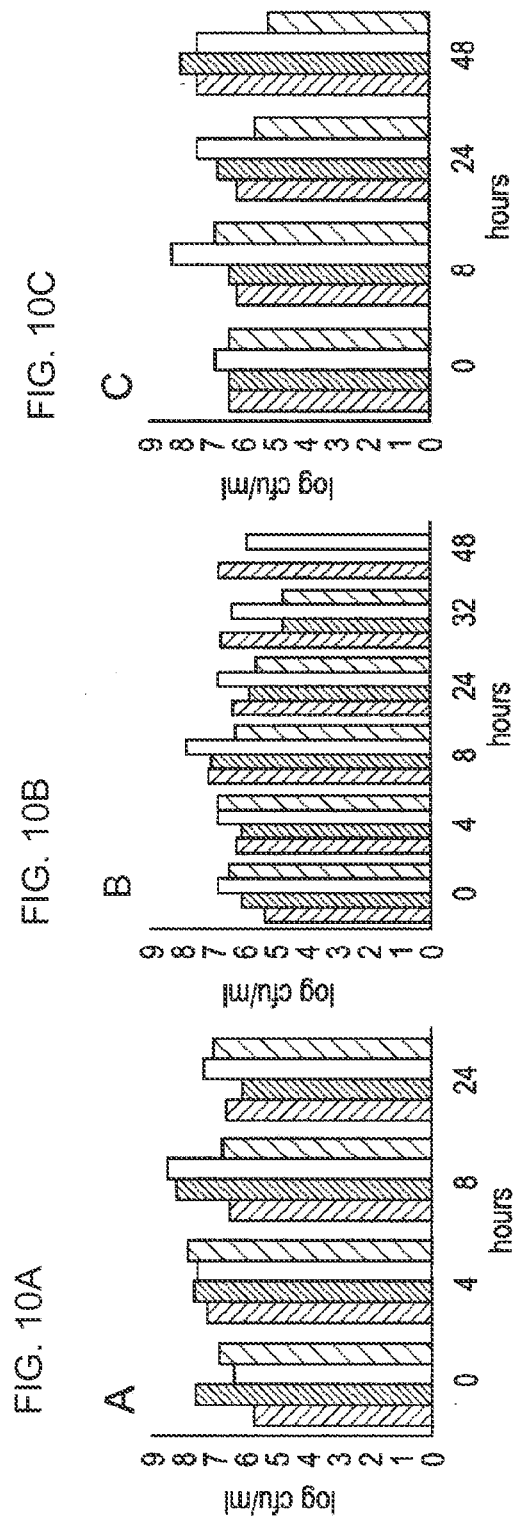

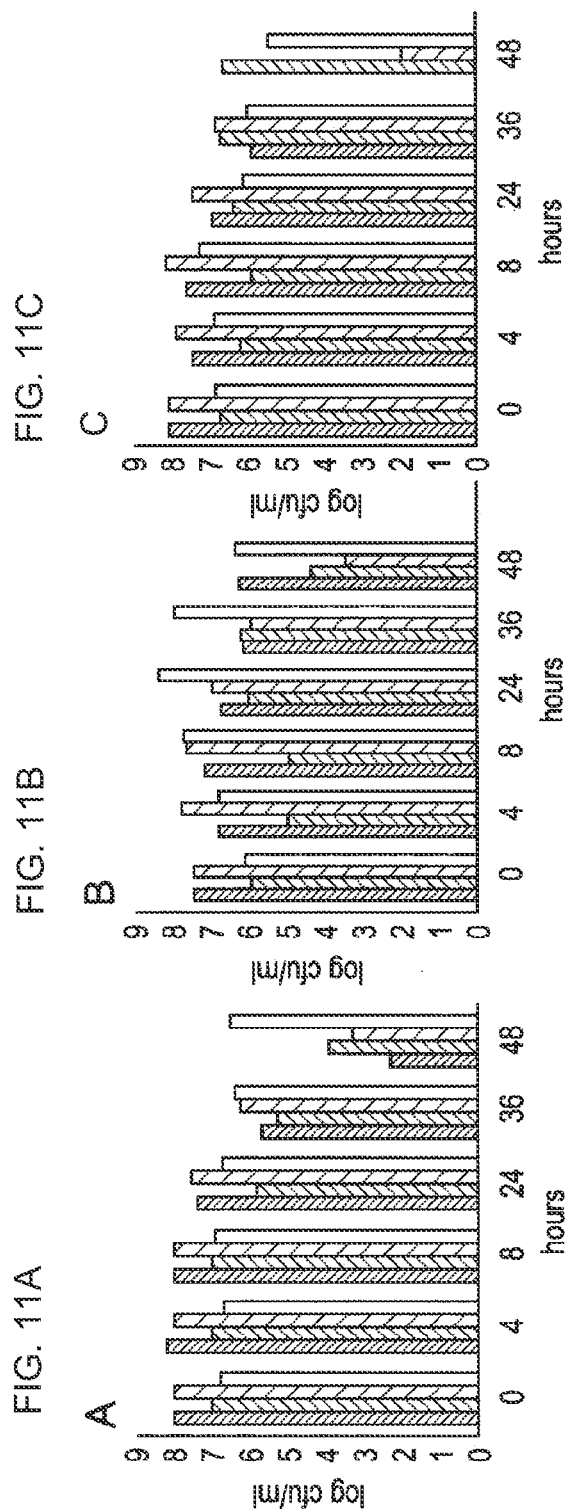

ered death in the UK and USA.

POLYPEPTIDES HAVING ENDOLYSIN ACTIVITY AND USES THEREOF

RELATED APPLICATIONS AND INCORPORATION BY REFERENCE

This application is a continuation-in-part application of international patent application Serial No. PCT/GB2014/050275 filed 31 Jan. 2014, which published as PCT Publication No. WO 2014/122435 A1 on 14 Aug. 2014, which claims benefit of GB patent application Serial No. 1302042.5 filed 5 Feb. 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Oct. 2, 2015, is named 44445002006_SL.txt and is 28,051 bytes in size.

FIELD OF INVENTION

The present invention relates to novel polypeptides derived from endolysins from a bacteriophage of *Clostridium perfringens* and to nucleic acid molecules encoding the same, as well as to compositions thereof. The invention also provides uses of such polypeptides and nucleic acid molecules in the diagnosis and treatment of conditions and diseases associated with microbial cells such as *Clostridium perfringens*. In particular, the invention provides a polypeptide having endolysin activity derived from bacteriophage ϕCP51 of *Clostridium perfringens* and to uses thereof.

BACKGROUND OF THE INVENTION

*Clostridium perfringens*, one of the most pathogenic species in the *Clostridium* genus, is a cause for increasing concern due to its responsibility for severe infections both in humans and animals, especially poultry. *C. perfringens* is a rod-shaped, Gram-positive, anaerobic spore-forming bacterium with the ability to produce potent toxins. According to the pattern of toxin expression, *C. perfringens* strains are classified into five toxinotypes: A, B, C, D and E. The interest in this microorganism is increasing because it is responsible for food poisoning, gas gangrene, necrotic enteritis (NE) both in humans and animals, and non-food borne gastrointestinal infections. In fact, *C. perfringens* is considered the third leading cause of human food poisoning-related death in the UK and USA.

A range of different alternatives to the conventional antimicrobial growth promoter approach are being investigated to reduce the numbers of *C. perfringens* pathogens in the food chain and to improve poultry health. In addition to vaccination and the use of natural antimicrobials, there are a number of examples of using probiotic microbes or lytic enzymes to control NE in poultry.

Despite such control strategies, *C. perfringens*-associated food poisoning is classed among the most common gastrointestinal diseases in industrialized countries. One of the most frequently occurring infections caused by *C. perfringens* type A is NE in poultry; in countries where the use of antimicrobial growth promoters has been abolished, the incidence of NE has increased and the productivity of the poultry industry has been reduced.

Citation or identification of any document in this application is not an admission that such document is available as prior art to the present invention.

SUMMARY OF THE INVENTION

There exists a growing need for new treatments and approaches for the control of *C. perfringens.*

Bacteriophages and their endolysins present an opportunity to control *C. perfringens* selectively without disturbing the balance of the microbiota in the gastrointestinal (GI) tract. Bacteriophage therapy is a growing area of research and tests in poultry have demonstrated the potential of bacteriophages to control levels of *C. perfringens, Salmonella* and *Campylobacter*. However, the narrow host range of bacteriophages and the rapid development of resistance to them can limit their application as control agents. At the end of their life cycle, lytic bacteriophages release their progeny by lysis of the host cell, through two proteins encoded by the lysis cassette. First, small hydrophobic proteins, termed holins, disrupt the cell membrane to produce holes through which endolysins can then pass. The endolysins are cell wall hydrolases, which directly target bonds in the peptidoglycan. The result of their activity is the destruction of the cell and the release of newly produced virions.

With few exceptions, endolysins consist of two domains: the N-terminal domain usually contains the catalytic activity of the enzyme (e.g., muramidase, glucosaminidase, endopeptidase or amidase) which specifically cleaves one of the major bonds found in the peptidoglycan, while the C-terminal domain binds to a specific substrate found in the cell wall of the host bacterium. Properties such as the specificity for their host pathogen, leading to minimal disturbance of the normal flora, the low risk of bacterial resistance and the ability to kill colonizing pathogens on mucosal surfaces make endolysins ideal anti-infective agents.

Recent studies have demonstrated the efficiency of endolysins in killing or controlling pathogenic bacteria in animal models; they have also shown efficacy against biofilms, as disinfectants and as the basis of detection systems for bacteria. Several bacteriophage endolysins which produce lytic activity against *C. perfringens* cells have been identified. A number have also been identified by sequencing and genome mining, producing a rich resource of information for such enzymes.

To find new control strategies to treat *C. perfringens* infection, the inventors investigated the activity and delivery of a bacteriophage endolysin. They succeeded in identifying a new endolysin, designated CP51L, which shows similarity to an N-acetylmuramoyl-L-alanine amidase domain but not to other *C. perfringens* endolysins whose activity has been demonstrated in vitro. The cp51l gene was cloned and expressed in *Escherichia coli* and the gene product demonstrated lytic activity against all 25 *C. perfringens* strains tested (see Examples below). A probiotic strain of *Lactobacillus johnsonii* FI9785 was engineered to produce a system for delivery of the endolysin to the gastrointestinal tract. The integration of the nisRK two component regulatory system from the *Lactococcus lactis* nisin A biosynthesis operon into the chromosome of *L. johnsonii* allowed constitutive expression of the endolysin under the control of the nisA promoter ($P_{nisA}$), while the use of a signal peptide (SLPmod) successfully secreted the active endolysin to the surrounding media. The high specificity and activity of the endolysin demonstrates its utility as an effective tool to enhance the control of *C. perfringens* by *L. johnsonii* in the gastrointestinal tract.

*Lactobacillus johnsonii* FI9785 is a poultry-isolated strain which has been shown to act as a competitive exclusion agent against *C. perfringens* in chickens. As well as acting as probiotics in their own right, lactic acid bacteria have also shown promise as delivery systems for the secretion of biologically active interleukins or peptidoglycan hydrolases. The promoter of the lantibiotic nisin A ($P_{nisA}$) is induced by nisin A via signal transduction using the two component regulatory system NisRK. This system has been exploited to develop gene expression systems in *Lactococcus lactis, Leuconostoc lactis* and *Lactobacillus helveticus*. Here, the inventors have expressed the endolysin CP51L, originating from a prophage of *C. perfringens* (see Examples, below), both in *Escherichia coli* for enzymatic analysis and in a probiotic strain of *L. johnsonii* which was engineered for delivery to the GI tract.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 3. Alignment of the amino acid sequence of CP51L compared with putative N-acetylmuramoyl-L-alanine amidases from *C. perfringens* genomes (SEQ ID NOS. 14 to 19). Black line, homology with PGRP and Amidase_2 domains (amino acids 18-134, corresponding to the proposed catalytic domain), grey line, homology with SH3_3 bacterial domain (amino acids 322-375, proposed cell wall binding).

FIG. 4A—SDS-PAGE analysis of crude protein lysates from *E. coli* harbouring pET15b-cp51l or the vector control. Lane 1, SeeBlue Plus2 marker, lanes 2-7 lysates from *E. coli* containing pET15b-cp51l (2-4) and pET15b (5-7) after extraction with NP buffer (2, 5), TN buffer (3, 6) or EB (4, 7). FIG. 4B Western blot analysis of the same samples with a His Tag antibody. FIG. 4C—Activity of crude extracts from *E. coli* harbouring pET15b-cp51l (filled symbols) or pET15b (open symbols) extracted with NP (▲), TN (●) or EB (■). (D) pH profile of endolysin activity. Results represent the percentage decrease in $OD_{600}$ over 4 min of linear lysis. Endolysin activity was measured using 10 mg crude protein extract incubated with fresh (C) or frozen (D) cells of *C. perfringens*, results are the mean of duplicate assays±standard deviation.

FIG. 5A-B. Effect of endolysin concentration (A) and lysis medium (B) on lytic activity. Partially-purified protein extracts from *E. coli* were incubated with frozen cells of *C. perfringens*. FIG. 5A—■, 30 µg, □, 10 µg, ●, 1 µg, ▲, 0.1 µg and ●, 0.01 µg of CP51L compared to buffer control (EB, ●). FIG. 5B—Cells were resuspended in PBS (Δ), BHI+C, (▲) or CM (■) and incubated with 10 µg CP51L (closed symbols) or EB (open symbols). Results are the mean of duplicate assays±standard deviation.

FIG. 8A-B. Endolysin delivery from *L. johnsonii*. FIG. 8A—Plate assay showing lysis from crude protein extracts (1-4) and concentrated supernatants (5-7, 20× concentrated; 9-12, 166× concentrated) from *L. johnsonii* FI10744-L induced with nisin (1, 5, 9) or uninduced (3, 7, 11), *L. johnsonii* FI10744-V induced with nisin (2, 6, 10) or uninduced (4, 12); 8, EB control. FIG. 8B—Lytic zones produced by growing colonies of FI10744-L (L) compared to control FI10744-V (V) on media incorporating autoclaved *C. perfringens*.

FIG. 10A-C. Co-culture of *C. perfringens* and *L. johnsonii* in batch cultures. Cell counts were taken from three separate experiments (FIGS. 10A, 10B, 10C). Vessels contained either *L. johnsonii* FI9785 pure culture (striped bars), *C. perfringens* pure culture (white bars) or *L. johnsonii* FI9785 (black bars) in co-culture with *C. perfringens* (grey bars).

FIG. 11A-C. Co-culture of *C. perfringens* with *L. johnsonii* expressing endolysin. Cell counts were taken from three separate experiments (FIGS. 11A, 11B, 11C). Vessels contained either *L. johnsonii* FI9785-L (black bars) with *C. perfringens* (grey bars) or *L. johnsonii* FI9785-V (striped bars) with *C. perfringens* (white bars).

DETAILED DESCRIPTION OF THE INVENTION

Figure 1:
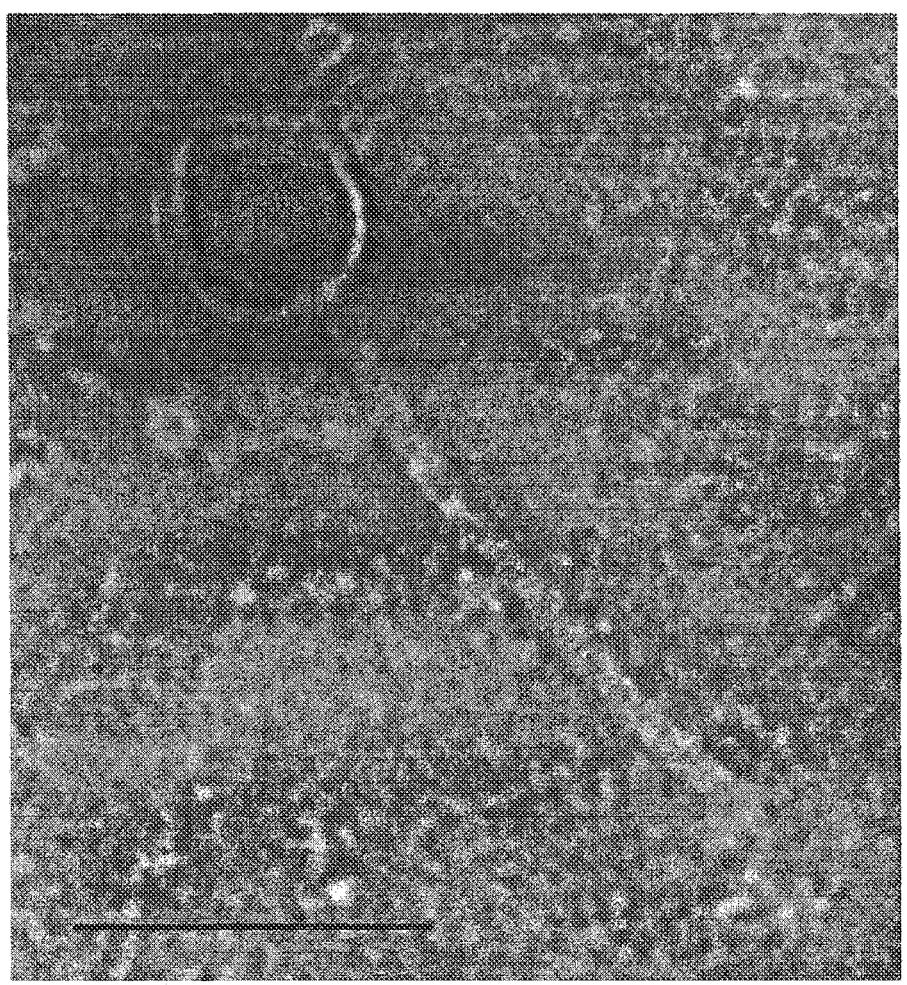
FIG. 1. Electron microscopy of φCP51. Sample was viewed at a magnification of 29000×; bar represents 100 nm.
Figure 2:
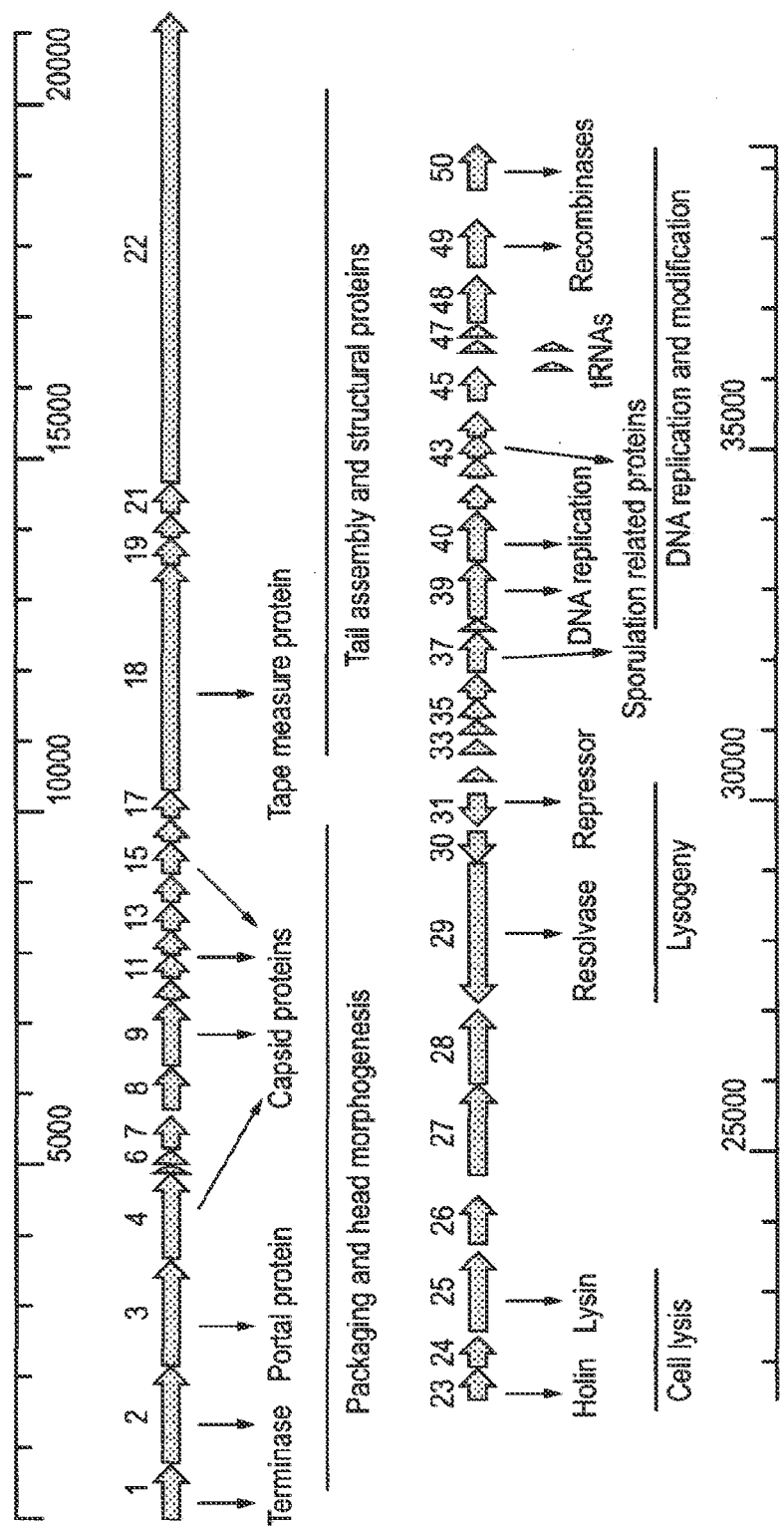
FIG. 2. φCP51 genome organisation with predicted ORFs. Arrows indicate the direction of transcription. Proposed functional modules are marked based on BLASTp results.
Figure 4A:
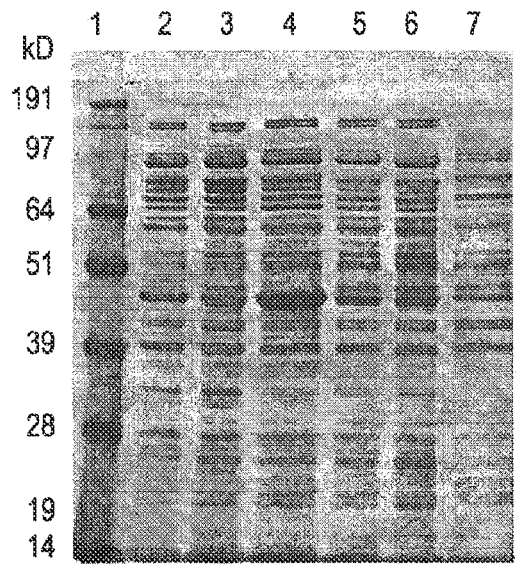
FIG. 4A-D. Expression of CP51L in *E. coli*.
Figure 4B:
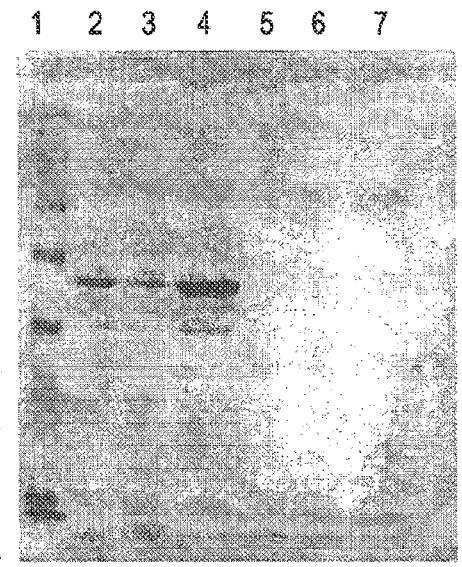
Figure 4C:
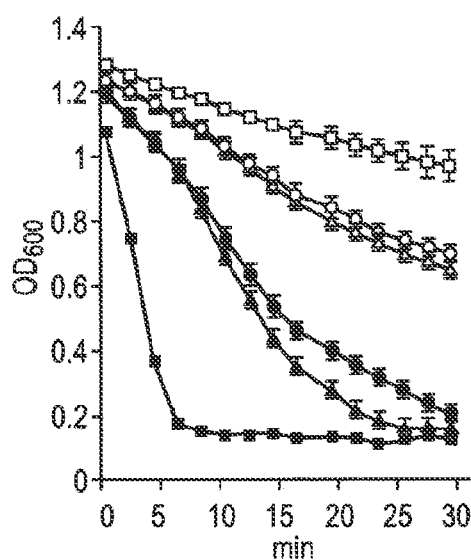
Figure 4D:
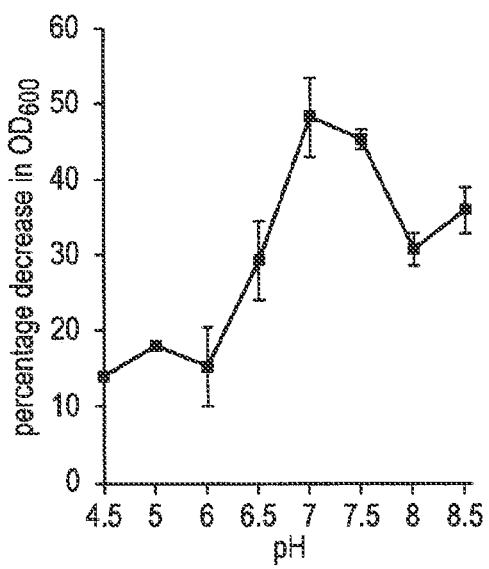
Figure 6A:
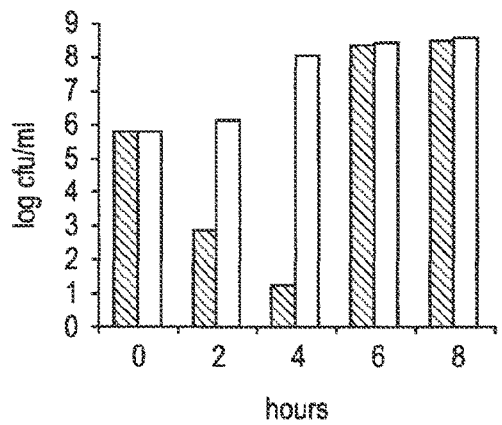
FIG. 6A-B. Viability assays under anaerobic conditions to examine the effect of 166 µg partially-purified CP51L (black bars) on the viability of *C. perfringens* in comparison with the buffer control (white bars). Endolysin was added to the media either at point of inoculation (0 h) FIG. 6A, or during the early exponential phase ($OD_{600}$ 0.3, 3.5 h) FIG. 6B.
Figure 6B:
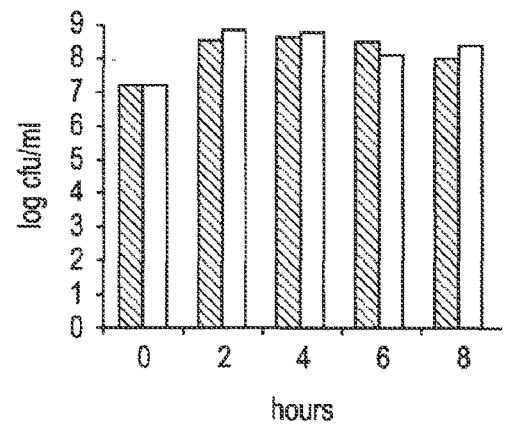

A first aspect of the invention provides an isolated polypeptide which may comprise the amino acid sequence of SEQ ID NO:1, or a fragment, variant, derivative or fusion thereof which is capable of binding specifically to and/or lysing cells of *Clostridium perfringens*.

The amino acid sequence depicted below is that of the wildtype (i.e., naturally occurring) endolysin (CP51L) of bacteriophage φCP51 of *Clostridium perfringens*.

[SEQ ID NO: 1]
MYINQSNIKFNGLRYGNDPNKIIIHNADATSCSVYDIDRWHKGNGWSGIG

YDYFIRKEGSVWTGRPENAIGAHTIGQNSSSIGICLEGAFMREKPTRAQL

NSLYELIADIRARRGNLPVYGHKDFNNTDCPGINFPLEQFKNNSYRPTGG

EIVSDNGFYRSDEERTNATIVGEGNIEVLDKNCKVIENRYISSLDRVFVL

GIYPASKYIEIIYPAGNEKYHAYISIENYSRISFDYHMQYKNDNGVTYVW

WDSEDVNVKEHNEELQANQKASPMYRVGKWLRVTFYRTDGTPSDGFVRYE

GEQAVKFYEEEKIKEGIVKVNTYLNVRDSINGNIIGKVFNGEEVSIIWTK

DGWYYIDYNTNHGKKRGYVSSKYVEEV

In one embodiment, the polypeptide is not a naturally occurring lysin of a bacteriophage of *Clostridium perfringens* (other than CP51L). Thus, the first aspect of the invention encompasses isolated polypeptides which may comprise or consist of the amino acid sequence of SEQ ID NO: 1 and non-naturally occurring fragments, variants, derivatives or fusions thereof.

The term 'amino acid' as used herein includes the standard twenty genetically-encoded amino acids and their corresponding stereoisomers in the 'D' form (as compared to the natural l' form), omega-amino acids and other naturally-occurring amino acids, unconventional amino acids (e.g., a,a-disubstituted amino acids, N-alkyl amino acids, etc.) and chemically derivatised amino acids (see below).

Thus, when an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

Preferably, the polypeptide, or fragment, variant, fusion or derivative thereof, may comprise or consist of L-amino acids.

By "isolated" Applicants mean that the polypeptide of the invention, specifically the wildtype endolysin of bacteriophage CD51, is provided in a form other than that in which it may be found naturally. Preferably, the polypeptide is provided free from intact bacteriophage.

In one embodiment, the polypeptide of the invention is the naturally occurring endolysin of bacteriophage CP51 [SEQ ID NO: 1], provided in an isolated form.

Other naturally occurring lysins of a bacteriophage of *Clostridium perfringens* known in the prior art are specifically not encompassed by the first aspect of the invention. In particular, the following lysins of bacteriophage of *Clostridium perfringens* are explicitly excluded from the scope of the first aspect of the invention:

(a) the lysin ply φ3626 (see Zimmer M, Vukov N, Scherer S, Loessner M J. 2002. The murein hydrolase of the bacteriophage (I)3626 dual lysis system is active against all tested *Clostridium perfringens* strains. Appl Environ Microbiol. 68:5311-7);

(b) the lysin plyCP26F (see Simmons M, Donovan D M, Siragusa G R, Seal B S. 2010. Recombinant expression of two bacteriophage proteins that lyse *Clostridium perfringens* and share identical sequences in the C-terminal cell wall binding domain of the molecules but are dissimilar in their N-terminal active domains. J Agric Food Chem. 58:10330-7);

(c) the lysin plyCP39O (see Simmons M, Donovan D M, Siragusa G R, Seal B S. 2010. Recombinant expression of two bacteriophage proteins that lyse *Clostridium perfringens* and share identical sequences in the C-terminal cell wall binding domain of the molecules but are dissimilar in their N-terminal active domains. J Agric Food Chem. 58:10330-7);

(d) the lysin Pms (see Nariya H, Miyata S, Tamai E, Sekiya H, Maki J, Okabe A. 2011. Identification and characterization of a putative endolysin encoded by episomal phage φSM101 of *Clostridium perfringens*. Appl Microbiol Biotechnol. 90:1973-9); and (e) the lysin PlyCM (see Schmitz J E, Ossiprandi M C, Rumah K R, Fischetti V A. 2011. Lytic enzyme discovery through multigenomic sequence analysis in *Clostridium perfringens*. Appl Microbiol Biotechnol. 89:1783-95).

In one embodiment, the polypeptide of the first aspect of the invention may comprise the amino acid sequence of SEQ ID NO: 1. For example, the polypeptide may consist of the amino acid sequence of SEQ ID NO: 1.

However, the first aspect of the invention also extends to fragments, variants, derivatives and fusions of the amino acid sequence of SEQ ID NO:1 which are capable of binding specifically to and/or lysing cells of *Clostridium perfringens*.

By "capable of binding specifically to cells of *Clostridium perfringens*" Applicants mean that the polypeptide is capable of binding preferentially to cells of *Clostridium perfringens*. However, it will be appreciated that such polypeptides may also bind preferentially to one or more additional types of cell.

By "capable of lysing cells of *Clostridium perfringens*" Applicants mean that the polypeptide, or fragment, variant, derivative or fusion, retains (at least in part) the ability of the wildtype endolysin of bacteriophage CP51 to lyse bacterial cells (e.g., cells of *Clostridium perfringens*). However, it will be appreciated that such polypeptides may also preferentially lyse one or more additional types of cell. It will be appreciated that such lytic activity should be cell-specific rather than a non-specific cytotoxic activity on all cell types. Such cell lysis activity may be determined using methods well known in the art, such as those described in detail in the Examples below (see also Loessner M J. 2005. Bacteriophage endolysins—current state of research and applications. *Curr Opin Microbiol.* 8:480-7, the disclosures of which are incorporated herein by reference). Preferably, the ability of polypeptides to lyse cells of *Clostridium perfringens* is determined using fresh cells.

Other types of cell to which the polypeptides of the invention may also bind and/or lyse may be selected from the group consisting of cells of *Bacillus* sp. and other *Clostridium* sp. For example, where the other type of cell is a *Bacillus* sp., the *Bacillus* sp. may be selected from the group consisting of *Bacillus cereus* (e.g., *B. cereus* NCIMB 11796) and *B. subtilis* (e.g., *B. subtilis* ATCC 6633). Alternatively, where the other type of cell is another *Clostridium* sp., the *Clostridium* sp. may be selected from the group consisting of *C. acetobutylicum* (e.g., *C. acetobutylicum* BL75141), *C. bifermentans* (e.g., *C. bifermentans* NCTC 13019) and *C. beijerinckii* (e.g., *C. beijerinckii* NCIMB 8052).

However, in one embodiment the polypeptide exclusively binds to and/or lyses cells of *Clostridium* sp. (e.g., *C. perfringens*). Preferably, such cell binding activity may be determined using methods well known in the art, in particular, those described in the Examples, below.

In a further embodiment, the polypeptide is substantially incapable of binding to and/or lysing cells selected from of the group consisting of *Anaerococcus hydrogenalis* DSMZ 7454, *Bacillus amyloliquefaciens* 0880, *Bifidobacterium adolescentis* DSMZ 20083, *Bifidobacterium angulatum* DSMZ 20098, *Bifidobacterium bifidum* DSMZ 20082, *Bifidobacterium longum* DSMZ 20219, *Bifidobacterium pseudocatenulatum* DSMZ 20438, *Clostridium cellobioparum* DSMZ 1351, *Clostridium coccoides* NCTC 11035, *Clostridium colinum* DSMZ 6011, *Clostridium difficile* NCTC 11204, *Clostridium innocuum* DSMZ 1286, *Clostridium leptum* DSMZ 753, *Clostridium nexile* DSMZ 1787, *Clostridium ramosum* DSMZ 1402, *Clostridium sordellii* NCTC 13356, *Clostridium sporogenes* ATCC 7886, *Clostridium tyrobutyricum* NCIMB 9582, *Enterococcus faecalis* FI10734, *Enterococcus hirae* FI10477, *Eubacterium barkeri* DSMZ 1223, *Lactobacillus casei* FI10736, *Lactobacillus johnsonii* FI9785, *Lactobacillus plantarum* FI08595, *Lactobacillus rhamnosus* FI10737, *Lactococcus lactis* MG1363, *Leuconostoc mesenteroides* subsp. *Mesenteroides* ATCC 8293, *Listeria innocua* NCTC 11288, *Listeria ivanovii* NCTC 11007, *Micrococcus luteus* FI10640, *Pediococcus pentosaceus* FI10642, *Pediococcus acidilactici* FI10738, *Salmonella enterica* serovar Typhimurium FI10739, *Salmonella enterica* serovar Enteritidis FI10113 and *Staphylococcus aureus* FI10139. Preferably, the polypeptide is incapable of lysing any of the cells in the preceding list.

In a preferred embodiment, the ability of polypeptides to lyse cells of *Clostridium perfringens* is determined using cells of strain NCTC 3110 and/or NCTC 8238.

It will be appreciated by persons skilled in the art that the polypeptide, or fragment, variant, derivative or fusion, need not retain all of the ability of the wildtype endolysin of bacteriophage CP51 to lyse bacterial cells. Rather, it is simply necessary for said polypeptide, fragment, variant, derivative or fusion to retain at least 10% of the ability of the wildtype endolysin of bacteriophage CP51 to lyse bacterial cells. Preferably, however, the polypeptide, fragment, variant, derivative or fusion exhibits at least 20%, for example at least 30%, 40%, 50%, 60%, 70%, 80%, 90%, 100%, 150%, 200% or more, of the ability of the wildtype endolysin of bacteriophage CP51 to lyse bacterial cells.

In one embodiment of the first aspect of the invention, the polypeptide may comprise or consist of a fragment of the amino acid sequence of SEQ ID NO: 1, which is capable of lysing cells of *Clostridium perfringens*.

The fragment may comprise or consist of at least 50 contiguous amino acids of SEQ ID NO: 1, for example at least 60, 70, 80, 90, 95, 100, 110, 120, 130, 140, 150, 160, 170, 175, 180, 190, 200, 210, 220, 230, 240, 250, 260, 265, 275, 285, 295, 300, 305, 310, 315, 320, 325, 335, 340, 345, 355, 360, 365, 370, 375 or 376 contiguous amino acids of SEQ ID NO: 1.

As noted above, it is well established that many bacteriophage endolysins consist of two distinct domains (for example, see Sheehan et al., 1996, *FEMS Microbiology Letters* 140:23-28, the disclosures of which are incorporated herein by reference). One is a catalytic domain that is responsible for cell wall degradation and these are known to exist in several different forms. The other domain is a cell wall binding domain that recognises a cell surface motif and permits attachment of the endolysin to that target cell. The precise pattern recognition involved in the latter is what provides the specificity.

The enzymatic domain can be identified by its amino acid homology to other similar regions of lytic enzymes that share the same type of lytic activity. In the case of the endolysin of bacteriophage CP51, Blastp analysis of CP51L identified 2 regions with similarity to conserved domains separated by a central section (see FIG. 3, below).

The N-terminal region of the endolysin is most similar to domains associated with lysis, including the peptidoglycan recognition protein (PGRP, cd06583), lysozyme (PHA00447) and amidase_2 (N-acetylmuramoyl-L-alanine amidase, pfam01510). This is confirmed by alignment analysis of SEQ ID NO: 1 with known enzymatic domains, for example using the NCBI CDD search tool; see Marchler-Bauer & Bryant, 2004, *Nuc. Acids Res.* 32[W]:327-331, the disclosures of which are incorporated herein by reference).

The C-terminal region has similarity to a bacterial SH3 domain (SH3_3, pfam08239) towards the end of the sequence. SH3 (src Homology-3) domains are small protein modules containing approximately 50 amino acid residues (see Pawson T & Schlessingert J, 1993, SH2 and SH3 domains. *Cum Biol.* 3(7):434-42; Mayer B J, 2001, SH3 domains: complexity in moderation. *J. Cell Sci.* 114(7): 1253-63; Gu J et al., 2011, LysGH15B, the SH3b domain of staphylococcal phage endolysin LysGH15, retains high affinity to staphylococci, *Curr Microbiol.* 63(6):538-42; Xu Q et al., 2009, Structural basis of murein peptide specificity of a gamma-D-glutamyl-I-diamino acid endopeptidase, *Structure* 17(2):303-13;). They are found in a great variety of intracellular or membrane-associated proteins (see Musacchio A, Gibson T, Lehto V P, & Saraste M, 1992, SH3—an abundant protein domain in search of a function. *FEBS Lett.* 307(1):55-61 Mayer B J & Baltimore D, 1993, Signalling through SH2 and SH3 domains. *Trends Cell. Biol.* 3(1):8-13; Pawson T, 1995, Protein modules and signalling networks. *Nature* 373(6515):573-80) for example, in a variety of proteins with enzymatic activity, in adaptor proteins that lack catalytic sequences and in cytoskeletal proteins, such as fodrin and yeast actin binding protein ABP-1.

The SH3 domain has a characteristic fold which consists of five or six beta-strands arranged as two tightly packed anti-parallel beta sheets. The linker regions may contain short helices (see Kuriyan J. & Cowburn D, 1997, Modular peptide recognition domains in eukaryotic signalling. *Annu Rev Biophys Biomol Struct.* 26:259-88). The surface of the SH3-domain bears a flat, hydrophobic ligand-binding pocket which consists of three shallow grooves defined by conservative aromatic residues in which the ligand adopts an extended left-handed helical arrangement. The ligand binds with low affinity but this may be enhanced by multiple interactions. The region bound by the SH3 domain is in all cases proline-rich and contains MOO as a core-conserved binding motif. The function of the SH3 domain is not well understood but they may mediate many diverse processes such as increasing local concentration of proteins, altering their subcellular location and mediating the assembly of large multiprotein complexes (Morton & Campbell, 1994, *Curr. Biol.* 4(7):615-7).

A homologue of the SH3 domain has been found in a number of different bacterial proteins including glycyl-glycine endopeptidase, bacteriocin and some hypothetical proteins.

In one embodiment, the polypeptide of the invention may comprise an enzymatic domain contained within amino acids 18 to 134 of SEQ ID NO:1. Thus, the fragment which may comprise the enzymatic domain may consist of the sequence of SEQ ID NO: 1 starting from any of amino acids 1, 5, 10, 15, 16, 17, 18, 19, 20, 25, 30, 35, 40, 45, 50, 60, 70, 80, 90 or 100 and ending at any of amino acids, 145, 140, 135, 134, 133, 132, 131, 130, 125, 120, 115, 110 or 105. For example, the fragment which may comprise the enzymatic domain may consist of amino acids 15 to 140 of SEQ ID NO: 1, or amino acids 18 to 134 of SEQ ID NO: 1, or any of the other possible permutations of the above start and end points.

In one embodiment, the polypeptide of the invention may comprise an SH3_3 domain contained within amino acids 322 to 375 of SEQ ID NO: 1. Thus, the fragment which may comprise the cell wall binding domain may consist of the sequence of SEQ ID NO: 1 starting from any of amino acids 280, 285, 290, 295, 300, 305, 310, 315, 320, 325, 330, 335 or 340 and ending at any of amino acids 350, 355, 360, 365, 370, 375 or 377. For example, the fragment which may comprise the cell wall binding domain may consist of amino acids 315 to 377 of SEQ ID NO: 1, or amino acids 320 to 376 of SEQ ID NO: 1, or any of the other possible permutations of the above start and end points.

Optionally, the polypeptide of the invention may comprise an amino acid sequence corresponding to a sequence within the central region of SEQ ID NO: 1. Thus, the polypeptide may comprise at least 20 contiguous amino acids from amino acids 135 to 321 of SEQ ID NO: 1, for example starting from any of amino acids 140, 150, 160, 170, 180, 190, 200, 210, 220, 230, 240 or 250 of SEQ ID NO: 1 and ending at any of amino acids 320, 310, 300, 290, 280, 270, 260, 250, 240, 230, 220, 210 or 200 of SEQ ID NO: 1. In one embodiment, this amino acid sequence may enhance the cell wall binding and/or lytic activity of the polypeptide of the invention.

The polypeptide of the first aspect of the invention preferably may comprise or consist of one or more fragments of the amino acid sequence of SEQ ID NO:1 corresponding to:

a. an enzymatic domain from within the N-terminal region of SEQ ID NO: 1 (i.e., from within amino acids 18 to 134 of SEQ ID NO:1);

b. a cell wall binding domain from within the C-terminal region of SEQ ID NO: 1 (i.e., from within amino acids 322 to 375 of SEQ ID NO:1); and/or c. a further domain from within the central region of SEQ ID NO: 1 (i.e., from within amino acids 135 to 321 of SEQ ID NO:1).

Thus, in one embodiment, the polypeptide may comprise or consist of an enzymatic domain from within the N-terminal region of SEQ ID NO: 1 and a cell wall binding domain from within the C-terminal region of SEQ ID NO: 1.

However, it will be appreciated by persons skilled in the art that the cell wall binding domain of SEQ ID NO:1 may alternatively be fused or otherwise coupled to an enzymatic (lytic) domain from another source capable of lysing cells of *Clostridium perfringens*. The production of such chimeric lysins is described in Sheehan et al., 1996, *FEMS Microbiology Letters* 140:23-28, the disclosures of which are incorporated herein by reference). Thus, in an alternative embodiment, the polypeptide of the first aspect of the invention may comprise one or more fragments of the amino acid sequence of SEQ ID NO:1 corresponding to the cell wall binding domain but without an enzymatic domain of SEQ ID NO:1.

In an alternative embodiment, the polypeptide of the first aspect of the invention may comprise or consist of a variant of the amino acid sequence of SEQ ID NO:1, or of a fragment thereof, which is capable of lysing cells of *Clostridium perfringens*.

By 'variant' of the polypeptide Applicants include insertions, deletions and/or substitutions, either conservative or non-conservative, relative to the amino acid sequence of SEQ ID NO:1. In particular, the variant polypeptide may be a non-naturally occurring variant.

For example, the polypeptide may comprise an amino acid sequence with at least 60% identity to the amino acid sequence of SEQ ID NO: 1, more preferably at least 70% or 80% or 85% or 90% identity to said sequence, and most preferably at least 95%, 96%, 97%, 98% or 99% identity to said amino acid sequence.

It will be appreciated that the above sequence identity may be over the full length of the amino acid sequence of SEQ ID NO: 1 or over a portion thereof. Preferably, however, the sequence identity is over at least 50 amino acids of the amino acid sequence of SEQ ID NO: 1, for example at least 60, 70, 80, 90, 100, 110, 120, 130, 140, 150, 160, 170, 180, 190, 200, 210, 220, 230, 240, 250, 260, 265, 275, 285, 295, 300, 305, 310, 315, 320, 325, 335, 340, 345, 355, 360, 365, 370, 375 or 376 or more amino acids therein.

Percent identity can be determined by methods well known in the art, for example using the LALIGN program (Huang and Miller, *Adv. Appl. Math.* (1991) 12:337-357, the disclosures of which are incorporated herein by reference) at the ExPASy facility website using as parameters the global alignment option, scoring matrix BLOSUM62, opening gap penalty −14, extending gap penalty −4.

Alternatively, the percent sequence identity between two polypeptides may be determined using suitable computer programs, for example AlignX, Vector NTI Advance 10 (from Invitrogen Corporation) or the GAP program (from the University of Wisconsin Genetic Computing Group).

It will be appreciated that percent identity is calculated in relation to polypeptides whose sequence has been aligned optimally.

Fragments and variants of the amino acid sequence of SEQ ID NO: 1 may be made using any of the methods of protein engineering, directed evolution and/or site-directed mutagenesis well known in the art (for example, see *Molecu-* lar *Cloning: a Laboratory Manual,* 3rd edition, Sambrook & Russell, 2001, Cold Spring Harbor Laboratory Press, the disclosures of which are incorporated herein by reference).

It will be appreciated by skilled persons that the polypeptide of the invention, or fragment, variant or fusion thereof, may comprise one or more amino acids that are modified or derivatised. Thus, the polypeptide may comprise or consist of a derivative of the amino acid sequence of SEQ ID NO:1, or of a fragment or variant thereof.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g., acetylation or thioglycolic acid amidation), terminal carboxylamidation (e.g., with ammonia or methylamine), and the like terminal modifications.

It will be further appreciated by persons skilled in the art that peptidomimetic compounds may also be useful. Thus, by 'polypeptide' Applicants include peptidomimetic compounds which exhibit endopeptide activity. The term 'peptidomimetic' refers to a compound that mimics the conformation and desirable features of a particular polypeptide as a therapeutic agent.

For example, the polypeptides described herein include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, the disclosures of which are incorporated herein by reference. Such retro-inverse peptides, which contain NH—CO bonds instead of CO—NH peptide bonds, are much more resistant to proteolysis. Alternatively, the polypeptide of the invention may be a peptidomimetic compound wherein one or more of the amino acid residues are linked by a -y(CH$^2$NH)— bond in place of the conventional amide linkage.

It will be appreciated that the polypeptide may conveniently be blocked at its N- or C-terminus so as to help reduce susceptibility to exoproteolytic digestion, e.g., by amidation.

As discussed above, a variety of uncoded or modified amino acids such as D-amino acids and N-methyl amino acids may be used to modify polypeptides of the invention. In addition, a presumed bioactive conformation may be stabilised by a covalent modification, such as cyclisation or by incorporation of lactam or other types of bridges. Methods of synthesis of cyclic homodetic peptides and cyclic heterodetic peptides, including disulphide, sulphide and alkylene bridges, are disclosed in U.S. Pat. No. 5,643,872. Other examples of cyclisation methods are discussed and disclosed in U.S. Pat. No. 6,008,058, the relevant disclosures in which documents are hereby incorporated by reference. A further approach to the synthesis of cyclic stabilised peptidomimetic compounds is ring-closing metathesis (RCM).

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification and is preferred because of the stable structures formed by cyclisation and in view of the biological activities observed for cyclic peptides.

Thus, in one embodiment the polypeptide, or fragment, variant, fusion or derivative thereof, is cycliC. However, in a preferred embodiment, the polypeptide, or fragment, variant, fusion or derivative thereof, is linear.

In a further embodiment of the first aspect of the invention, the polypeptide may comprise or consist of a fusion of the amino acid sequence of SEQ ID NO:1, or of a fragment, variant or derivative thereof.

By 'fusion' of a polypeptide Applicants include a polypeptide which is fused to any other polypeptide. For example, the polypeptide may comprise one or more additional amino acids, inserted internally and/or at the N- and/or C-termini of the amino acid sequence of SEQ ID NO:1, or of a fragment, variant or derivative thereof.

Thus, as described above, in one embodiment the polypeptide of the first aspect of the invention may comprise a fragment of SEQ ID NO: 1 consisting of the cell wall binding domain (or a variant of such a domain sequence which retains the cell wall binding activity thereof), to which is fused an enzymatic domain from a different source.

Examples of other suitable enzymatic domains include:
L-alanoyl-D-glutamate endopeptidase; D-glutamyl-m-DAP endopeptidase; interpeptide bridge-specific endopeptidase; N-acetyl-β-D-glucosaminidase (=muramoylhydrolase); N-acetyL-β-D-muramidase (=lysozyme); lytic transglycosylase.

Also N-acetylmuramoyl-L-alanine amidase from other sources could be utilised (see Loessner, 2005, *Current Opinion in Microbiology* 8:480-487, the disclosures of which are incorporated herein by reference).

In one embodiment, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well-known Myc tag epitope. Fusions to any fragment, variant or derivative of said polypeptide are also included in the scope of the invention. It will be appreciated that fusions (or variants or derivatives thereof) which retain desirable properties, namely endolysin activity are preferred. It is also particularly preferred if the fusions are ones which are suitable for use in the methods described herein.

For example, the fusion may comprise a further portion which confers a desirable feature on the said polypeptide of the invention; for example, the portion may be useful in detecting or isolating the polypeptide, promoting cellular uptake of the polypeptide, or directing secretion of the protein from a cell. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the polypeptide, as known to those skilled in the art.

It will be appreciated by persons skilled in the art that the polypeptides of the invention also include pharmaceutically acceptable acid or base addition salts of the above described polypeptides. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically acceptable base addition salts may also be used to produce pharmaceutically acceptable salt forms of the polypeptides. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines, among others.

The polypeptide, or fragment, variant, fusion or derivative thereof, may also be lyophilised for storage and reconstituted in a suitable carrier prior to use. Any suitable lyophilisation method (e.g., spray drying, cake drying) and/or reconstitution techniques can be employed. It will be appreciated by those skilled in the art that lyophilisation and reconstitution can lead to varying degrees of activity loss and that use levels may have to be adjusted upward to compensate. Preferably, the lyophilised (freeze dried) polypeptide loses no more than about 20%, or no more than about 25%, or no more than about 30%, or no more than about 35%, or no more than about 40%, or no more than about 45%, or no more than about 50% of its activity (prior to lyophilisation) when rehydrated.

An essential feature of the polypeptides of the invention is the ability to lyse cells of *Clostridium perfringens*. Preferably, the polypeptide is capable of lysing cells of multiple strains of *Clostridium perfringens*. For example, the polypeptide may be capable of lysing one or more of the strains of *Clostridium perfringens* lysed by the CP51 lysin of SEQ ID NO: 1 (see Table 1 below).

In one embodiment, the polypeptides of the invention are substantially incapable of lysing bacteria which are commensal members of the microbiota of a healthy gut (and not known to cause adverse effects on the host). For example, it is advantageous if the polypeptide does not lyse cells of *Clostridium* clusters IV (e.g., *Clostridium leptum*), cluster XIVa (e.g., *Clostridium nexile, Clostridium coccoides*) or cluster XVI (e.g., *Clostridium innocuum*).

Most preferably, the polypeptide of the invention is capable of lysing cells of *Clostridium perfringens* strain NCTC 3110 and/or NCTC 8238. For example, the polypeptide may exhibit at least 10% of the lysis activity of the polypeptide of SEQ ID NO: 1 on cells of *Clostridium perfringens* strain NCTC 3110 and/or NCTC 8238, for example at least 20%, 30%, 40%, 50%, 60%, 70%, 80%, 90%, 100% or more. The polypeptide may even exhibit a greater lysis activity than the polypeptide of SEQ ID NO: 1 on cells of *Clostridium perfringens* strain NCTC 3110 and/or NCTC 8238, for example at least 110%, 120%, 130%, 140%, 150%, 160%, 170%, 180%, 190%, 200%, 250%, 300%, 500% or more.

Advantageously, the polypeptide is capable of lysing cells of pathogenic bacteria selectively, i.e. to a greater extent than cells of non-pathogenic bacteria.

Methods for the production of polypeptides, or a fragment, variant, fusion or derivative thereof, for use in the first aspect of the invention are well known in the art. Conveniently, the polypeptide, or fragment, variant, fusion or derivative thereof, is or may comprise a recombinant polypeptide.

Thus, a nucleic acid molecule (or polynucleotide) encoding the polypeptide, or fragment, variant, fusion or derivative thereof, may be expressed in a suitable host and the polypeptide obtained therefrom. Suitable methods for the production of such recombinant polypeptides are well known in the art (for example, see Sambrook & Russell, 2000, *Molecular Cloning, A Laboratory Manual*, Third Edition, Cold Spring Harbor, N.Y., the relevant disclosures in which document are hereby incorporated by reference).

In brief, expression vectors may be constructed which may comprise a nucleic acid molecule which is capable, in an appropriate host, of expressing the polypeptide encoded by the nucleic acid molecule.

A variety of methods have been developed to operably link nucleic acid molecules, especially DNA, to vectors, for example, via complementary cohesive termini. For instance, complementary homopolymer tracts can be added to the DNA segment to be inserted into the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, e.g., generated by endonuclease restriction digestion, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a larger molar excess of linker molecules in the presence of an enzyme that is able to catalyse the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

The DNA (or in the case of retroviral vectors, RNA) is then expressed in a suitable host to produce a polypeptide. Thus, the DNA encoding the polypeptide may be used in accordance with known techniques, appropriately modified in view of the teachings contained herein, to construct an expression vector, which is then used to transform an appropriate host cell for the expression and production of the compound of the invention or binding moiety thereof. Such techniques are well known in the art.

The DNA (or in the case of retroviral vectors, RNA) encoding the polypeptide may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector.

Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the expression vector are then cultured for a sufficient time and under appropriate conditions known to those skilled in the art in view of the teachings disclosed herein to permit the expression of the polypeptide, which can then be recovered.

Many expression systems are known, including bacteria (for example, *E. coli* and *Bacillus subtilis*), yeasts (for example *Saccharomyces cerevisiae*), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Other vectors and expression systems are well known in the art for use with a variety of host cells.

The host cell may be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No. ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH5200 and YPH501 which are generally available from Stratagene Cloning Systems, La Jolla, Calif. 92037, USA. Preferred mammalian host cells include Chinese hamster ovary (CHO) cells available from the ATCC as CRL 1658 and 293 cells which are human embryonic kidney cells. Preferred insect cells are Sf9 cells which can be transfected with baculovirus expression vectors.

Methods of cultivating host cells and isolating recombinant proteins are well known in the art. It will be appreciated that, depending on the host cell, the polypeptides of the invention produced may differ. For example, certain host cells, such as yeast or bacterial cells, either do not have, or have different, post-translational modification systems which may result in the production of forms of compounds of the invention which may be post-translationally modified in a different way.

Polypeptides of the invention may also be produced in vitro using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

Automated polypeptide synthesisers may also be used, such as those available from CS Bio Company Inc, Menlo Park, USA.

Thus, a second aspect of the present invention provides an isolated nucleic acid molecule encoding a polypeptide according to the first aspect of the invention.

The nucleic acid molecule may be DNA (e.g., cDNA) or RNA.

In a preferred embodiment, the nucleic acid molecule may comprise or consist of the nucleotide sequence of SEQ ID NO 2:

[SEQ ID NO: 2]
ATGTATATAAATCAATCAAATATTAAATTCAATGGATTAAGATATGGAAA

TGATCCTAATAAAATAATTATTCATAATGCAGATGCAACTTCATGTAGTG

TATATGATATAGATAGATGGCATAAAGGAAATGGATGGAGTGGCATAGGC

TATGATTATTTTATTAGAAAAGAGGGTTCAGTTTGGACTGGTAGACCAGA

AAATGCAATAGGAGCTCACACAATAGGTCAAAACAGTTCAAGTATAGGAA

TTTGCTTAGAAGGGGCTTTCATGAGAGAAAAACCAACTAGAGCACAATTA

AATTCTCTTTATGAGTTAATTGCAGATATTAGAGCTAGAAGAGGTAACTT

ACCTGTATATGGACATAAGGATTTTAATAATACAGATTGTCCAGGAATAA

ACTTCCCACTAGAGCAATTTAAAAATAATTCATATAGACCAACTGGAGGA

GAAATAGTATCAGATAATGGCTTTTATAGAAGTGATGAAGAAAGAACAAA

TGCTACAATAGTTGGGGAAGGAAATATTGAAGTATTAGATAAAAATTGTA

AAGTTATTGAGAATAGATATATATCTAGTTTGGATAGAGTTTTTGTATTA

GGAATATATCCAGCATCTAAATATATAGAAATAATTTATCCAGCAGGAAA

TGAAAAATATCATGCATATATTTCTATAGAAAACTACAGTAGAATATCTT

TTGACTACCATATGCAATATAAAAATGATAATGGAGTTACTTATGTGTGG

TGGGATTCAGAGGATGTTAATGTTAAAGAGCATAATGAAGAATTACAGGC

```
-continued
GAATCAAAAAGCTTCTCCAATGTATAGAGTTGGAAAATGGCTAAGAGTAA

CTTTTTATAGAACTGATGGTACTCCAAGTGATGGATTTGTTCGTTATGAA

GGAGAGCAAGCTGTAAAGTTTTATGAAGAGGAAAAAATTAAAGAGGGTAT

AGTTAAAGTTAATACTTATCTTAATGTTAGAGATAGTATAAATGGAAATA

TAATAGGAAAGGTATTTAATGGTGAAGAAGTTTCAATAATATGGACTAAA

GATGGGTGGTATTACATAGATTACAATACAAATCACGGAAAGAAAAGAGG

ATATGTAAGTTCTAAATATGTAGAAGAAGTATAG
```

A third aspect of the invention provides a vector which may comprise a nucleic acid molecule according to the second aspect of the invention. In one embodiment, the vector is an expression vector. Any suitable vector known in the art may be used. Preferably, the vector is selected from the group consisting of pET15b and pACYC184.

It will be appreciated by persons skilled in the art that the choice of expression vector may be determined by the choice of host cell. Thus, for expression of the polypeptides of the invention in *Lactococcus lactis* or *Lactobacillus johnsonii*, the nisin expression system could be used in which the polypeptide of the invention is expressed under the control of the promoter of the nisA operon using a background strain of *Lactococcus lactis* or *Lactobacillus johnsonii* which also expresses the nisR and nisK genes encoding a two component regulatory system. Under this system expression is positively regulated and induced by the provision of exogenous nisin (see de Ruyter at el., 1996, *Applied and Environmental Microbiology* 62:3662-3667, the disclosures of which are incorporated herein by reference).

In an alternative embodiment, the entire nisin biosynthesis gene cluster is provided within the same host cell, in which case the inducer is synthesised by that cell.

In a further alternative embodiment, the polypeptides of the invention may be expressed in *Lactococcus lactis* or *Lactobacillus johnsonii* under the control of the lactose catabolic operon, using either a plasmid-based or chromasomally integrated system (for example, see Payne et al., 1996, *FEMS Microbiology Letters* 136: 19-24 and van Rooijen et al., 1992, *Journal of Bacteriology* 174: 2273-2280, the disclosures of which are incorporated herein by reference).

As noted above, *Clostridium perfringens* is a cause for increasing concern due to its responsibility for severe infections both in humans and animals, especially poultry.

*Lactobacillus johnsonii* FI9785 is a poultry-isolated strain which has been shown to act as a competitive exclusion agent against *C. perfringens* in chickens. As well as acting as probiotics in their own right, lactic acid bacteria have also shown promise as delivery systems for the secretion of biologically active interleukins or peptidoglycan hydrolases. The promoter of the lantibiotic nisin A ($P_{nisA}$) is induced by nisin A via signal transduction using the two component regulatory system NisRK. This system has been exploited to develop gene expression systems in *Lactococcus lactis*, *Leuconostoc lactis* and *Lactobacillus helveticus*.

Hence, a fourth aspect of the invention provides a host cell which may comprise a nucleic acid molecule according to the second aspect of the invention or a vector according to the third aspect of the invention. In one embodiment, the host cell is a microbial cell, for example a bacterial cell. Preferably, the host cell is non-pathogenic.

For example, the host cell may be selected from the group consisting of cells of *Escherichia coli*, *Lactococcus* sp., *Bacteroides* sp., *Lactobacillus* sp., *Enterococcus* sp. and *Bacillus* sp.

In a preferred embodiment, the host cell is a cell of *Lactococcus lactis* (e.g., *L. lactis* FI10676, *L. lactis* FI15876, *L. lactis* FI17847 and *L. lactis* UKLc10).

In an equally preferred embodiment, the host cell is a cell of *Lactobacillus johnsonii* (e.g., *Lactobacillus johnsonii* FI9785 or its derivative strains, for example FI10744, FI10386 or FI10844).

Alternatively, the host cell may be a yeast cell, for example *Saccharomyces* sp.

A fifth aspect of the invention provides a method for producing a polypeptide of the invention which may comprise culturing a population of host cells which may comprise a nucleic acid molecule according to the second aspect of the invention or a vector according to the third aspect of the invention under conditions in which the polypeptide is expressed, and isolating the polypeptide therefrom.

A sixth aspect of the invention provides a pharmacological composition which may comprise:

(a) a polypeptide according to the first aspect of the invention;

(b) a nucleic acid molecule according to the second aspect of the invention;

(c) a vector according to the third aspect of the invention;

(d) a host according to the fourth aspect of the invention; and/or (e) a bacteriophage capable of expressing a polypeptide according to the first aspect of the invention and a pharmaceutically acceptable carrier, diluent or excipient.

As used herein, 'pharmaceutical composition' means a therapeutically effective formulation for use in the methods of the invention.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce, and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

In one embodiment of the invention, the pharmacological composition may comprise a polypeptide according to the first aspect of the invention.

The polypeptides can be formulated at various concentrations, depending on the efficacy/toxicity of the polypeptide being used. Preferably, the formulation may comprise the Polypeptide at a concentration of between 0.1 µM and 1 mM, more preferably between 1 µM and 100 µM, between 5 µM and 50 µM, between 10 µM and 50 µM, between 20 µM and 40 µM and most preferably about 30 µM. For in vitro applications, formulations may comprise similar concentrations of a polypeptide (however, it will be appreciated that higher concentrations may also be used).

Thus, the pharmaceutical formulation may comprise an amount of a polypeptide, or fragment, variant, fusion or derivative thereof, sufficient to inhibit at least in part the growth of cells of *Clostridium perfringens* in a patient who is infected or susceptible to infection with such cells. Preferably, the pharmaceutical formulation may comprise an amount of a polypeptide, or fragment, variant, fusion or derivative thereof, sufficient to kill cells of *Clostridium perfringens* in the patient.

It will be appreciated by persons skilled in the art that the polypeptides of the invention are generally administered in admixture with a suitable pharmaceutical excipient, diluent or carrier selected with regard to the intended route of administration and standard pharmaceutical practice (for example, see Remington: *The Science and Practice of Pharmacy*, 19th edition, 1995, Ed. Alfonso Gennaro, Mack Publishing Company, Pennsylvania, USA, the relevant disclosures in which document are hereby incorporated by reference).

For example, the polypeptides can be administered orally, buccally or sublingually in the form of tablets, capsules, ovules, elixirs, solutions or suspensions, which may contain flavouring or colouring agents, for immediate-, delayed- or controlled-release applications. The polypeptides may also be administered via direct injection (for example, into the GI tract).

Preferably, however, the polypeptides and pharmaceutical compositions thereof are for oral administration.

Suitable tablet formulations may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxyl-propylmethyl-cellulose (HPMC), hydroxy-propylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the polypeptides may be combined with various sweetening or flavouring agents, colouring matter or dyes, with emulsifying and/or suspending agents and with diluents such as water, ethanol, propylene glycol and glycerin, and combinations thereof.

The polypeptides can also be administered parenterally, for example, intravenously, intra-articularly, intra-arterially, intraperitoneally, intra-thecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the polypeptides will usually be from 1 to 1000 mg per adult (i.e. from about 0.015 to 15 mg/kg), administered in single or divided doses. For example, a dose of 1 to 10 mg/kg may be used, such as 3 mg/kg.

In an alternative embodiment of the invention, the pharmaceutical compositions do not comprise the polypeptide itself but instead may comprise a nucleic acid molecule capable of expressing said polypeptide. Suitable nucleic acid molecules, expression vectors, and host cells are described in detail above.

For example, a recombinant probiotic may be used (LAB strain, e.g., *Lactococcus lactis* or a *Lactobacillus* sp.).

In a further embodiment of the invention, the pharmaceutical compositions may comprise a bacteriophage capable of expressing a polypeptide according to the first aspect of the invention. For example, the wildtype bacteriophage φCP51 may be used to deliver a polypeptide according to the first aspect of the invention. Methods for performing such bacteriophage-based therapies are well known in the art (for example, see Watanabe et al., 2007, *Antimicrobial Agents & Chemotherapy* 51:446-452).

Thus, for treatment of bacterial infections described herein, the polypeptide of the invention may be administered as the cognate protein, as a nucleic acid construct, vector or host cell which expresses the cognate protein, as part of a living organism which expresses the cognate protein (including bacteriophages), or by any other convenient method known in the art so as to achieve contact of the lysin with its bacterial target, whether that be a pathogenic bacterium, such as *C. perfringens*, or another pathogen or potential pathogen, as further described herein.

Ideally, the protein is delivered to the GI tract in a protected form. This may be achieved by a wide variety of methods known in the art. For example, an appropriate dose of the lysin is microencapsulated in a form that survives the acidic conditions of the stomach, but which releases the protein as it enters the intestine. Delivery by a non-pathogenic microbe which survives GI tract transit, including but not limited to by *Lactococcus lactis*, *Lactobacillus johnsonii*, *Lactobacillus* sp., *Bifidobacterium* sp., *Bacillus* sp. or *Bacteroides*. Those skilled in the art are well aware of the options available for use of such means for GI tract delivery of active compounds such as the lysin disclosed herein. These means include intracellular production, secA secretion or secretion by means of another secretion pathway, and delivery by controlled lysis. Preferably the protein is not all released at one time, but is released increasingly as an administered bolus traverses through the GI tract. Alternatively, the lysin is introduced as part of a benign bacterium which expresses the lysin at the appropriate location or upon receipt of an appropriate signal in the GI tract. In a preferred embodiment disclosed herein, a non-pathogenic *Lactococcus* is engineered to express the CP51 lysin upon reaching a particular location in the GI tract. The expression signal may be defined by a pH sensitive promoter, or another means known in the art for this purpose.

Other means of delivery include the following:

(a) WO 2006/111553 (polyurea and other multilayer encapsulants);

(b) WO 2006/111570 and EP 1 715 739 (cyclodextrin encapsulation);

(c) WO 2006/100308 and EP 1 742 728 (for yeast and other microbial cell encapsulation technologies);

(d) U.S. Pat. No. 5,153,182, EP 1 499 183 and WO 03/092378; U.S. Pat. No. 6,831,070 (therapeutic gene product delivery by intestinal cell expression);

(e) U.S. Pat. No. 7,202,236 (pharmaceutical formulation for modified release);

(f) U.S. Pat. No. 5,762,904 (oral delivery of vaccines using polymerized liposomes, which may be modified to deliver the lysin of this invention), (g) U.S. Pat. No. 7,195,906 (*Bifidobacterium* which may be modified to express the lysin according to this invention); and (h) other means of delivery disclosed in the references cited therein, all of which are herein incorporated by reference for purposes of enabling those skilled in the art to utilize the present disclosure to achieve the novel methods of delivery and compositions according to the present invention.

Thus, in a preferred embodiment of the pharmacological compositions of the invention, the polypeptide, nucleic acid molecule encoding the same, etc. is microencapsulated (e.g., within a stable chemical envelope, such as cyclodextrin or a lipid bilayer, or within a living or non-living microbial cell, such as an engineered *Lactococcus* or *Lactobacillus* cell). In this way, the polypeptide, nucleic acid molecule, etc. may be protected against acidic conditions of stomach en route to its site of action in the GI tract.

A seventh aspect of the invention provides a polypeptide according to the first aspect of the invention, a nucleic acid according to the second aspect of the invention, a vector according to the third aspect of the invention, a host cell according to the fourth aspect of the invention or pharmacological composition according to the sixth aspect of the invention for use in medicine. Hence, the seventh aspect may be for use in a method for treatment of the human or animal body by surgery or therapy and/or diagnostic methods practised on the human or animal body.

An eighth aspect of the invention provides the use of a polypeptide according to the first aspect of the invention, a nucleic acid according to the second aspect of the invention, a vector according to the third aspect of the invention, a host cell according to the fourth aspect of the invention or pharmacological composition according to the sixth aspect of the invention, in the preparation of a medicament for killing and/or inhibiting/preventing the growth of microbial cells in a patient, wherein the microbial cells are selected from the group consisting of *Clostridium perfringens* cells and other bacterial cells susceptible to lysis with said endolysin.

A ninth aspect of the invention provides a polypeptide according to the first aspect of the invention, a nucleic acid according to the second aspect of the invention, a vector according to the third aspect of the invention, a host cell according to the fourth aspect of the invention or pharmacological composition according to the sixth aspect of the invention for use in killing and/or inhibiting/preventing the growth of microbial cells in a patient, wherein the microbial cells are selected from the group consisting of *Clostridium perfringens* cells and other bacterial cells susceptible to lysis with said endolysin.

A tenth aspect of the invention provides a method for killing and/or inhibiting/preventing the growth of microbial cells in a patient the method which may comprise administering to the patient a polypeptide according to the first aspect of the invention, a nucleic acid according to the second aspect of the invention, a vector according to the third aspect of the invention, a host cell according to the fourth aspect of the invention or pharmacological composition according to the sixth aspect of the invention, wherein the microbial cells are selected from the group consisting of *Clostridium perfringens* cells and other bacterial cells susceptible to lysis with said endolysin.

An eleventh aspect of the invention provides the use of a polypeptide according to the first aspect of the invention, a nucleic acid according to the second aspect of the invention, a vector according to the third aspect of the invention, a host cell according to the fourth aspect of the invention or pharmacological composition according to the sixth aspect of the invention in the preparation of a medicament for the treatment or prevention of a disease or condition associated with microbial cells in a patient, wherein the microbial cells are selected from the group consisting of *Clostridium perfringens* cells and other bacterial cells susceptible to lysis with said endolysin.

A twelfth aspect of the invention provides a polypeptide according to the first aspect of the invention, a nucleic acid according to the second aspect of the invention, a vector according to the third aspect of the invention, a host cell according to the fourth aspect of the invention or pharmacological composition according to the sixth aspect of the invention for use in the treatment or prevention of a disease or condition associated with microbial cells in a patient, wherein the microbial cells are selected from the group consisting of *Clostridium perfringens* cells and other bacterial cells susceptible to lysis with said endolysin.

A thirteen aspect of the invention provides a method for the treatment or prevention of a disease or condition associated with microbial cells in a patient the method which may comprise administering to the patient a polypeptide according to the first aspect of the invention, a nucleic acid according to the second aspect of the invention, a vector according to the third aspect of the invention, a host cell according to the fourth aspect of the invention or pharmacological composition according to the sixth aspect of the invention, wherein the microbial cells are selected from the group consisting of *Clostridium perfringens* cells and other bacterial cells susceptible to lysis with said endolysin.

By "a disease or condition associated with microbial cells in a patient" Applicants include diseases and conditions arising from or antagonised by infection of a patient with *Clostridium perfringens*. Such diseases and conditions include food poisoning, gas gangrene (Myonecrosis) and necrotic endocarditis (NE).

In one embodiment of the above method/use aspects of the invention, the polypeptide having the cell lysing activity of an endolysin from a bacteriophage of *Clostridium perfringens* is a polypeptide according to the first aspect of the invention, wherein the microbial cells are selected from the group consisting of *Clostridium perfringens* cells and other bacterial cells susceptible to lysis upon contact with a polypeptide of SEQ ID NO: 1 (see Table 1, below).

Preferably, the microbial cells may comprise or consist of *Clostridium perfringens* cells. Thus, the polypeptides having the cell lysing activity of an endolysin from a bacteriophage of *Clostridium perfringens* may be used to treat or prevent diseases and conditions associated with infection with *Clostridium perfringens* cells (such as food poisoning, gas gangrene (Myonecrosis) and necrotic endocarditis).

Persons skilled in the art will further appreciate that the uses and methods of the present invention have utility in both the medical and veterinary fields. Thus, the medicaments may be used in the treatment of both human and non-human animals (such as horses, cows, dogs and cats). Hence, the methods and uses may be for use in an organism belonging to a taxonomic superclass or class selected from the group consisting of Chondrichthyes (cartilaginous fish), Osteichthyes (bony fish), Actinopterygii (ray-finned bony fish), Sarcopterygii (lobe-finned fish), Tetrapoda (four-limbed vertebrates), Amphibia (amphibians), Reptilia (reptiles), Aves (birds) and Mammalia (mammals).

In one preferred embodiment, the taxonomic class is Aves (birds). Thus, the polypeptides of the invention may be for use in poultry (for example, selected from the group consisting of chicken, duck, goose, ostrich, pigeon, turkey, pheasant, guinea fowl, partridge and quail).

In another preferred embodiment, the taxonomic class is Mammalia (mammals), for example, the mammal may be selected from the group consisting of alpaca, banteng, bison, camel, cat, cattle, deer, dog, donkey, gayal, goat, guinea pig, horse, llama, mule, pig, rabbit, reindeer, sheep, water buffalo, yak and human.

Most preferably, however, the polypeptides of the invention are for use in poultry.

By 'treatment' Applicants include both therapeutic and prophylactic treatment of a subject (or patient). In one embodiment, the uses and methods of the invention are for the treatment of an existing disease or condition. Alternatively or additionally, the uses and methods of the invention may be for prophylaxis. The term 'prophylactic' or 'prophylaxis' is used to encompass the use of a polypeptide or formulation described herein which either prevents or reduces the likelihood of infection with *Clostridium perfringens* in a patient or subject. The prophylaxis may be primary prophylaxis (i.e., to prevent the development of a disease) or secondary prophylaxis (where the disease has already developed and the patient is protected against worsening of this process). Preferably, the prophylaxis is primary prophylaxis.

As discussed above, the term 'effective amount' is used herein to describe concentrations or amounts of polypeptides according to the present invention which may be used to produce a favourable change in a disease or condition treated, whether that change is a remission, a favourable physiological result, a reversal or attenuation of a disease state or condition treated, the prevention or the reduction in the likelihood of a condition or disease state occurring, depending upon the disease or condition treated.

In one embodiment, the polypeptide according to the first aspect of the invention, nucleic acid according to the second aspect of the invention, vector according to the third aspect of the invention, host cell according to the fourth aspect of the invention or pharmacological composition according to the sixth aspect of the invention is administered in a single dose. Alternatively, the polypeptide, nucleic acid, vector, host cell, bacteriophage or pharmacological composition is administered as a plurality of doses (for example, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more doses).

The polypeptide, nucleic acid, vector, host cell, bacteriophage or pharmacological composition is preferably administered at a frequency sufficient to maintain a continuous presence of the polypeptide according to the first aspect of the invention in the gastrointestinal (GI) tract of the subject. Preferably, the dose and dosage frequency is sufficient to prevent occurrence or recurrence of a disease or condition associated with microbial cells in a subject. Preferably, the dose and dosage frequency is sufficient to prevent occurrence or recurrence of growth impedance associated with microbial cells in a subject (e.g., *C. perfringens*).

In one embodiment, the uses and methods of the invention a host cell or pharmacological composition which may comprise a host cell is used to deliver the polypeptide of the first aspect of the invention (preferably a host cell).

It will be appreciated that the medicaments described herein may be administered to a subject in combination with one or more additional therapeutic agents.

For example, the medicaments described herein may be administered to a subject in combination with:

(a) one or more conventional antibiotic treatments (such as beta-lactams, aminoglycosides and/or quinolones);

(b) one or more additional lysins, or nucleic acid molecules, vectors, host cell or bacteriophage capable of expressing the same;

(c) one or more holins (such as the holing of φCP51: MENIFDYLKMGIVAIGTLFTWLLGAWDTPLVILIV-LMALDYITGITKGYVNKDLSSNI GLKGIARK-GVIFTILIVAVMLDRLLNTGNWIFRTLVCYFYIA-NEGISIIENASELGVPVP SKLKNALIQLKEDKEDHKKL [SEQ ID NO: 3]), or nucleic acid molecules, vectors, host cell or bacteriophage capable of expressing the same;

(d) one or more [antibiotics, or nucleic acid molecules, vectors, host cell or bacteria capable of expressing the same; and/or (e) a therapy to neutralise the toxins released upon bacterial lysis of *Clostridium perfringens* cells within the gut. Suitable neutralising therapies may include antibodies (see Babcock et al., 2006, *Infect. Immun.* 74:6339-6347) and toxin-absorbing agents such as tolevamer (see Barker et al., 2006, *Aliment. Pharmacol. Ther.* 24:1525-1534).

A further aspect of the invention provides the use of a polypeptide having the cell lysing activity of an endolysin from a bacteriophage of *Clostridium perfringens*, or a nucleic acid molecule, vector, host cell or bacteriophage capable of expressing the same, for killing and/or inhibiting/preventing the growth of microbial cells in vitro and/or ex vivo, wherein the microbial cells are selected from the group consisting of *Clostridium perfringens* cells and other bacterial cells susceptible to lysis with said endolysin. For example, said polypeptides having endolysin activity may be used to clean surfaces, such as those in hospitals, kitchens, etc., which may be susceptible to contamination with such bacterial cells.

Preferably, the polypeptide having the cell lysing activity of an endolysin from a bacteriophage of *Clostridium perfringens* is a polypeptide according to the first aspect of the invention, wherein the microbial cells are selected from the group consisting of *Clostridium perfringens* cells and other bacterial cells susceptible to lysis upon contact with a polypeptide of SEQ ID NO: 1 (see Table 1, below). For example, the microbial cells may comprise or consist of *Clostridium perfringens* cells. Most preferably, the microbial cells may comprise or consist of cells of *Clostridium perfringens* NCTC 3110 and/or NCTC 8238.

A further aspect of the present invention provides a kit for detecting the presence of microbial cells in a sample, the kit which may comprise a polypeptide having the cell lysing activity and/or cell binding specificity of an endolysin from a bacteriophage of *Clostridium perfringens*, or a nucleic acid molecule, vector, host cell or bacteriophage capable of expressing the same, wherein the microbial cells are selected from the group consisting of *Clostridium perfringens* cells and other bacterial cells susceptible to lysis with said endolysin.

In a preferred embodiment, the polypeptide having the cell lysing activity of an endolysin from a bacteriophage of *Clostridium perfringens* is a polypeptide according to the first aspect of the invention, wherein the microbial cells are selected from the group consisting of *Clostridium perfringens* cells and other bacterial cells susceptible to lysis upon contact with a polypeptide of SEQ ID NO: 1 (see Table 1, below). For example, the microbial cells may comprise or consist of *Clostridium perfringens* cells. Most preferably, the microbial cells may comprise or consist of cells of *Clostridium perfringens* NCTC 3110 and/or NCTC 8238.

In a further embodiment of the kits of the invention, the polypeptide having the cell lysing activity of an endolysin from a bacteriophage of *Clostridium perfringens* is immobilised on a suitable surface, such as the surface of a multi-well plate.

The kits may be used in conjunction with any suitable sample of cells, such as tissue samples, cell culture samples and samples of cells derived from swabs (e.g., taken from a surface to be tested for contamination with microbial cells).

Optionally, the kit further may comprise a negative control sample (which does not contain cells of the type to be tested for, e.g., *Clostridium perfringens* cells) and/or a positive control sample (which contains cells of the type to be tested for).

Related aspects of the invention provide:

(a) the use of a polypeptide having the cell wall binding activity and/or cell lysing activity of an endolysin from a bacteriophage of *Clostridium perfringens*, or a nucleic acid molecule, vector, host cell or bacteriophage capable of expressing the same, in the preparation of a diagnostic agent for a disease or condition associated with microbial cells selected from the group consisting of *Clostridium perfringens* cells and other bacterial cells susceptible to lysis with said endolysin;

(b) the use of a polypeptide having the cell wall binding activity and/or cell lysing activity of an endolysin from a bacteriophage of *Clostridium perfringens*, or a nucleic acid molecule, vector, host cell or bacteriophage capable of expressing the same, for the diagnosis of a disease or condition associated with microbial cells selected from the group consisting of *Clostridium perfringens* cells and other bacterial cells susceptible to lysis with said endolysin;

(c) the use of a polypeptide having the cell wall binding activity and/or cell lysing activity of an endolysin from a bacteriophage of *Clostridium perfringens*, or a nucleic acid molecule, vector, host cell or bacteriophage capable of expressing the same, for detecting the presence of microbial cells in a sample in vitro and/or ex vivo, wherein the microbial cells selected from the group consisting of *Clostridium perfringens* cells and other bacterial cells susceptible to lysis with said endolysin; and (d) a method for the diagnosis of a disease or condition associated with microbial cells in a patient, the method which may comprise contacting a cell sample from a patient to be tested with a polypeptide having the cell wall binding activity and/or cell lysing activity of an endolysin from a bacteriophage of *Clostridium perfringens*, or a nucleic acid molecule, vector, host cell or bacteriophage capable of expressing the same, and determining whether the cells in the sample have been lysed thereby, wherein the microbial cells are selected from the group consisting of *Clostridium perfringens* cells and other bacterial cells susceptible to lysis with said endolysin.

In one embodiment of the above defined uses and methods of the invention, the polypeptide having the cell lysing activity of an endolysin from a bacteriophage of *Clostridium perfringens* is a polypeptide according to the first aspect of the invention, wherein the microbial cells are selected from the group consisting of *Clostridium perfringens* cells and other bacterial cells susceptible to lysis upon contact with a polypeptide of SEQ ID NO: 1 (see Table 1, below). Preferably, the microbial cells may comprise or consist of *Clostridium perfringens* cells. Thus, the polypeptides having the cell lysing activity of an endolysin from a bacteriophage of *Clostridium perfringens* may be used to diagnose diseases and conditions associated with infection with *Clostridium perfringens* cells (such as food poisoning, gas gangrene (Myonecrosis) and necrotic endocarditis (NE)). Most preferably, the microbial cells may comprise or consist of cells of *Clostridium perfringens* NCTC 3110 and/or NCTC 8238.

In such diagnostic uses and methods, lysis of cells may be detected using methods well known in the art. For example, levels of ATP may be measured as an indicator of cell lysis.

In an alternative embodiment of the above defined uses and methods of the invention, the polypeptide may comprise or consist of the cell wall binding domain of an endolysin from a bacteriophage of *Clostridium perfringens*. To permit detection, such a polypeptide may be fused to magnetic beads or used as a fusion protein which may comprise a suitable reporter (for example, green fluorescent protein).

Such diagnostic approaches are well established for endolysins from other systems, such as *Listeria* endolysins (for example, see Loessner et al., 2002, *Mol Microbiol* 44, 335-49; Kretzer et al., 2007, *Applied Environ. Microbiol.* 73:1992-2000, the disclosures of which are incorporated herein by reference; suitable assays are also available commercially, for example from Profos, Germany.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example A—Complete Genome Sequence of ϕCP51, a Temperate Bacteriophage of *Clostridium Perfringens*

During sequencing of the genome of *Clostridium perfringens* strain 5147-97, a putative prophage was identified located within a gene for a proposed flavodoxin oxidoreductase. Mitomycin C induction of this strain released a bacteriophage whose morphological features examined by electron microscopy indicated it belonged to the family Siphoviridae. To determine the ends of the prophage, PCR was performed using primers facing outwards from the proposed end genes. This confirmed the presence of a circularised genome in PEG-precipitated bacteriophage particles. The 39108 bp genome includes 50 predicted open reading frames (ORFs), including two which may affect sporulation, and two predicted tRNAs.

*C. perfringens* is a Gram-positive, anaerobic, spore-forming bacterium whose production of toxins leads to debilitating infections in both humans and animals. Conditions include food poisoning, gas gangrene, non-foodborne gastrointestinal infections and necrotic enteritis (NE) [7]. In poultry, NE has a significant impact on health, productivity and the carriage of pathogenic bacteria in the food chain [17]. A range of novel approaches are being explored to control *C. perfringens* and the use of bacteriophages or their cell lytic endolysins may provide alternatives to conventional antimicrobials [9]. The increasing collection of *C. perfringens* phages presents opportunities both for control and for a better understanding of the relationship between the phage and the host [6, 8, 13, 18-20].

A single prophage sequence ϕCP51 was identified within the genome of *C. perfringens* 5146-97, a type A strain isolated from turkey (kindly provided by M. Brett, HPA, UK). Library construction and sequencing on the Illumina GAIIX was performed by TGAC (Norwich, UK). Reads were assembled with ABySS [15] and contigs were extended using CAP3 [5] then annotated by RAST [2]. Bacteriophage particles were induced with mitomycin C, harvested and assayed as described previously [14]. Filtered mitomycin C-induced supernatants were tested against 25 *C. perfringens* strains but no plaque formation was observed. However, phage particles were observed by electron microscopy of PEG-precipitated particles [11] which had been negatively stained in saturated uranyl acetate (FIG. 1). This revealed a phage with an icosahedral head (diameter 55±2 nm) and a long, flexible tail (length 160±5 nm) with transverse striation. These characteristics indicate that the phage probably belongs to the Siphoviridae family of the order Caudoviridales. A number of sequenced *C. perfringens* phages show a similar morphology (e.g. ϕ3626 [20], ϕS9, S63 [6], ϕCP39O and ϕCP26F [13]).

The ϕCP51 prophage genome was located between 2 host genome coding sequences which were annotated as fragments of a flavodoxin reductase. Two homologous 11 bp core regions (CTGGACATGCT [SEQ ID NO: 4]) were identified at the end of the first fragment and the beginning of the second, representing potential attachment sites. In silico removal of the prophage sequence and one of the core regions reconstituted a sequence which when translated showed 100% homology to complete putative FAD dependent oxidoreductases from *C. perfringens* genomes SM101 and D str. JGS1721. Similarly, circularization of the prophage at the core region joined the first and last ORFs in the prophage to generate a single ORF with homology to a recombinase, giving a final bacteriophage genome size of 39108 bp.

To confirm the extent of the phage genome, outward-facing primers were designed from the first (CP51_R1, 5-ATAGATCTTATAACGTCTCTCTTG [SEQ ID NO: 5]) and last (CP51_F2, 5-TCACCTATAGTTTTATTTGGAA [SEQ ID NO: 6]) prophage ORFs to cover the predicted circularized product of 326 bp. Using GoTaq (Promega), a product was successfully amplified from PEG-precipitated mitomycin C-induced supernatant and sequencing confirmed the expected recircularisation point.

Phage ORF locations and domain identifications were confirmed using Artemis [10] with BlastP searches [1] using the NCBI database. Start sites were selected as the best match to the consensus ribosome binding site sequence AGGAGG [SEQ ID NO: 7] 5 to 13 nt from the start codon. ATG was the most common start codon, but there were also incidences of alternative start codons TTG (ORFs 22, 30, 47), GTG (ORFs 17, 32, 49) and ATA (ORF 19). The G+C content of 28% matches that of the host bacterial genome.

BlastP analyses indicate that most of the ORFs show similarity to proteins from bacterial genomes rather than from phages, possibly matching proteins from other prophages. The organisation of modules was similar to that seen in ϕ3626 [20]. The first 25 ORFs, covering the proposed structural and lysis proteins, almost exclusively match *C. perfringens* sequences (FIG. 2, Table 2). These include two terminase subunit genes (ORFs 1, 2), a portal protein (ORF 3), capsid proteins (ORFs 4, 9, 13, 15), a putative head-tail connector protein (ORF 11) and two large proteins representing the tape measure protein (ORF 18) and a predicted tail protein (ORF 22). Unusually, the holin and lysin genes are separated by a hypothetical protein, ORF24. The presence of a gene between the holin and lysin is uncommon but this arrangement was also noted in the *C. difficile* bacteriophage ϕC2 [4]. The lysin was identified as a putative N-acetylmuramoyl-L-alanine amidase, with homology to domains associated with cell lysis and binding. The lysin is followed by 3 hypothetical proteins which show no similarity to sequences from *C. perfringens*. They are followed by 3 ORFs, transcribed in the opposite direction, which show homology to a resolvase from *Clostridium botulinum* and two repressors respectively, forming the proposed lysogeny module. The resolvase gene (ORF 29) includes the attP site 1696 bp into its 1968 bp sequence and so is divided in the prophage but re-constituted in the circularised form. The rest of the genome contains genes which are predicted to function in DNA replication and modification and is again dominated by proteins with similarity to *C. perfringens* but with occasional ORFs from different backgrounds. This module has two further predicted genes for recombinases (ORF 49, 50) in addition to the resolvase located in the lysogeny module; ϕ3626 also has a recombinase in this location. There are also two ORFs predicted to be involved in the control of sporulation—a sigma factor (ORF 37) and a transcriptional regulator SpoIlID (ORF 43). Sporulation proteins have been identified in other phages of *C. perfringens [*18, 20] and lysogenisation of *C. perfringens* with the temperate phage s9 had a positive effect on sporulation[16]; the incidence of such genes in phage genomes may represent an interesting evolutionary strategy.

Two tRNAs (Tyr-ATA and Ser-GCT) were identified by RAST analysis; tRNAs in phage genomes have been associated with codon usage, corresponding to the codons that are highly used by phage genes and rare in the host genome [3]. However, analysis of the codon usage in ϕCP51 and the host genome showed no difference.

As more bacterial genomes are sequenced, there will be a continued opportunity for the identification of prophages, which can be used to add knowledge to phage biology or for isolation of phage encoded enzymes [12]. Although Applicants failed to demonstrate plaque formation, the ϕCP51 lysin is active (see Examples, below) indicating that the phage might be lytic on a suitable host. However there is a possibility that the phage is not able to progress through the life cycle due to unidentified defects within the genome.

Nucleotide Sequence Accession Number

The complete genome sequence of ϕCP51 was deposited in the GenBank database under accession number KC237729.

REFERENCES

1. Altschul S F, Madden T L, Schaffer A A, Zhang J, Zhang Z, Miller W, Lipman D J (1997) Gapped BLAST and 1. PSI-BLAST: a new generation of protein database search programs. Nucleic Acids Res 25:3389-402
2. Aziz R K, Bartels D, Best A A, DeJongh M, Disz T, Edwards R A, Formsma K et al (2008) The RAST Server: rapid annotations using subsystems technology. BMC Genomics 9:75
3. Bailly-Bechet M, Vergassola M, Rocha E (2007) Causes for the intriguing presence of tRNAs in phages. Genome Res 17:1486-95
4. Goh S, Ong P F, Song K P, Riley T V, Chang B J (2007) The complete genome sequence of *Clostridium difficile* phage φC2 and comparisons to φCD119 and inducible prophages of CD630. Microbiology 153:676-85
5. Huang X, Madan A (1999) CAP3: A DNA sequence assembly program. Genome Res 9:868-77
6. Kim K P, Born Y, Lurz R, Eichenseher F, Zimmer M, Loessner M J, Klumpp J (2012) Inducible *Clostridium perfringens* bacteriophages φS9 and φS63: Different genome structures and a fully functional sigK intervening element. Bacteriophage 2:89-97
7. Lindstrom M, Heikinheimo A, Lahti P, Korkeala H (2011) Novel insights into the epidemiology of *Clostridium perfringens* type A food poisoning. Food Microbiol 28:192-8
8. Morales C A, Oakley B B, Garrish J K, Siragusa G R, Ard M B, Seal B S (2012) Complete genome sequence of the podoviral bacteriophage φCP24R, which is virulent for *Clostridium perfringens*. Arch Virol 157:769-72
9. O'Flaherty S, Ross R P, Coffey A (2009) Bacteriophage and their lysins for elimination of infectious bacteria. FEMS Microbiol Rev 33:801-19
10. Rutherford K, Parkhill J, Crook J, Horsnell T, Rice P, Rajandream M A, Barrell B (2000) Artemis: sequence visualization and annotation. Bioinformatics 16:944-5
11. Sambrook J, Fritsch, E F, and Maniatis, T (1989) Molecular Cloning: A Laboratory Manual, 2nd ed. Cold Spring Harbor Lab. Press, Plainview, N.Y.
12. Schmitz J E, Ossiprandi M C, Rumah K R, Fischetti V A (2011) Lytic enzyme discovery through multigenomic sequence analysis in *Clostridium perfringens*. Appl Microbiol Biotechnol 89:1783-95
13. Seal B S, Fouts D E, Simmons M, Garrish J K, Kuntz R L, Woolsey R, Schegg K M et al (2011) *Clostridium perfringens* bacteriophages φCP39O and φCP26F: genomic organization and proteomic analysis of the virions. Arch Virol 156:25-35
14. Sell T L, Schaberg D R, Fekety F R (1983) Bacteriophage and bacteriocin typing scheme for *Clostridium difficile*. J Clin Microbiol 17:1148-52
15. Simpson J T, Wong K, Jackman S D, Schein J E, Jones S J, Birol I (2009) ABySS: a parallel assembler for short read sequence data. Genome Res 19:1117-23
16. Stewart A W, Johnson M G (1977) Increased numbers of heat-resistant spores produced by two strains of *Clostridium perfringens* bearing temperate phage s9. J Gen Microbiol 103:45-50
17. Van Immerseel F, Rood J I, Moore R J, Titball R W (2009) Rethinking our understanding of the pathogenesis of necrotic enteritis in chickens. Trends Microbiol 17:32-6
18. Volozhantsev N V, Oakley B B, Morales C A, Verevkin V W, Bannov V A, Krasilnikova V M, Popova A V et al (2012) Molecular characterization of podoviral bacteriophages virulent for *Clostridium perfringens* and their comparison with members of the Picovirinae. PLoS One 7:e38283
19. Volozhantsev N V, Verevkin V V, Bannov V A, Krasilnikova V M, Myakinina V P, Zhilenkov E L, Svetoch E A et al (2011) The genome sequence and proteome of bacteriophage φCPV1 virulent for *Clostridium perfringens*. Virus Res 155:433-9
20. Zimmer M, Scherer S, Loessner M J (2002) Genomic analysis of *Clostridium perfringens* bacteriophage φ3626, which integrates into guaA and possibly affects sporulation. J Bacteriol 184:4359-68

Example B—Expression and Delivery of an Endolysin to Combat *Clostridium Perfringens*

BACKGROUND

*Clostridium perfringens* is a cause for increasing concern due to its responsibility for severe infections both in humans and animals, especially poultry. To find new control strategies to treat *C. perfringens* infection, Applicants investigated the activity and delivery of a bacteriophage endolysin. Applicants identified a new endolysin, designated CP51L, which shows similarity to an N-acetylmuramoyl-L-alanine amidase domain but not to other *C. perfringens* endolysins whose activity has been demonstrated in vitro. The cp51 1 gene was cloned and expressed in *Escherichia coli* and the gene product demonstrated lytic activity against all 25 *C. perfringens* strains tested. A probiotic strain of *Lactobacillus johnsonii* FI9785 was engineered to produce a system for delivery of the endolysin to the gastrointestinal tract. The integration of the nisRK two component regulatory system from the *Lactococcus lactis* nisin A biosynthesis operon into the chromosome of *L. johnsonii* allowed constitutive expression of the endolysin under the control of the nisA promoter ($P_{nisA}$), while the use of a signal peptide (SLPmod) successfully secreted the active endolysin to the surrounding media. The high specificity and activity of the endolysin suggest it may be developed as an effective tool to enhance the control of *C. perfringens* by *L. johnsonii* in the gastrointestinal tract.

Materials and Methods

Bacterial Strains and Growth Conditions

*C. perfringens* strains listed in Table 1 were obtained from the NCTC (HPA, London, UK), or from in-house culture collections (IFR, Norwich, UK). *C. perfringens* 5416-97 is a Type A strain (11). Strains were maintained in Robertson's cooked-meat medium (SGL) at room temperature and were grown anaerobically at 37° C. in brain heart infusion broth (BHI, Oxoid) supplemented with vitamin K [50 mg/l], hemin [5 mg/l], resazurin [1 mg/l], and L-cysteine[0.5 g/l]), termed BHI+C. *E. coli* strains were grown in L broth with shaking at 37° C. and *L. johnsonii* strain FI9785 (20) and derivatives were grown in MRS broth (Oxoid) at 37° C. Commensal, environmental and clostridial strains were obtained from IFR culture collections, the DSMZ (Braunschweig, Germany) or the NCIMB (Aberdeen, UK), and were grown as recommended by DSMZ or in BHI+C. The following strains were used for lysin specificity tests: *Anaerococcus hydrogenalis* DSMZ 7454, *Bacillus amyloliquefaciens* 0880, *Bacillus cereus* NCIMB 11796, *Bacillus subtilis* ATCC 6633, *Bifidobacterium adolescentis* DSMZ 20083, *Bifidobacterium angulatum* DSMZ 20098, *Bifidobacterium bifidum* DSMZ 20082, *Bifidobacterium longum* DSMZ 20219, *Bifidobacterium pseudocatenulatum* DSMZ 20438, *Clostridium acetobutylicum* BL75141, *Clostridium bifermentans* NCTC 13019, *Clostridium beijerinckii* NCIMB 8052, *Clostridium cellobioparum* DSMZ 1351, *Clostridium coccoides* NCTC 11035, *Clostridium colinum* DSMZ 6011, *Clostridium difficile* NCTC 11204,

*Clostridium innocuum* DSMZ 1286, *Clostridium leptum* DSMZ 753, *Clostridium nexile* DSMZ 1787, *Clostridium ramosum* DSMZ 1402, *Clostridium sordellii* NCTC 13356, *Clostridium sporogenes* ATCC 17886, *Clostridium tyrobutyricum* NCIMB 9582, *Enterococcus faecalis* FI10734, *Enterococcus hirae* FI10477, *Eubacterium barkeri* DSMZ 1223, *Lactobacillus casei* FI10736, *L. johnsonii* FI9785, *Lactobacillus plantarum* FI08595, *Lactobacillus rhamnosus* FI10737, *Lactococcus lactis* MG1363, *Leuconostoc mesenteroides* subsp. *mesenteroides* ATCC 8293, *Listeria innocua* NCTC 11288, *Listeria ivanovii* NCTC 11007, *Micrococcus luteus* FI10640, *Pediococcus pentosaceus* FI10642, *Pediococcus acidilactici* FI10738, *Salmonella enterica* serovar Typhimurium FI10739, *Salmonella enterica* serovar Enteritidis FI10113, *Staphylococcus aureus* FI10139.

Endolysin CP51L Analysis and Subcloning

The endolysin sequence is available in the φCP51 genome nucleotide sequence, accession number KC237729. Endolysin amino acid similarities and conserved domains were determined using Blastp (1) and the NCBI non-redundant protein sequences database. Amino acid alignments were performed using the ClustalW algorithm in Vector NTI (Invitrogen).

Genomic DNA was extracted from cells of *C. perfringens* 5416-97 (grown to mid-exponential phase) using the Genomic DNA extraction kit with a Genomic Tip 20/G column (Qiagen) as described by the manufacturer, with the addition of 50 U mutanolysin (Sigma) to aid cell lysis. The putative endolysin gene cp51l was amplified from genomic DNA using Phusion DNA polymerase (Finnzymes). To facilitate cloning into the NdeI and XhoI sites of expression vector pET15b (Novagen), primers were designed to incorporate an NdeI site at the initiating methionine codon CP51L_NDE (5'—GAATGT$\underline{CA}$TATGTATATAAATCAATCA-3' [SEQ ID NO: 8], altered nucleotides underlined throughout) and a XhoI site downstream of the stop codon CP51L_XHO (5'-A$\underline{CTC}$ $\underline{G}$AGGTGGGATAATTCCTACC-3' [SEQ ID NO: 9]). Due to the presence of an internal NdeI site, internal primers were designed to create a 1 bp substitution (T771C) without changing the resulting amino acid sequence. Primer CP51L_GTG (5'-TATTGCAT$\underline{G}$TGGTAGTCAAAAGAT-3' [SEQ ID NO: 10]) was used in conjunction with CP51L_NDE and primer CP51L_CAC (5'-TTGACTAC-$\underline{C}$ACATGCAATATAAAAATG-3' [SEQ ID NO: 11]) was paired with CP51L_XHO, then the two products were spliced and amplified using overlap extension PCR with primers CP51L_NDE and CP51L_XHO. The splice product was restricted with NdeI and XhoI (New England Biolabs) and cloned into restricted pET15b that had been dephosphorylated with Antarctic Phosphatase (New England Biolabs) using Fastlink ligase (Epicentre). Ligation products were transformed into chemically competent *E. coli* TOP10 cells (Invitrogen) and transformants were selected with ampicillin (100 μg/ml). After confirmation by sequencing, construct pET15b-cp51l and the empty control vector pET15b were transformed for expression into chemically competent *E. coli* BL21(DE3) cells (Invitrogen).

An endolysin expression and secretion construct was produced in pUK200 (47) placing the endolysin coding sequence downstream of the signal peptide SLPmod (7) and a 6×His tag, all under the control of the promoter $P_{nisa}$ (pUK200-slpmod-6×His-cp51l). Ligation products were transformed into electrocompetent *E. coli* MC 1022, selected with chloramphenicol (15 μg/ml) and confirmed by sequencing. To provide the two-component regulatory system required for $P_{nisA}$ controlled expression, the nisRK genes from *Lactococcus lactis* FI5876 (5) were inserted into the chromosome of *L. johnsonii* FI9785 using the thermosensitive pG+host9 vector (27). An integration region was amplified from *L. johnsonii* FI9785 genomic DNA and the resulting 1033 bp product was cloned into the blunt-ended SpeI site of pG+host9 (creating plasmid pFI2657). A 2.4 kb region encoding nisRK was amplified from the genome of *L. lactis* FI5876 using the primer pair nisRK_F (5'-CCCGGGAGAATCTTAAAGAGTCTAGGG-3' [SEQ ID NO: 12]) and nisRK R (5'-AAAAAGTAATCCTTAGA-GATTAC-3' [SEQ ID NO: 13]) and cloned into a blunt-ended BstEII site located within the integration region of pFI2657, creating pFI2652. Subsequently, *L. johnsonii* FI9785 was transformed with pFI2652 and the nisRK sequences were integrated into the chromosome by gene replacement (27) using 30° C. as the permissive temperature and 42° C. as the non-permissive temperature, to create the nisRK-carrying strain FI10744. The lysin expression construct and the control vector pUK200 were transformed into electrocompetent *L. johnsonii* FI10744 as described (14) and positive transformants were selected using chloramphenicol (7.5 μg/ml) to give the endolysin delivery strain FI10744-L and the vector control FI10744-V.

Protein Expression, Analysis, and Partial Purification

Crude protein extracts were produced from IPTG-induced *E. coli* BL21(DE3) cells containing pET15b-cp51l or pET15b in either NP buffer (20 mM sodium phosphate buffer pH 6.5), TN buffer (20 mM Tris-HCl, 50 mM NaCl pH 7.5), or elution buffer (EB, 50 mM sodium phosphate, 300 mM NaCl, 250 mM imidazole pH 8) by bead beating as previously described (29). His-CP51L was partially purified using the nickel-nitrilotriacetic acid (Ni-NTA) Fast Start kit (Qiagen). *L. johnsonii* cells grown to mid-exponential phase were incubated for 2 h with or without nisin (10 ng/ml). Cells were harvested by centrifugation for 10 min at 2,500×g and 4° C. and the cell pellet was frozen while the supernatant was concentrated 20-fold using Amicon columns (Ultra-4 ultracell-30 k, Millipore) or 166-fold by shaking for 5 min after the addition of an equal volume of 100% ethanol pre-cooled to −80° C., followed by centrifugation for 30 min at 10,000×g and 4° C. The resulting pellet was freeze-dried in liquid nitrogen prior to resuspension in EB. Crude cell extracts were produced by bead beating in EB as with *E. coli*. Protein quantification, electrophoresis and Western blot analysis with a His Tag® monoclonal antibody (Novagen) were all performed as described previously (29).

Lysis Assays

The lysis of *C. perfringens* NCTC 3110 cells resuspended in phosphate buffered saline (PBS) was assessed by turbidity reduction assay as previously described (29) using the appropriate buffer controls. Cells for lysis assays were either used immediately after harvest ('fresh') or were flash frozen in liquid nitrogen and stored at −20° C. until use (frozen). Hen egg white lysozyme (Sigma) was used as a positive control at 500 U per 300 μl assay. The activity profile of crude protein extracted in NP buffer under various pH conditions was examined by adjusting the PBS to pH values between 4.5 and 8.5, while activity in different media was assessed by replacing the PBS with BHI+C or chemostat medium, a complex medium used for in vitro fermentations (CM: peptone water 2 g/l (Oxoid), yeast extract 2 g/l (Oxoid), NaCl 0.1 g/l, $K_2HPO_4$ 0.04 g/l, $KH_2PO_4$ 0.04 g/l, $MgSO_4.7H_2O$ 0.01 g/l, $C_aCl_2.6H_2O$ 0.01 g/l, $NaHCO_3$ 2 g/l, Tween 80 2 ml, hemin 0.02 g/l dissolved in 400 μL, 1 M NaOH, vitamin K1 10 μl of 5% v/v aqueous solution, cysteine HCl 0.5 g/l, bile salts 0.5 g/l, 1% glucose all from Sigma, (28)). Activity against different species was assessed using 10 μg of Ni-NTA partially purified protein during a 1 h incubation. The endolysin activity of crude protein extracts and concentrated culture supernatants from the engineered *L. johnsonii* strains was measured by plate assay as described previously (41). Briefly, *C. perfringens* cells were grown to stationary phase in 100 ml BHI broth, autoclaved, pelleted by centrifugation then resuspended in 1 ml of PBS and added to 100 ml of PBS with 1% agar at 55° C. After pouring into plates, small holes were punched into the seeded agar and 10 μl of protein extract (equivalent to 30 μg) or 20 μl of concentrated supernatants were loaded into the wells and the plates were then incubated for 24 h at 37° C. To demonstrate lytic activity from growing colonies, *C. perfringens* cells were processed in the same way then incorporated into plates containing MRS agar with 7.5 μg/ml chloramphenicol. Overnight cultures of FI10744-L and FI10744-V were subsequently streaked onto these plates and the plates were incubated for 1-3 d at 37° C.

*C. perfringens* NCTC 3110 viability assays were performed by adding 166 μg of Ni-NTA partially purified CP51L protein to 5 ml of pre-reduced BHI+C under anaerobic conditions. The protein was added to the media either immediately before *C. perfringens* inoculation (20 μl of a fresh overnight culture) or during the early exponential phase of growth (optical density [$OD_{600}$] ca. 0.3). To determine *C. perfringens* viability, samples were taken every 2 h for 8 h and serially diluted in PBS before being plated onto BHI agar and incubated for 24 to 48 h at 37° C. Results were calculated as the total number of bacteria from triplicate counts.

Results

Characterisation of the CP51L Endolysin

The cp51l gene was identified previously within the genome of a mitomycin C-inducible prophage of *C. perfringens* 5416-97 (ϕCP51, see Examples, below). Blastp analysis of CP51L identified 2 regions with similarity to conserved domains separated by a central section (FIG. 3). In the N-terminal part of the protein there is an area with similarity to domains associated with cell wall binding and lysis, including the peptidoglycan recognition protein (PGRP, cd06583), lysozyme (PHA00447) and Amidase_2 (N-acetylmuramoyl-L-alanine amidase, pfam01510). An area with similarity to a bacterial SH3 domain (SH3_3, pfam08239) is located at the C-terminus. Alignments of this protein with other *C. perfringens* endolysins whose activity has been demonstrated experimentally revealed that there is no significant similarity to ply3626 (49), plyCP26F or plyCP39O (40) (which all contain N-terminal Amidase_3 domains), or to Pms or PlyCM (34, 39) (whose enzymatic domains belongs to the glycosyl hydrolase_25 family), either in the N-terminal enzymatic domain or the C-terminal region, presumed to be responsible for the cell wall binding domain. However, in the C-terminal regions of Pms and PIyCM (34, 39) there are two SH3_3 domains that show some similarity to the SH3_3 hypothetical domain in the C-terminal area of the endolysin CP51L. CP51L does show similarity to a number of putative amidases from *C. perfringens* sequenced genomes in the NCBI databases (FIG. 3), with the homology to the 6 proteins with highest similarity being concentrated mostly in the central region between the conserved domains. The region of the Amidase_2 domain also showed some homology to predicted endolysins from podoviruses of *C. perfringens* (45).

Expression and Activity of CP51L

CP51L was expressed in *E. coli* as a His-tagged protein, giving a product of C. 45 kDa which was visible in crude extracts and bound a His-tag antibody (FIG. 2A, B). Crude protein extracts showed lytic activity when incubated with fresh *C. perfringens* cells; protein extraction using EB was most effective (FIG. 4A, B, C), giving a higher yield of endolysin and increased lytic activity (65.8±0.2% drop in $OD_{600}$ over 4 min when using 10 μg protein on fresh cells compared to extractions using either NP buffer, 12.4±0.1% or TN buffer, 12.4±0.4%), while lytic activity of the crude protein extracts from empty vector control samples was minimal over this period and similar to buffer controls (data not shown). CP51L was shown to be active at pH values ranging from 4.5 to 8.5, reaching the highest level of lytic activity at around pH 7 (FIG. 2D).

Ni-NTA columns were used to partially purify His-tagged CP51L from *E. coli* cells to assess lytic activity and host range of the endolysin. Strong lytic activity was shown by an effective drop in the $OD_{600}$ reading within 6 min of addition of 1, 10 or 30 μg of partially-purified protein to frozen cells of *C. perfringens* (FIG. 5A). The speed of cell lysis obtained with 1 pg of protein was similar to that obtained with 10 μg, the $OD_{600}$ dropping from c. 0.65 to c. 0.13 in less than 5 min. Lysis from 30 μg was slightly slower, while 0.1 μg gave a 9.1±0.1% drop in $OD_{600}$ over 4 min compared to 79.5±1.4% using 1 pg; 0.01 μg failed to produce appreciable lysis.

The partially purified CP51L was stable at 4° C. for several months and its activity was not affected by a 30 min incubation at 37° C. or 45° C. However, treatment at 65° C. for 30 min, or 42° C. overnight, or a pasteurization treatment at 72° C. for 20 s all abolished lytic activity. Stability at room temperature was monitored over 3 weeks, the activity remaining unchanged after 8 days compared to a sample stored at 4° C. After 15 d and 22d storage at room temperature the endolysin activity had reduced to C. 83% and C. 62% respectively, compared to the protein samples stored at 4° C.

Lysis assays were performed to examine the activity of CP51L when cells were suspended in broth media such as BHI+C or CM at pH 9 (FIG. 5B). Lytic activity was observed when cells were resuspended in BHI+C but was reduced in comparison to PBS, however the lysis in CM, a complex medium designed to simulate GI tract conditions, was actually more rapid. When tested under anaerobic conditions in BHI+C growth medium, the addition of endolysin to *C. perfringens* culture at the point of cell inoculation resulted in a dramatic reduction in viable cell counts (by 5 log) compared to the culture not exposed to endolysin (FIG. 6A). However, on continued culturing the pathogen was able to recover its population density. When the lysin was added to the culture during the log phase it failed to reduce the bacterial count (FIG. 6B).

The host range of CP51L was tested using frozen cells of *C. perfringens* strains and a variety of clostridial and non-clostridial species by incubating the cells with 1 μg of partially-purified lysin. All of the 25 *C. perfringens* strains tested were sensitive to the endolysin, but the speed of lysis varied greatly (Table 1). In some strains the drop in turbidity was immediate, while with others there was a lag of up to C. 20 mins before lysis was detected. Sensitivity to the positive control lysozyme was also variable, with some strains being insensitive while others exhibited an effective lysis. There was no apparent relationship between sensitivity to the CP51L lysin and to lysozyme. In addition, CP51L also showed activity against *C. bifermentans, C. acetobutylicum, C. beijerinckii, B. subtilis* and *B. cereus* cells (Table 1) but failed to cause lysis of a range of other bacteria (listed in Materials and Methods).

*L. johnsonii* as an Endolysin Delivery Vehicle

Figure 7:
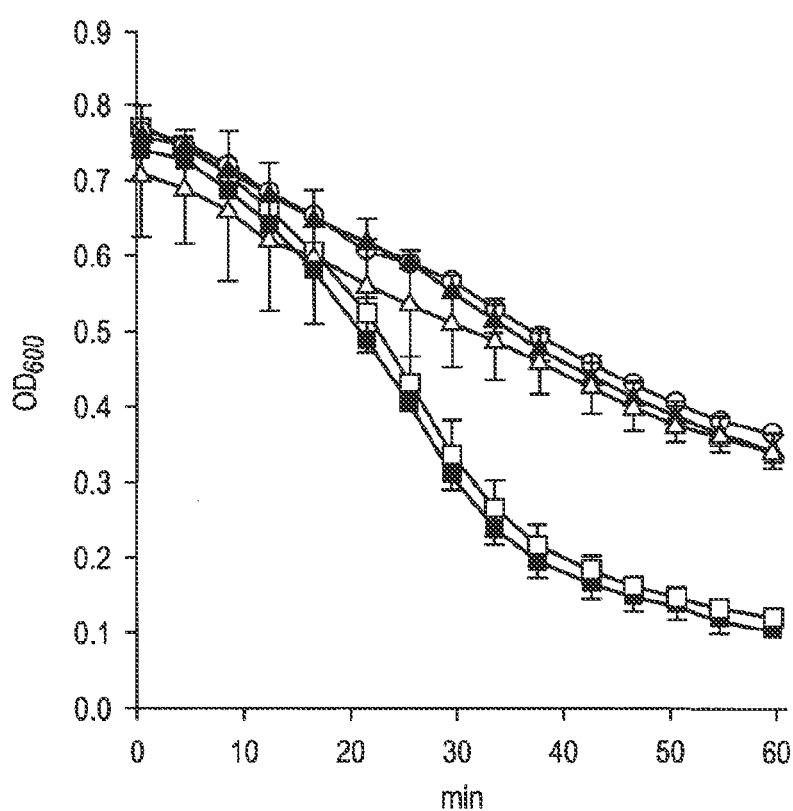
FIG. 7. Endolysin expression in *L. johnsonii*. Frozen cells of *C. perfringens* were incubated with 10 µg crude protein extracts from *L. johnsonii* FI10744-L (■) or FI10744-V (▲) or EB (o). Filled symbols were from cultures induced with nisin. Results are the mean of duplicate assays±standard deviation.

The cp51L gene was cloned into an expression and delivery system which combined expression from the $P_{nisA}$ in conjunction with the chromosomally-located signal transduction nisRK genes with a signal peptide to secrete the lysin. The His-tagged CP51L endolysin was not detectable by Western blotting in 10 μg of crude protein extracts from *L. johnsonii* carrying the lysin expression construct (FI10744-L). However, the FI10744-L extracts demonstrated a lytic activity that was absent from the extracts of the empty vector control (FI10744-V) (FIG. 7). Lytic activity from cells induced with nisin was equivalent to that from uninduced cells, demonstrating that the nisRK-$P_{nISA}$ system produced in *L. johnsonii* FI10744-L produces constitutive expression without the requirement for nisin induction. In addition, the SLPmod signal peptide proved to be effective for lysin secretion. The lytic activity associated with the concentrated supernatant was demonstrated in samples prepared from cultures of FI10744-L grown both with or without nisin induction (FIG. 8A). Constitutive endolysin expression and secretion was further demonstrated by growing colonies on plates incorporating autoclaved *C. perfringens* cells (FIG. 8B).

Discussion

*C. perfringens* is widely distributed in the intestine of animals, especially poultry, and can be pathogenic to the host. It is responsible both for severe infections and important economic losses (22, 38); targeting the pathogen in poultry will have impacts not just on poultry welfare and production but also on carriage in the food chain and the incidence of human infections. In this study Applicants have examined the ability of a novel endolysin to kill *C. perfringens* cells and to control populations in co-culture when secreted by a probiotic strain of *L. johnsonii.*

The gene for CP51L is located within a prophage which is inducible by mitomycin C (see Examples, below). In common with 3 other endolysins which have been demonstrated to show activity against *C. perfringens*, it is predicted to be an amidase (40, 49). This enzymatic type is encoded commonly in prophage lysin-like enzymes found in the genomes of *C. perfringens*, and the presence of an SH3 domain is also very prevalent in these proteins (39). In CP51L the predicted SH3_3 domain is present in the C-terminal region commonly associated with endolysin specificity (8, 25). The C-terminal and the central region between the amidase domain and the SH3_3 domain showed high similarity to other putative amidases from *C. perfringens*, suggesting that these regions may represent common binding domains for *C. perfringens* cell wall recognition.

When expressed from *E. coli*, CP51L showed a potent lytic activity against *C. perfringens* NCTC 3110, a Type B strain, and was also active against all 25 other *C. perfringens* strains tested. However, activity varied widely between strains, even between 2 strains of the same Type A (NCTC 8238 and 8239). Although sensitivity to the lysozyme positive control also varied to a lesser extent between strains, there was no relationship between the speed of lysis with lysozyme and that with CP51L, suggesting that the variation in CP51L activity may be associated with efficacy of recognition by the cell wall binding domains rather than with access of lytic enzymes to the peptidoglycan or intrinsic resistance of cells to lysis. The sensitivity of other selected clostridial and *Bacillus* spp. might indicate shared binding targets in the cell walls of these species. This large difference in activity between strains was also found with the amidase endolysins Ply3626, PlyCP39O and PlyCP26F and the glucosyl hydrolase endolysins SM101 and PlyCM (34, 39-40, 49), although CP51L shows a slightly less stringent host specificity than most of these lysins. The high stability, activity at physiologically relevant pH values and temperatures and the ability to lyse cells in complex media suggests that the endolysin is able to function in GI tract conditions, without causing collateral damage to the normal microflora.

*L. johnsonii* FI9785 was previously shown to reduce colonization and shedding of *C. perfringens* in chickens after a single oral dose (20), making it an ideal tool for prophylaxis. The use of a delivery system incorporating the signal peptide SLPmod, which has previously been demonstrated to be effective in the delivery of interleukin-12 to the murine gut by *Lactococcus lactis* (7), gave successful production and secretion of a functional enzyme, as demonstrated by the lysis assays. Further, the combination of the nisin A promoter and the chromosomally located signal transduction genes gave constitutive production without the need for nisin induction, which is of great potential benefit for in vivo applications. Production in *L. johnsonii* was lower than that in *E. coli* and this is an area which may benefit from improvement. Another possibility is co-delivery or co-application with other antimicrobials—the combination of a phage endolysin with nisin achieved a strong synergistic effect against *Staphylococcus aureus* (9) and the ability of lactobacilli to produce a range of bacteriocins, in addition to their other probiotic properties (21), make them valuable candidates as vehicles to deliver specific antimicrobials to gut communities.

The probiotic *L. johnsonii* has the capability to exclude *C. perfringens* from the GI tract of poultry birds. In this study Applicants have demonstrated its ability to express a biologically active anti-*C. perfringens* endolysin, indicating that the engineered strain has the potential to be an even more effective control agent for this pathogen.

REFERENCES

1. Altschul S F, Madden T L, Schaäffer A A, Zhang J, Zhang Z, Miller W, Lipman D J. 1997. Gapped BLAST and PSI-BLAST: a new generation of protein database search programs. Nucleic Acids Res. 25:3389-3402.
2. Atterbury R J, Van Bergen M A, Ortiz F, Lovell M A, Harris J A, De Boer A, Wagenaar J A, Allen V M, Barrow P A. 2007. Bacteriophage therapy to reduce *Salmonella* colonization of broiler chickens. Appl Environ Microbiol. 73:4543-9.
3. Braat H, Rottiers P, Hommes D W, Huyghebaert N, Remaut E, Remon J P, van Deventer S J, Neirynck S, Peppelenbosch M P, Steidler L. 2006. A phase I trial with transgenic bacteria expressing interleukin-10 in Crohn's disease. Clin Gastroenterol Hepatol. 4:754-9.
4. de Ruyter P G, Kuipers O P, de Vos W M. 1996. Controlled gene expression systems for *Lactococcus lactis* with the food-grade inducer nisin. Appl Environ Microbiol. 62:3662-7.
5. Dodd H M, Horn N, Hao Z, Gasson M J. 1992. A lactococcal expression system for engineered nisins. Appl Environ Microbiol. 58:3683-93.
6. EI-Shibiny A, Scott A, Timms A, Metawea Y, Connerton P, Connerton I. 2009. Application of a group II *Campylobacter* bacteriophage to reduce strains of *Campylobacter jejuni* and *Campylobacter coli* colonizing broiler chickens. J Food Prot. 72:733-40.
7. Fernandez A, Horn N, Wegmann U, Nicoletti C, Gasson M J, Narbad A. 2009. Enhanced secretion of biologically active murine interleukin-12 by *Lactococcus lactis*. Appl Environ Microbiol. 75:869-71.
8. Fischetti V A. 2010. Bacteriophage endolysins: a novel anti-infective to control Gram-positive pathogens. Int J Med Microbiol. 300:357-62.
9. Garcia P, Martinez B, Rodriguez L, Rodriguez A. 2010. Synergy between the phage endolysin LysH5 and nisin to kill *Staphylococcus aureus* in pasteurized milk. Int J Food Microbiol. 141:151-5.
10. Gil de los Santos J R, Storch O B, Fernandes C G, Gil-Turnes C. 2012. Evaluation in broilers of the probiotic properties of *Pichia pastoris* and a recombinant *P. pastoris* containing the *Clostridium perfringens* alpha toxin gene. Vet Microbiol. 156:448-51.
11. Grant K A, Kenyon S, Nwafor I, Plowman J, Ohai C, Halford-Maw R, Peck M W, McLauchlin J 2008. The identification and characterization of *Clostridium perfringens* by real-time PCR, location of enterotoxin gene, and heat resistance. Foodborne Pathog Dis. 5:629-39.
12. Gupta R, Prasad Y. 2011. P-27/HP endolysin as antibacterial agent for antibiotic resistant *Staphylococcus aureus* of human infections. Curr Microbiol. 63:39-45.
13. Hoopes J T, Stark C J, Kim H A, Sussman D J, Donovan D M, Nelson D C. 2009. Use of a bacteriophage lysin, PlyC, as an enzyme disinfectant against *Streptococcus equi*. Appl Environ Microbiol. 75:1388-94.
14. Horn N, Wegmann U, Narbad A, Gasson M J. 2005. Characterisation of a novel plasm id p9785S from *Lactobacillus johnsonii* FI9785. Plasmid. 54:176-83.
15. Keyburn A L, Boyce J D, Vaz P, Bannam T L, Ford M E, Parker D, Di Rubbo A, Rood J I, Moore R J. 2008. NetB, a new toxin that is associated with avian necrotic enteritis caused by *Clostridium perfringens*. PLoS Pathog. 4:e26.
16. Kizerwetter-Swida M, Binek M. 2009. Protective effect of potentially probiotic *Lactobacillus* strain on infection with pathogenic bacteria in chickens. Pol J Vet Sci. 12:15-20.
17. Kleerebezem M, Beerthuyzen M M, Vaughan E E, de Vos W M, Kuipers O P. 1997. Controlled gene expression systems for lactic acid bacteria: transferable nisin-inducible expression cassettes for *Lactococcus, Leuconostoc*, and *Lactobacillus* spp. Appl Environ Microbiol. 63:4581-4.
18. Kretzer J W, Lehmann R, Schmelcher M, Banz M, Kim K P, Korn C, Loessner M J. 2007. Use of high-affinity cell wall-binding domains of bacteriophage endolysins for immobilization and separation of bacterial cells. Appl Environ Microbiol. 73:1992-2000.
19. Kuipers O P, Beerthuyzen M M, de Ruyter P G, Luesink E J, de Vos W M. 1995. Autoregulation of nisin biosynthesis in *Lactococcus lactis* by signal transduction. J Biol Chem. 270:27299-304.
20. La Ragione R M, Narbad A, Gasson M J, Woodward M J. 2004. In vivo characterization of *Lactobacillus johnsonii* FI9785 for use as a defined competitive exclusion agent against bacterial pathogens in poultry. Lett Appl Microbiol. 38:197-205.
21. Lebeer S, Vanderleyden J, De Keersmaecker S C. 2008. Genes and molecules of lactobacilli supporting probiotic action. Microbiol Mol Biol Rev. 72:728-64.
22. Lee K W, Lillehoj H S, Jeong W, Jeoung H Y, An D J. 2011. Avian necrotic enteritis: experimental models, host immunity, pathogenesis, risk factors, and vaccine development. Poult Sci. 90:1381-90.
23. Lindstrom M, Heikinheimo A, Lahti P, Korkeala H. 2011. Novel insights into the epidemiology of *Clostridium perfringens* type A food poisoning. Food Microbiol. 28:192-8.
24. Liu D, Guo Y, Wang Z, Yuan J. 2010. Exogenous lysozyme influences *Clostridium perfringens* colonization and intestinal barrier function in broiler chickens. Avian Pathol. 39:17-24.
25. Loessner M J. 2005. Bacteriophage endolysins—current state of research and applications. Curr Opin Microbiol. 8:480-7.
26. Lu T K, Koeris M S. 2011. The next generation of bacteriophage therapy. Curr Opin Microbiol. 14:524-31.
27. Maguin E, Prevost H, Ehrlich S D, Gruss A. 1996. Efficient insertional mutagenesis in lactococci and other gram-positive bacteria. J Bacteriol. 178:931-5.
28. Mandalari G, Nueno Palop C, Tuohy K, Gibson G R, Bennett R N, Waldron K W, Bisignano G, Narbad A, Faulds C B. 2007. In vitro evaluation of the prebiotic activity of a pectic oligosaccharide-rich extract enzymatically derived from bergamot peel. Appl Microbiol Biotechnol. 73:1173-9.
29. Mayer M J, Narbad A, Gasson M J. 2008. Molecular characterization of a *Clostridium difficile* bacteriophage and its cloned biologically active endolysin. J Bacteriol. 190:6734-40.
30. Meng X, Shi Y, Ji W, Zhang J, Wang H, Lu C, Sun J, Yan Y. 2011. Application of a bacteriophage lysin to disrupt biofilms formed by the animal pathogen *Streptococcus suis*. Appl Environ Microbiol. 77:8272-9.
31. Miller R W, Skinner E J, Sulakvelidze A, Mathis G F, Hofacre C L. 2010. Bacteriophage therapy for control of necrotic enteritis of broiler chickens experimentally infected with *Clostridium perfringens*. Avian Dis. 54:33-40.
32. Miyamoto K, Li J, McClane B A. 2012. Enterotoxigenic *Clostridium perfringens*: Detection and Identification. Microbes Environ. 27:343-9.
33. Morales C A, Oakley B B, Garrish J K, Siragusa G R, Ard M B, Seal B S. 2012. Complete genome sequence of the podoviral bacteriophage φCP24R, which is virulent for *Clostridium perfringens*. Arch Virol. 157:769-72.
34. Nariya H, Miyata S, Tamai E, Sekiya H, Maki J, Okabe A. 2011. Identification and characterization of a putative endolysin encoded by episomal phage φSM101 of *Clostridium perfringens*. Appl Microbiol Biotechnol. 90:1973-9.
35. O'Flaherty S, Ross R P, Coffey A. 2009. Bacteriophage and their lysins for elimination of infectious bacteria. FEMS Microbiol Rev. 33:801-19.
36. Oakley B B, Talundzic E, Morales C A, Hiett K L, Siragusa G R, Volozhantsev N V, Seal B S. 2011. Comparative genomics of four closely related *Clostridium perfringens* bacteriophages reveals variable evolution among core genes with therapeutic potential. BMC Genomics. 12:282.
37. Petit L, Gibert M, Popoff M R. 1999. *Clostridium perfringens*: toxinotype and genotype. Trends Microbiol. 7:104-10.
38. Scallan E, Hoekstra R M, Angulo F J, Tauxe R V, Widdowson M A, Roy S L, Jones J L, Griffin P M. 2011. Foodborne Illness Acquired in the United States-Major Pathogens. Emerg Infect Dis. 17:7-15.
39. Schmitz J E, Ossiprandi M C, Rumah K R, Fischetti V A. 2011. Lytic enzyme discovery through multigenomic sequence analysis in *Clostridium perfringens*. Appl Microbiol Biotechnol. 89:1783-95.

40. Simmons M, Donovan D M, Siragusa G R, Seal B S. 2010. Recombinant expression of two bacteriophage proteins that lyse *Clostridium perfringens* and share identical sequences in the C-terminal cell wall binding domain of the molecules but are dissimilar in their N-terminal active domains. J Agric Food Chem. 58:10330-7.
41. Stentz R, Bongaerts R J, Gunning A P, Gasson M, Shearman C. 2010. Controlled release of protein from viable *Lactococcus lactis* cells. Appl Environ Microbiol. 76:3026-31.
42. Timbermont L, Lanckriet A, Dewulf J, Nollet N, Schwarzer K, Haesebrouck F, Ducatelle R, Van Immerseel F. 2010. Control of *Clostridium perfringens*-induced necrotic enteritis in broilers by target-released butyric acid, fatty acids and essential oils. Avian Pathol. 39:117-21.
43. Turner M S, Waldherr F, Loessner M J, Giffard P M. 2007. Antimicrobial activity of lysostaphin and a *Listeria monocytogenes* bacteriophage endolysin produced and secreted by lactic acid bacteria. Syst Appl Microbiol. 30:58-67.
44. Van Immerseel F, Rood J I, Moore R J, Titball R W. 2009. Rethinking our understanding of the pathogenesis of necrotic enteritis in chickens. Trends Microbiol. 17:32-6.
45. Volozhantsev N V, Oakley B B, Morales C A, Verevkin W, Bannov V A, Krasilnikova V M, Popova A V, Zhilenkov E L, Garrish J K, Schegg K M, Woolsey R, Quilici D R, Line J E, Hiett K L, Siragusa G R, Svetoch E A, Seal B S. 2012. Molecular characterization of podoviral bacteriophages virulent for *Clostridium perfringens* and their comparison with members of the Picovirinae. PLoS One. 7:e38283.
46. Volozhantsev N V, Verevkin W, Bannov V A, Krasilnikova V M, Myakinina V P, Zhilenkov E L, Svetoch E A, Stern N J, Oakley B B, Seal B S. 2011. The genome sequence and proteome of bacteriophage φCPV1 virulent for *Clostridium perfringens*. Virus Res. 155:433-9.
47. Wegmann U, Klein J R, Drumm I, Kuipers O P, Henrich B. 1999. Introduction of peptidase genes from *Lactobacillus delbrueckii* subsp. *lactis* into *Lactococcus lactis* and controlled expression. Appl Environ Microbiol. 65:4729-33.
48. Zhang G, Mathis G F, Hofacre C L, Yaghmaee P, Holley R A, Duranc T D. 2010. Effect of a radiant energy-treated lysozyme antimicrobial blend on the control of clostridial necrotic enteritis in broiler chickens. Avian Dis. 54:1298-300.
49. Zimmer M, Vukov N, Scherer S, Loessner M J. 2002. The murein hydrolase of the bacteriophage φ3626 dual lysis system is active against all tested *Clostridium perfringens* strains. Appl Environ Microbiol. 68:5311-7.

Example C—Novel Strategies to Combat *Clostridium Perfringens* in the Gastrointestinal Tract Abstract The problem of food-borne pathogens associated with meat consumption has a significant impact on both health and the economy. *Clostridium perfringens* is frequently found in food and the environment and produces potent toxins that have a negative impact on both human and animal health and particularly on the poultry industry. The probiotic *Lactobacillus johnsonii* FI9785 has been demonstrated to competitively exclude *Clostridium perfringens* in poultry. Applicants have investigated the interaction between wild type *L. johnsonii* FI9785 or an engineered strain expressing a cell wall hydrolysing endolysin and *C. perfringens* in vitro, using a batch culture designed to simulate human gastrointestinal tract conditions. Applicants' aim was to understand the mechanism of competitive exclusion and to assess the efficacy of the endolysin as a novel antimicrobial for the control of *Clostridium perfringens* in the gut environment. Co-cultures of *L. johnsonii* and *C. perfringens* indicated that acid production by the probiotic is important in pathogen control. The co-culture of the endolysin-secreting *L. johnsonii* with *C. perfringens* showed that the engineered strain had the potential to control the pathogen.

1. Introduction 1.1 *Clostridium perfringens*—Pathogenesis and Control Strategies

*Clostridium perfringens* is a Gram-positive, spore forming, anaerobic bacterium that is widely distributed in the intestines of people and animals and is also common in the environment and easily found in a variety of foods. *C. perfringens* is classified into 5 types (A, B, C, D, E) based on toxin production (Miyamoto et al., 2012; Petit et al., 1999). It is the causative agent of several disease in humans and animals such as gas gangrene or necrotic enteritis (NE), and is also a common source of food poisoning (Keyburn et al., 2008; Lindstrom et al., 2011). It is the cause of both severe infections and important economic losses, especially in poultry (Lee et al., 2011; Scallan et al., 2011).

NE is one of the most important enteric diseases in poultry and causes high costs to the poultry industry. Antibiotics can be used for the control of NE in poultry, but in some cases the development of resistance by *C. perfringens* strains has been described (Johansson et al., 2004). The ban, in some countries, of the prophylactic use of antibiotics for the control of NE in poultry feed was initiated in response to the spread of antibiotic resistance in human and animal bacterial pathogens (Chapin et al., 2005). However the ban has increased the emergence of diseases that were previously controlled, such as NE in the poultry industry (Lee et al., 2011; Van Immerseel et al., 2009). For this reason a range of novel strategies to combat *C. perfringens* are being exploited such as vaccination (Lee et al., 2011), natural antimicrobials and enzymes (Liu et al., 2010; Timbermont et al., 2010; Zhang et al., 2010), probiotic microorganisms (Gil de los Santos et al., 2012; Kizerwetter-Swida and Binek, 2009; La Ragione et al., 2004) or bacteriophages (Miller et al., 2010).

1.2 Potential of Probiotics and Endolysins as Control Agents

Probiotics are defined by the World Health Organisation as 'Live microorganisms, which when administered in adequate amounts confer a health benefit on the host'. Many of the known probiotics are lactic acid bacteria; they are normally derived from healthy intestinal microflora and can exert several positive effects (Lebeer et al., 2008). Lactobacilli have been showed to exert health benefits in both humans and animals, preventing or treating several diseases caused by pathogens. Meta-analysis showed that certain lactobacilli can prevent necrotizing enterocolitis in preterm neonates (Alfaleh et al., 2011), reduce the occurrence of *C. difficile* associated diarrhoea (McFarland, 2006) or reduce the *Listeria monocytogenes* count in acquired listeriosis (Archambaud et al., 2012). In animal models probiotics have been explored as alternatives to conventional antimicrobials to control problems such as pathogenic avian influenza (Seo et al., 2012) or disease caused by *Salmonella enterica* (Chen et al., 2012).

Different proprieties contribute to the positive effects of probiotics on health, including both interactions between microbes (competition for nutrients, the production of antimicrobial compounds, competitive exclusion) and effects on the host (Lebeer et al., 2008). In recent years, the development of probiotics engineered for the secretion of heterologous proteins has increased, showing potential for the treatment or prevention of disease. Probiotic microorganisms have been demonstrated as potential tools for the delivery of biologically active molecules such as interleukins (Bract et al., 2006; Fernandez et al., 2009) or antivirals (Moeini et al., 2011). They have also successfully expressed cell wall hydrolases such as endolysins (Turner et al., 2007). Endolysins are enzymes produced by bacteriophages in order to lyse host cells and release new virions.

Figure 9A:
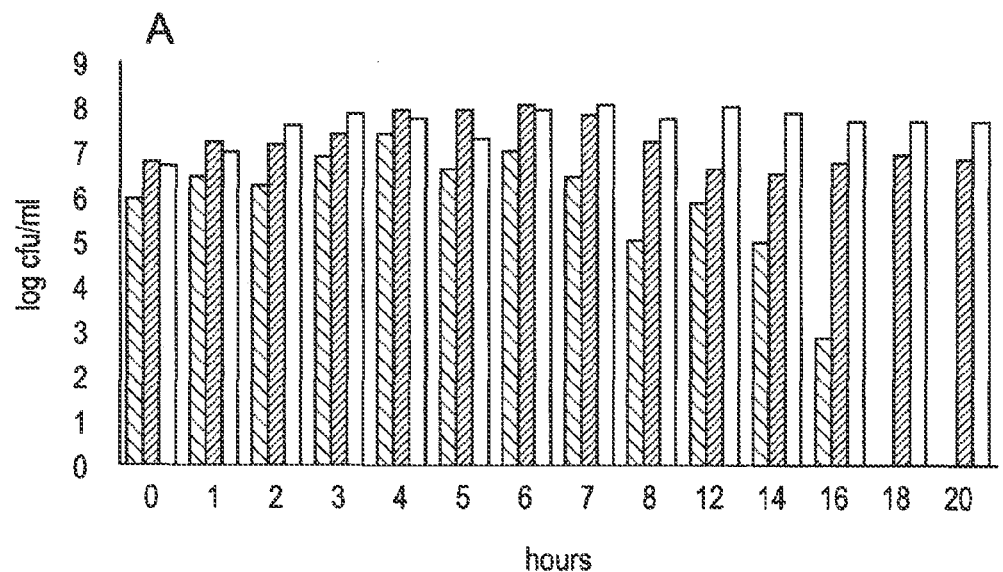
FIG. 9A-B. Co-culture of *C. perfringens* and *L. johnsonii* in mini batch cultures. Cell counts were taken from two separate experiments (FIGS. 9A and 9B) containing either *C. perfringens* pure culture (white bars) or *L. johnsonii* FI9785 (black bars) in co-culture with *C. perfringens* (grey bars).
Figure 9B:
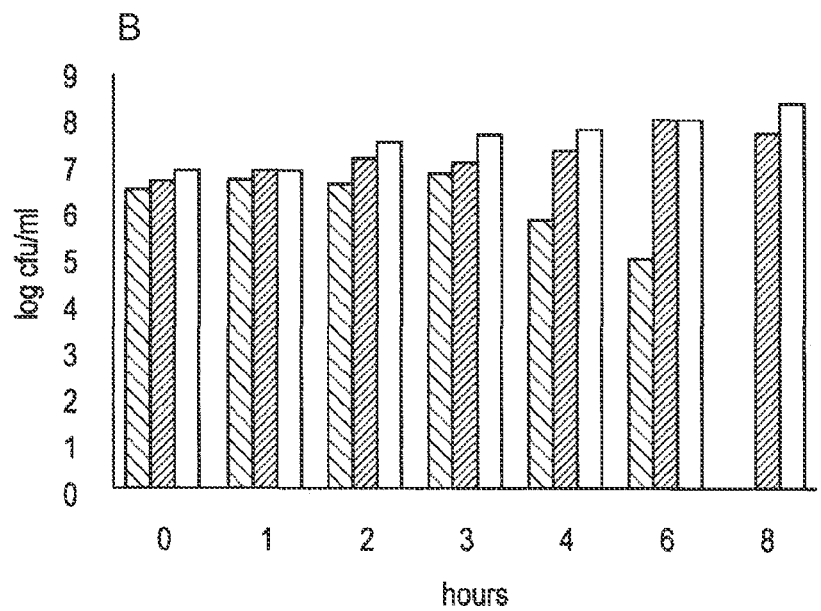

Their lytic ability and specificity has been exploited to develop novel antimicrobial activities against a range of Gram positive pathogens (Fischetti, 2010). Although potent, endolysins are susceptible to proteases and delivery to the gastrointestinal (GI) tract is likely to be problematic. However, expression and secretion from lactic acid bacteria represents a method for continuous production and delivery in the gut environment. Endolysin CP51L has been shown to be active against *C. perfringens* in vitro and constitutive expression and export of this endolysin from the lactic acid bacterium *L. johnsonii* FI9785 has recently been demonstrated (see Examples, below).

1.3 Development of a Novel Control Strategy

In Applicants' study the activity of both an established probiotic and an engineered derivative was investigated for the control of *C. perfringens*. *L. johnsonii* FI9785 is a poultry-isolated strain which has been confirmed in vivo as a competitive exclusion agent against *C. perfringens* in chickens (La Ragione et al., 2004). In this work, Applicants have performed co-culture experiments to explore the ability of *L. johnsonii* to control *C. perfringens*. In addition, to improve the performance of *L. johnsonii* Applicants have investigated the ability of a strain engineered for the expression and delivery of endolysin CP51L to control *C. perfringens* in vitro in conditions designed to simulate the GI tract.

2. Method 2.1 Bacterial Strains and Growth Conditions

*C. perfringens* strain NCTC 3110 was obtained from the National Collection of Type Cultures (Public Health Laboratory, London, UK). The strain was grown anaerobically overnight at 37° C. in BHI (Oxoid) supplemented with vitamin K [10 μl; 50 mg/l], hemin [5 mg/l], resazurin [1 mg/l], and L-cysteine[0.5 g/l]. Stocks were maintained at 4° C. in Robertson's cooked-meat medium (SGL, Corby, UK). *Lactobacillus johnsonii* strain FI9785 (La Ragione et al., 2004) and derivatives were grown in MRS broth or agar (Oxoid) at 37° C. Co-cultures and in vitro batch cultures were performed in chemostat media (CM: peptone water 2 g/l (Oxoid), yeast extract 2 g/l (Oxoid), $NaC_I$ 0.1 g/l, $K_2HPO_4$ 0.04 g/l, $KH_2PO_4$. 0.04 g/l, $MgSO_4.7H_2O$ 0.01 g/l, $CaCl_2.6H_2O$ 0.01 g/l, $NaHCO_3$ 2 g/l, Tween 80 2 ml, hemin 0.02 g/l dissolved in 400 μl 1 M NaOH, vitamin K1 10 μl of 5% v/v aqueous solution, cysteine HCl 0.5 g/l, bile salts 0.5 g/I, 1% glucose, all from Sigma (Mandalari et al., 2007)).

The endolysin delivery system involved *Lactobacillus johnsonii* strain FI10744, constructed by the insertion of the nisRK genes into the chromosome, expressing plasmid pUK200-PnisA-slpmod-6×His-cp511 (FI10744-L) which allowed constitutive expression and signal peptide-mediated secretion of histidine-tagged endolysin (see Examples, below). Strain FI10744-V contained the empty pUK200 vector as a control; both strains were grown with chloramphenicol (7.5 μg/ml) to select for the plasmid except during co-culture assays, where no antibiotics were present.

2.2 In Vitro Batch Culture and Viability Assessment

Batch cultures were carried out over 48 h according to the procedure described previously (Mandalari et al., 2007). Briefly, each reactor consisted of a 300 ml water jacketed fermentation vessel (Shoam Scientific, UK), containing 250 ml chemostat medium, magnetically stirred and maintained at 37° C. by a circulating water bath. Culture pH was automatically controlled and maintained by addition of 1M HCl or 1M NaOH. Anaerobic conditions were maintained by sparging the vessels with oxygen-free nitrogen. Vessels with media were autoclaved at 121° C. for 15 min then equilibrated overnight to create anaerobic conditions prior to the inoculation of the microorganisms. Initial mini-batch culture tests were performed in 25 ml culture of the same medium under anaerobic conditions at 37° C. but without stirring or pH control. Bacteria were inoculated from overnight cultures in MRS or BHI with supplements (*L. johnsonii* and *C. perfringens* respectively) with antibiotic selection for plasmids where appropriate.

At specific time points samples were withdrawn and serial dilutions were performed anaerobically in PBS. Both diluted and undiluted samples were plated in triplicate using a spot-plate method on BHI agar with gentamycin (20 μg/ml) to enumerate *C. perfringens*, or MRS agar grown aerobically and containing colistin sulphate (50 μg/ml) to select for *L. johnsonii*. Strains *L. johnsonii* FI10744-L and FI10744-V were plated on MRS with or without chloramphenicol (7.5 μg/ml) to assess plasmid loss in the absence of selection and were incubated aerobically. Plates were incubated for 24 to 48 h and results were calculated as the total colony forming units (cfu) from triplicate spots.

2.3 Lysis Assay

Endolysin-mediated lysis of *C. perfringens* NCTC 3110 cells resuspended in phosphate buffered saline (PBS) was assessed by turbidity reduction assay as previously described (Mayer et al., 2008). At the end of the batch culture experiments, spent medium was tested to assess endolysin activity. To assess the stability of the endolysin in spent media, endolysin protein was produced from cells of *Escherichia coli* expressing construct pET15b-cp 511 (see Examples, below) and partially purified using a nickel-nitrilotriacetic acid (Ni-NTA) Fast Start kit (Qiagen) as described previously (Mayer et al., 2008). 1 ml of spent medium was harvested, filtered and endolysin was added to a final concentration of 0.33 μg/pl. 30 μl samples (equivalent to 10 μg) were taken at intervals for 96 h and used in turbidity reduction assays, with elution buffer EB (50 mM sodium phosphate, 300 mM NaCl, 250 mM imidazole pH 8) as a negative control. Assays were performed in duplicate.

3. Results 3.1 Co-Culture of *C. perfringens* and *L. johnsonii*

The ability of the probiotic *L. johnsonii* FI9785 to inhibit the growth of *C. perfringens* in vitro was evaluated in co-culture experiments carried out in a complex growth medium formulated to simulate the conditions of the GI tract, where both the microorganisms could survive but where growth was limited.

Preliminary tests in 25 ml without pH control revealed a significant decrease in the viability of *C. perfringens* when co-inoculated with *L. johnsonii* compared to pure culture (FIG. 9). In pure culture in the first experiment the numbers of *C. perfringens* were maintained throughout the 20 h sampling period, with some increase in numbers (FIG. 9a). In contrast, co-culture with *L. johnsonii* FI9785 led to a decrease in viability after 7 h and at 18 h, where no live cells were detected in an undiluted sample. In a second experiment the negative effect of the probiotic was more rapid, with a loss of viable cells by 8 h (FIG. 9b) and re-emergence of the pathogen in samples taken at 13, 15, 17, or 19 h was not observed (data not shown)

3.2 In Vitro Batch Fermentation

To study the interaction of the microorganisms, the co-culture of *C. perfringens* with *L. johnsonii* FI9785 was repeated in larger volumes in an in vitro batch fermentation model with a controlled pH. At time 0, cells were added from overnight cultures to give an estimated final concentration of c. $2\times10^6$ cells/ml of each bacterium in vessel 1 or $2\times10^6$ cells/ml of pure cultures in control vessels 2 (*C. perfringens*) and 3 (*L. johnsonii*). The first test was conducted for 24 h at a pH range between 6.8 and 7.2 (FIG. 10A). As with the mini-batch culture, *C. perfringens* in pure culture showed a slight increase in numbers during the first 8 h of culture and maintained a viable cell count of $>1\times10^6$ cells/ml. In co-culture with *L. johnsonii*, growth was not as noticeable but the number of viable cells did not seem to be significantly reduced, indeed the survival of *C. perfringens* was better at 24 h than that of the probiotic strain. Despite using the same volume for inoculation, in the mixed culture the *C. perfringens* initial cell count was noted to be about 1 log less in comparison with that in the vessels containing the pure culture; this was assumed to be a result of limited oxygen exposure during inoculation as the pure culture vessels were inoculated first. The test was repeated increasing the incubation time to 48 h (FIG. 10B). As before, co-culture with *L. johnsonii* failed to reduce the numbers of *C. perfringens*, which were maintained even at 48 h, while *L. johnsonii* in both co-culture and pure culture showed a lesser ability to survive and was not recoverable from 60 µl samples. To obtain better conditions for *L. johnsonii*, the third test was conducted using a pH range between 5.8 and 6.2 (FIG. 10C). Survival of the probiotic was improved in these conditions but again there was no control of the pathogen.

3.3 Effect of Endolysin Delivery on *C. perfringens*

Batch culture experiments were repeated using a strain of *L. johnsonii* (FI10744-L) which had been engineered for antimicrobial production. This strain expressed a histidine-tagged endolysin CP51L from the vector pUK200-PnisA-sIpmod-6×His-cp51l which produced constitutive expression via an interaction between the nisin A promoter and chromosomally located nisRK genes and export from the cell via the signal peptide SLPmod (see Examples, below). The effect of this strain in co-culture with *C. perfringens* was compared to that of strain FI10744-V carrying an empty vector control. As the previous experiments had indicated a lower ability of *L. johnsonii* to survive and replicate in batch culture, *L. johnsonii* strains were inoculated at a c. 10-fold excess to *C. perfringens* and a pH range between 5.8 and 6.2 was used to improve their viability over the 48 h test period. *L. johnsonii* FI10744-L did show some ability to reduce the numbers of *C. perfringens* compared to a co-culture containing *L. johnsonii* FI10744-V, but results varied with replicate experiments (FIG. 11). The numbers of *C. perfringens* co-cultured with *L. johnsonii* FI10744-L were less than those in vessels co-cultured with *L. johnsonii* FI10744-V in experiments A (c. 2.6-log less at 48 h) and B (c. 2-log less), despite the poor survival of both *L. johnsonii* strains in experiment A. However, despite an initial drop, *C. perfringens* numbers recovered in experiment C and no control of the pathogen was achieved; instead the endolysin producer was not recoverable in aliquots of 60 µl taken from the vessel at 48 h. This low survival of the endolysin producer strain was also sometimes seen in other batch experiments and makes the effects on *C. perfringens* hard to assess. Survival was particularly poor in experiment C where the final numbers of *C. perfringens* were not controlled (FIG. 11C) and this may be related to the failure of the engineered probiotic to control the pathogen. Interestingly, plating the *L. johnsonii* strains on both selective and non-selective media demonstrated that there was no loss of the plasmids during the 48 h culture period, despite the absence of antibiotic selection in the batch culture.

3.4 Endolysin Stability

Figure 12:
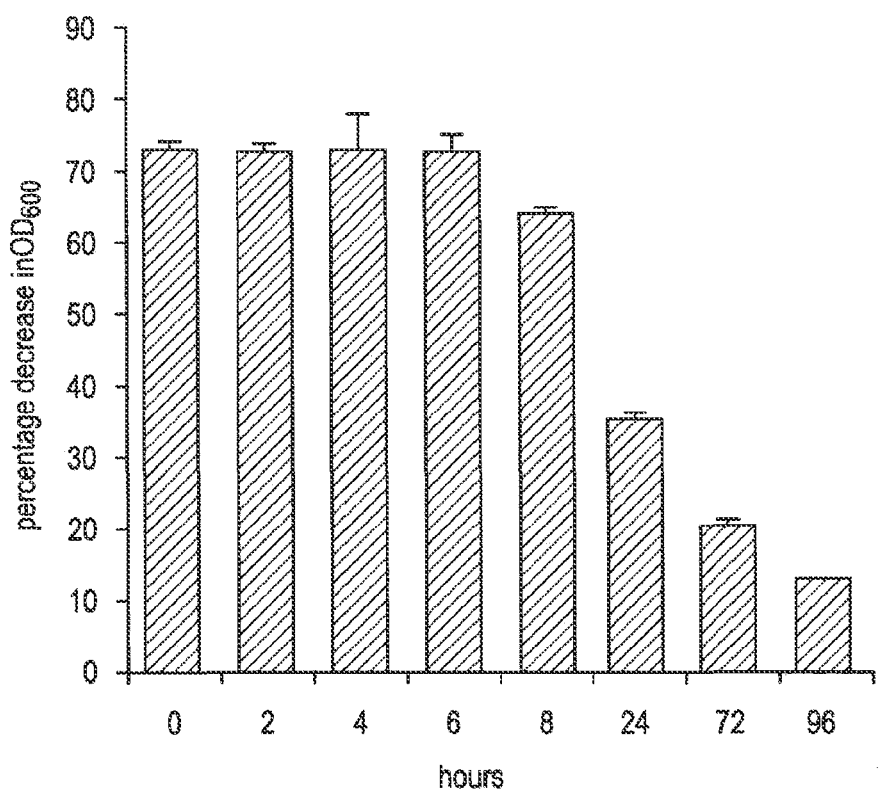
FIG. 12. CP51L stability in spent batch medium. Endolysin activity was measured in a turbidity reduction assay using 10 mg aliquots on frozen cells. Results represent the percentage decrease in $OD_{600}$ over 4 min of linear lysis and are the mean of duplicate assays±standard deviation.

No lytic activity was observed when spent medium was tested to assess endolysin activity, indicating that the lysin concentration was not sufficient for effective lysis in the turbidity reduction assays. Lysis assays conducted in spent media showed no drop in activity for the first 6 h, followed by a slight decrease at 8 h; after 24 h the activity was reduced by 50% and at 72 h and 96 h lysis was similar to that in the buffer control (FIG. 12).

4. Discussion

In this work Applicants have investigated the potential of the probiotic competitive exclusion agent *L. johnsonii* and an engineered derivative to control the pathogen *C. perfringens* in vitro. To simulate the conditions of the GI tract, a batch fermentation system was used together with a complex medium. Preliminary work showed that although pathogen numbers were clearly reduced in co-culture, the addition of pH controls in batch culture removed this effect, indicating that the production of acids may be an important feature of the ability of *L. johnsonii* to exclude *C. perfringens*. The production of lactic acid by lactobacilli is established as an important facet of their antimicrobial nature (Lebeer et al., 2008), and the pH of the medium also clearly had an effect on *L. johnsonii* viability.

To attempt to improve control of the pathogen, a strain which produced and secreted biologically active endolysin CP51L was tested. This system exported the endolysin via a signal peptide which has been proven to effectively deliver murine interleukin-12 from *Lactococcus lactis* to the murine gut (Fernandez et al., 2009). In 2 out of 3 co-culture experiments, expression of the endolysin led to a reduction in the pathogen counts compared with co-cultures of *C. perfringens* with the *L. johnsonii* vector control. Lytic activity of the endolysin in the chemostat medium has previously been demonstrated (see Example B) and although the concentration of the endolysin in the medium from the co-culture experiments was not concentrated enough to detect using turbidity reduction assays, these experiments demonstrate the potential of the endolysin to improve control of *C. perfringens*. Although batch cultures are stirred continuously one can expect to obtain areas where the clostridial cells are not inevitably next to *L. johnsonii* cells and so are able to survive and multiply. In all batch co-cultures *L. johnsonii* strains failed to maintain their starting inoculum levels and this may also have had an effect on their ability to control *C. perfringens*. Activity in the GI tract, where *L. johnsonii* survives well, would be expected to function better.

This work confirms that *L. johnsonii* has the potential to control *C. perfringens* and that endolysin expression and delivery can increase the efficacy of the probiotic.

REFERENCES

Alfaleh, K., Anabrees, J., Bassler, D. & Al-Kharfi, T. (2011). Probiotics for prevention of necrotizing enterocolitis in preterm infants. *Cochrane Database Syst Rev*, CD005496.

Archambaud, C., Nahori, M. A., Soubigou, G., Becavin, C., Laval, L., Lechat, P. . . . Cossart, P. (2012). Impact of lactobacilli on orally acquired listeriosis. *Proc Natl Acad Sci USA* 109, 16684-16689.

Braat, H., Rottiers, P., Hommes, D. W., Huyghebaert, N., Remaut, E., Remon, J. P. . . . Steidler, L. (2006). A phase I trial with transgenic bacteria expressing interleukin-10 in Crohn's disease. *Clin Gastroenterol Hepatol* 4, 754-759.

Chapin, A., Rule, A., Gibson, K., Buckley, T. & Schwab, K. (2005). Airborne multidrug-resistant bacteria isolated from a concentrated swine feeding operation. *Environ Health Perspect* 113, 137-142.

Chen, C. Y., Tsen, H. Y., Lin, C. L., Yu, B. & Chen, C. S. (2012). Oral administration of a combination of select lactic acid bacteria strains to reduce the *Salmonella* invasion and inflammation of broiler chicks. *Poult Sci* 91, 2139-2147.

Fernandez, A., Horn, N., Wegmann, U., Nicoletti, C., Gasson, M. J. & Narbad, A. (2009). Enhanced secretion of biologically active marine interleukin-12 by *Lactococcus lactis*. *Appl Environ Microbiol* 75, 869-871.

Fischetti, V. A. (2010). Bacteriophage endolysins: a novel anti-infective to control Gram-positive pathogens. *Int J Med Microbiol* 300, 357-362.

Gil de los Santos, J. R., Storch, 0. B., Fernandes, C. G. & Gil-Turnes, C. (2012). Evaluation in broilers of the probiotic properties of *Pichia pastoris* and a recombinant *P. pastoris* containing the *Clostridium perfringens* alpha toxin gene. *Vet Microbiol* 156, 448-451.

Johansson, A., Greko, C., Engstrom, B. E. & Karlsson, M. (2004). Antimicrobial susceptibility of Swedish, Norwegian and Danish isolates of *Clostridium perfringens* from poultry, and distribution of tetracycline resistance genes. *Vet Microbiol* 99, 251-257.

Keyburn, A. L., Boyce, J. D., Vaz, P., Bannam, T. L., Ford, M. E., Parker, D. . . . Moore, R. J. (2008). NetB, a new toxin that is associated with avian necrotic enteritis caused by *Clostridium perfringens*. *PLoS Pathog* 4, e26.

Kizerwetter-Swida, M. & Binek, M. (2009). Protective effect of potentially probiotic *Lactobacillus* strain on infection with pathogenic bacteria in chickens. *Pol J Vet Sci* 12, 15-20.

La Ragione, R. M., Narbad, A., Gasson, M. J. & Woodward, M. J. (2004). In vivo characterization of *Lactobacillus johnsonii* FI9785 for use as a defined competitive exclusion agent against bacterial pathogens in poultry. *Lett Appl Microbiol* 38, 197-205.

Lebeer, S., Vanderleyden, J. & De Keersmaecker, S. C. (2008). Genes and molecules of lactobacilli supporting probiotic action. *Microbiol Mol Biol Rev* 72, 728-764, Table of Contents.

Lee, K. W., Lillehoj, H. S., Jeong, W., Jeoung, H. Y. & An, D. J. (2011). Avian necrotic enteritis: experimental models, host immunity, pathogenesis, risk factors, and vaccine development. *Poult Sci* 90, 1381-1390.

Lindstrom, M., Heikinheimo, A., Lahti, P. & Korkeala, H. (2011). Novel insights into the epidemiology of *Clostridium perfringens* type A food poisoning. *Food Microbiol* 28, 192-198.

Liu, D., Guo, Y., Wang, Z. & Yuan, J. (2010). Exogenous lysozyme influences *Clostridium perfringens* colonization and intestinal barrier function in broiler chickens. *Avian Pathol* 39, 17-24.

Mandalari, G., Nueno Palop, C., Tuohy, K., Gibson, G. R., Bennett, R. N., Waldron, K. W. . . . Faulds, C. B. (2007). In vitro evaluation of the prebiotic activity of a pectic oligosaccharide-rich extract enzymatically derived from bergamot peel. *Appl Microbiol Biotechnol* 73, 1173-1179.

Mayer, M. J., Narbad, A. & Gasson, M. J. (2008). Molecular characterization of a *Clostridium difficile* bacteriophage and its cloned biologically active endolysin. *J Bacteriol* 190, 6734-6740.

McFarland, L. V. (2006). Meta-analysis of probiotics for the prevention of antibiotic associated diarrhea and the treatment of *Clostridium difficile* disease. *Am J Gastroenterol* 101, 812-822.

Miller, R. W., Skinner, E. J., Sulakvelidze, A., Mathis, G. F. & Hofacre, C. L. (2010). Bacteriophage therapy for control of necrotic enteritis of broiler chickens experimentally infected with *Clostridium perfringens*. *Avian Dis* 54, 33-40.

Miyamoto, K., Li, J. & McClane, B. A. (2012). Enterotoxigenic *Clostridium perfringens*: Detection and Identification. *Microbes Environ*.

Moeini, H., Rahim, R. A., Omar, A. R., Shafee, N. & Yusoff, K. (2011). *Lactobacillus acidophilus* as a live vehicle for oral immunization against chicken anemia virus. *Appl Microbiol Biotechnol* 90, 77-88.

Petit, L., Gibert, M. & Popoff, M. R. (1999). *Clostridium perfringens*: toxinotype and genotype. *Trends Microbiol* 7, 104-110.

Scallan, E., Hoekstra, R. M., Angulo, F. J., Tauxe, R. V., Widdowson, M. A., Roy, S. L. . . . Griffin, P. M. (2011). Foodborne Illness Acquired in the United States-Major Pathogens. *Emerg Infect Dis* 17, 7-15.

Seo, B. J., Rather, I. A., Kumar, V. J., Choi, U. H., Moon, M. R., Lim, J. H. & Park, Y. H. (2012). Evaluation of *Leuconostoc mesenteroides* YML003 as a probiotic against low-pathogenic avian influenza (H9N2) virus in chickens. *J Appl Microbiol* 113, 163-171.

Timbermont, L., Lanckriet, A., Dewulf, J., Nollet, N., Schwarzer, K., Haesebrouck, F. . . . Van Immerseel, F. (2010). Control of *Clostridium perfringens*-induced necrotic enteritis in broilers by target-released butyric acid, fatty acids and essential oils. *Avian Pathol* 39, 117-121.

Turner, M. S., Waldherr, F., Loessner, M. J. & Giffard, P. M. (2007). Antimicrobial activity of lysostaphin and a *Listeria monocytogenes* bacteriophage endolysin produced and secreted by lactic acid bacteria. *Syst Appl Microbiol* 30, 58-67.

Van Immerseel, F., Rood, J. I., Moore, R. J. & Titball, R. W. (2009). Rethinking our understanding of the pathogenesis of necrotic enteritis in chickens. *Trends Microbiol* 17, 32-36.

Zhang, G., Mathis, G. F., Hofacre, C. L., Yaghmaee, P., Holley, R. A. & Duranc, T. D. (2010). Effect of a radiant energy-treated lysozyme antimicrobial blend on the control of clostridial necrotic enteritis in broiler chickens. *Avian Dis* 54, 1298-1300.

TABLE 1

Lytic activity of CP51L against sensitive strains.

| Bacterial strains | CP51L lytic activity[a] | Lag (min) | Lysozyme |
|---|---|---|---|
| C. perfringens NCTC 3110 | 79.5 ± 1.0 | 1 | — |
| C. perfringens NCTC 8238 | 59.2 ± 0.9 | 6 | 21.8 ± 1.5 |
| C. perfringens NCTC 8239 | 28.6 ± 0.4 | 6 | 10.6 ± 0.6 |
| C. perfringens 5146-97[b] | 58.8 ± 4.4 | 4 | 8.5 ± 0.5 |
| C. perfringens 5810-97[b] | 17.1 ± 2.5 | 10

TABLE 2-continued

Analysis of the ΦCP51 genome

| ORF | Location[a] | Size (aa)[b] | BlastP most significant match (organism, E value); top match showing possible function[c] | Domains |
|---|---|---|---|---|
| 15 | 9101_9559 | 152 | HP (*Clostridium perfringens* F262, 6e−104); major capsid protein GpP (*Bacillus* phage PBC1, 1e−07) | |
| 16 | 9572_9940 | 122 | HP (*Clostridium perfringens* ATCC 13124, 2e−77) | |
| 17 | 9900_10262 | 120 | HP (*Clostridium perfringens* F262, 3e−69); bacteriophage Gp15 protein (*Pediococcus acidilactici* DSM 20284, 2e−04) | pfam06854, bacteriophage Gp15 protein |
| 18 | 10303_13515 | 1070 | Putative membrane protein (*Clostridium perfringens* B str. ATCC 3626, 0.0); phage tape measure minor tail protein (*Oenococcus oeni* AWRIB576, 3e−56) | COG5412, phage-related protein |
| 19 | 13528_13872 | 114 | HP (*Clostridium perfringens* ATCC 13124, 6e−74); Lj965 prophage protein (*Streptococcus pneumoniae* SPNA45, 6e−35) | |
| 20 | 13895_14161 | 88 | HP (*Clostridium perfringens* WAL-14572, 1e−54) | |
| 21 | 14228_14608 | 126 | HP (*Clostridium perfringens* WAL-14572, 1e−77); HP (*Clostridium* phage phiSM101, 3e−53) | |
| 22 | 14644_21261 | 2205 | KID repeat family protein (*Clostridium perfringens* B str. ATCC 3626, 0.0); phage minor structural protein (*Clostridium perfringens* WAL-14572, 0.0) | |
| 23 | 21282_21698 | 138 | Toxin secretion/phage lysis holin (*Clostridium perfringens* B str. ATCC 3626; 5e−92) | pfam05105, holin family |
| 24 | 21739_22155 | 138 | Conserved domain protein (*Clostridium perfringens* B str. ATCC 3626; 2e−83); cobalt ABC transporter, permease protein CbiQ (*Clostridium perfringens* C str. JGS1495, 2e−21) | |
| 25 | 22240_23373 | 377 | Putative N-acetylmuramoyl-L-alanine amidase (*Clostridium perfringens* F262, 0.0) | cd06583, peptidoglycan recognition proteins; pfam01510, N-acetylmuramoyl-L-alanine amidase; pfam08239, bacterial SH3 domain |
| 26 | 23503_24141 | 212 | HP (*Desulfosporosinus youngiae* DSM 17734, 3e−12); phage protein (*Clostridium difficile* ATCC 43255 1e−06] | |
| 27 | 24453_25733 | 426 | HP (*Lachnospiraceae bacterium* 9_1_43BFAA, 4e−53) | |
| 28 | 25702_26793 | 363 | HP (*Lachnospiraceae bacterium* 9_1_43BFAA, 2e−39) | |
| 29 | 26914_28881[e] | 655 | Resolvase, N domain protein (*Clostridium botulinum* Bf, 0.0) | cd03768, serine recombinase family; pfam00239, resolvase N terminal domain, pfam12844, helix-turn-helix domain |
| 30 | 28914_29342 | 142 | HP (*Clostridium perfringens* WAL-14572, 1e−86); phage repressor protein (*Clostridium botulinum* H04402 065, 4e−05) | pfam06114, DUF955; COG2856, predicted Zn peptidase |
| 31 | 29442_29879[e] | 145 | Helix-turn-helix domain protein (*Clostridium perfringens* E str. JGS1987, 5e−99); immunity repressor protein (phage-related protein) (*Lactobacillus plantarum* subsp. *plantarum* ST-III, 5e−12) | pfam01381, pfam13443, Cro/C1-type HTH DNA-binding domain |

TABLE 2-continued

Analysis of the ΦCP51 genome

| ORF | Location[a] | Size (aa)[b] | BlastP most significant match (organism, E value); top match showing possible function[c] | Domains |
|---|---|---|---|---|
| 32 | 30087_30281 | 64 | Putative DNA-binding protein (*Clostridium perfringens* E str. JGS1987, 4e−34) | pfam13443, Cro/C1-type HTH DNA-binding domain |
| 33 | 30459_30665 | 68 | HP (*Clostridium perfringens* E str. JGS1987, 2e−38) | |
| 34 | 30764_30943 | 59 | Conserved domain protein (*Clostridium perfringens* E str. JGS1987, 3e−32) | |
| 35 | 30957_31178 | 73 | HP (*Clostridium sporogenes* PA 3679, 7.4) | |
| 36 | 31171_31446[c] | 91 | HP (*Bacillus thuringiensis* serovar finitimus YBT-020, 4e−26); putative SinR-like protein (*Rhodobacter sphaeroides* 2.4.4, 2e−19) | |
| 37 | 31647_32201 | 184 | RNA polymerase sigma-B factor (*Clostridium perfringens* E str. JGS1987, 3e−128). | pfam04545, Sigma-70 region 4; pfam04542, Sigma-70 region 2; PRK05572, sporulation sigma factor SigF |
| 38 | 32212-32346 | 44 | HP (*Clostridium perfringens* WAL-14572, 6e−23); Gp33 protein (*Clostridium* phage phi3626, 2.8) | |
| 39 | 32365_33186 | 273 | Gp34 protein (*Clostridium perfringens* E str. JGS1987, 0.0); putative phage replisome organizer (*Clostridium botulinum* A2 str. Kyoto, 2e−35) | |
| 40 | 33158_33895 | 245 | Phage protein (*Clostridium perfringens* E str. JGS1987, 1e−180); DNA replication protein DnaC (*Caloramator australicus* RC3, 1e−54) | COG1484, DNA replication protein; c109099, P-loop_NTPase superfamily |
| 41 | 33955_34278 | 107 | HP (*Clostridium perfringens* WAL-14572, 2e−66) | |
| 42 | 34381_34656 | 91 | Gp41 protein (*Clostridium perfringens* E str. JGS1987, 3e−55); putative transcriptional regulator (*Clostridium* phage phiSM101, 2e−21) | pfam13545, Crp-like helix-turn-helix domain |
| 43 | 34665_34967 | 100 | Sporulation transcriptional regulator SpoIIID (*Clostridium perfringens* WAL-14572, 1e−61) | pfam12116, stage III sporulation protein D |
| 44 | 34972_35298 | 108 | HP (*Clostridium perfringens* WAL-14572, 1e−67); possible sigma factor (*Clostridium perfringens* E str. JGS1987, 6e−67) | |
| 45 | 35482_35946 | 154 | HP (*Clostridium perfringens* WAL-14572, 7e−60) | |
| 46 | 36202-36333 | 43 | HP (*Veillonella* sp., 9.3) | |
| 47 | 36390_36554 | 54 | GJ23454 (*Drosophila virilis*, 1.6) | |
| 48 | 36571_36966[c] | 131 | HP (*Desulfitobacterium hafniense* Y51, 2e−25) | |
| 49 | 37393_38052 | 219 | DNA integration/recombination/inversion protein (*Clostridium perfringens* E str. JGS1987, 1e−156) | cd01186, INT_SG3, DNA breaking-rejoining enzymes; pfam00589, phage integrase family |
| 50 | 38534-39094 | 186 | Transposon Tn21 resolvase (*Clostridium perfringens* E str. JGS1987, 3e−129) | cd03768, Serine Recombinase family; pfam00239, Resolvase, N terminal domain |

[a] c denotes reverse strand,
[b] amino acids,
[c] HP, hypothetical protein

The invention is further described by the following numbered paragraphs:

1. An isolated polypeptide comprising the amino acid sequence of SEQ ID NO: 1, or a fragment, variant, derivative or fusion thereof which is capable of binding specifically to and/or lysing cells of *Clostridium perfringens.*

2. A polypeptide according to Paragraph 1 wherein the fragment, variant, derivative or fusion thereof exhibits at least 60% identity to the amino acid sequence of SEQ ID NO: 1.

3. A polypeptide according to any one of the preceding paragraphs wherein the fragment, variant, derivative or fusion thereof is not a naturally occurring lysin of a bacteriophage of *Clostridium perfringens.*

4. An isolated polypeptide according to any one of the preceding paragraphs capable of binding specifically to cells of *Clostridium perfringens.*

5. An isolated polypeptide according to any one of the preceding paragraphs capable of lysing cells of *Clostridium perfringens.*

6. An isolated polypeptide according to any one of the preceding paragraphs capable of binding specifically to and lysing cells of *Clostridium perfringens.*

7. An isolated polypeptide according to any one of the preceding paragraphs comprising the amino acid sequence of SEQ ID NO: 1.

8. An isolated polypeptide according to Paragraph 7 consisting of the amino acid sequence of SEQ ID NO: 1.

9. An isolated polypeptide according to any one of the preceding paragraphs comprising or consisting of a fragment of the amino acid sequence of SEQ ID NO: 1.

10. An isolated polypeptide according to Paragraph 9 wherein the fragment comprises at least 50 contiguous amino acids of SEQ ID NO: 1, for example at least 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 366, 367, 368, 369, 370, 371, 372, 373, 374, 375 or 376 contiguous amino acids of SEQ ID NO: 1.

11. An isolated polypeptide according to Paragraph 9 or 10 wherein the fragment comprises or consists of the enzymatic (lytic) domain of SEQ ID NO: 1.

12. An isolated polypeptide according to any one of Paragraphs 9 to 11 wherein the fragment comprises or consists of the cell wall binding domain of SEQ ID NO: 1.

13. An isolated polypeptide according to any one of the preceding paragraphs comprising or consisting of a variant of the amino acid sequence of SEQ ID NO:1, or of a fragment thereof.

14. An isolated polypeptide according to Paragraph 13 wherein the variant comprises or consists of an amino acid sequence with at least 70% identity to the amino acid sequence of SEQ ID NO: 1, or to a fragment thereof, more preferably at least 80% or 85% or 90% identity to said sequence, and most preferably at least 95%, 96%, 97%, 98% or 99% identity to said amino acid sequence.

15. An isolated polypeptide according to any one of the preceding paragraphs comprising or consisting of a derivative of the amino acid sequence of SEQ ID NO:1, or of a fragment or variant thereof.

16. An isolated polypeptide according to any one of the preceding paragraphs comprising or consisting of a fusion of the amino acid sequence of SEQ ID NO: 1, or of a fragment, variant or derivative thereof.

17. An isolated polypeptide according to Paragraph 16 comprising or consisting of one or more additional amino acids inserted at the N- and/or C-termini of the amino acid sequence of SEQ ID NO: 1, or of a fragment, variant or derivative thereof.

18. An isolated polypeptide according to Paragraph 16 or 17 comprising or consisting of the cell wall binding domain of SEQ ID NO:1 and an enzymatic (lytic) domain different to that in SEQ ID NO: 1.

19. An isolated polypeptide according to any one of the preceding paragraphs wherein the polypeptide is capable of lysing cells of multiple strains of *Clostridium perfringens.*

20. An isolated polypeptide according to any one of the preceding paragraphs wherein the polypeptide is capable of lysing one or more cell types selected from the group consisting of cells of *Bacillus* sp. and other *Clostridium* sp.

21. An isolated peptide according to Paragraph 20 wherein the polypeptide is capable of lysing cells of *Bacillus* sp. selected from the group consisting of *Bacillus cereus* (e.g., *B. cereus* NCIMB 11796) and *B. subtilis* (e.g., *B. subtilis* ATCC 6633).

22. An isolated peptide according to Paragraph 20 wherein the polypeptide is capable of lysing cells of other *Clostridium* sp. selected from the group consisting of *C. acetobutylicum* (e.g., *C. acetobutylicum* BL75141), *C. bifermentans* (e.g., *C. ifermentans* NCTC 13019) and *C. beijerinckii* (e.g., *C. beijerinckii* NCIMB 8052).

23. An isolated polypeptide according to any one of the preceding paragraphs wherein the polypeptide is substantially incapable of lysing cells selected from the group consisting of *Anaerococcus hydrogenalis* DSMZ 7454, *Bacillus amyloliquefaciens* 0880, *Bifidobacterium adolescentis* DSMZ 20083, *Bifidobacterium angulatum* DSMZ 20098, *Bifidobacterium bifidum* DSMZ 20082, *Bifidobacterium longum* DSMZ 20219, *Bifidobacterium pseudocatenulatum* DSMZ 20438, *Clostridium cellobioparum* DSMZ 1351, *Clostridium coccoides* NCTC 11035, *Clostridium colinum* DSMZ 6011, *Clostridium difficile* NCTC 11204, *Clostridium innocuum* DSMZ 1286, *Clostridium leptum* DSMZ 753, *Clostridium nexile* DSMZ 1787, *Clostridium ramosum* DSMZ 1402, *Clostridium sordellii* NCTC 13356, *Clostridium sporogenes* ATCC 7886, *Clostridium tyrobutyricum* NCIMB 9582, *Enterococcus faecalis* FI10734, *Enterococcus hirae* FI10477, *Eubacterium barkeri* DSMZ 1223, *Lactobacillus casei* FI10736, *Lactobacillus johnsonii* FI9785, *Lactobacillus plantarum* FI08595, *Lactobacillus rhamnosus* FI10737, *Lactococcus lactis* MG1363, *Leuconostoc mesenteroides* subsp. *Mesenteroides* ATCC 8293, *Listeria innocua* NCTC 11288, *Listeria ivanovii* NCTC 11007, *Micrococcus luteus* FI10640, *Pediococcus pentosaceus* FI10642, *Pediococcus acidilactici* FI10738, *Salmonella enterica* serovar Typhimurium FI10739, *Salmonella enterica* serovar Enteritidis FI10113 and *Staphylococcus aureus* FI10139.

24. An isolated polypeptide according to any one of the preceding paragraphs wherein the polypeptide is capable of lysing cells of *Clostridium perfringens* NCTC 3110 and/or NCTC 8238.

25. An isolated polypeptide according to Paragraph 24 wherein the polypeptide exhibits at least 10% of the lysis activity of the polypeptide of SEQ ID NO: 1 on cells of *Clostridium perfringens* NCTC 3110 and/or NCTC 8238, for example at least 20%, 30%, 40%, 50%, 60%, 70%, 80%, 90%, 100% or more.

26. An isolated polypeptide according to Paragraph 25 wherein the polypeptide exhibits at least 100% of the lysis activity of the polypeptide of SEQ ID NO: 1 on cells of *Clostridium perfringens* NCTC 3110 and/or NCTC 8238, for example at least 120%, 130%, 140%, 150%, 160%, 170%, 180%, 190%, 200%, 250%, 300%, 500% or more.

27. An isolated polypeptide according to any one of the preceding paragraphs wherein the polypeptide is capable of lysing cells of pathogenic bacteria selectively.

28. An isolated polypeptide according to any one of the preceding paragraphs wherein the polypeptide is a recombinant polypeptide.

29. An isolated nucleic acid molecule encoding a polypeptide according to any one of Paragraphs 1 to 28.

30. A nucleic acid molecule according to Paragraph 29 wherein the nucleic acid molecule comprises or consists of the nucleotide sequence of SEQ ID NO: 2.

31. A vector comprising a nucleic acid molecule according to Paragraph 29 or 30.

32. A vector according to Paragraph 31 wherein the vector is an expression vector.

33. A vector according to Paragraph 31 or 32 wherein the vector is selected from the group consisting of pET15b and pACYC 184.

34. A host cell comprising a nucleic acid molecule according to Paragraph 29 or 30 or a vector according to any one of Paragraphs 31 to 33.

35. A host cell according to Paragraph 34 wherein the host cell is capable of expressing a polypeptide according to any one of Paragraphs 1 to 28.

36. A host cell according to Paragraph 34 or 35 wherein the host cell is a microbial cell.

37. A host cell according to any one of Paragraphs 34 to 36 wherein the host cell is a bacterial cell.

38. A host cell according to Paragraph 36 or 37 wherein the host cell is non-pathogenic.

39. A host cell according to any one of Paragraph 34 to 38 wherein the host cell is selected from the group consisting of cells of *Escherichia coli, Lactococcus* sp., *Bacteroides* sp, *Lactobacillus* sp., *Enterococcus* sp. and *Bacillus* sp.

40. A host cell according to Paragraph 38 wherein the host cell is a *Lactococcus lactis* or *Lactobacillus johnsonii* cell.

41. A host cell according to Paragraph 40 wherein the host cell is a *Lactococcus lactis* selected from the group consisting of *L. lactis* FI10676, *L. lactis* FI15876, *L. lactis* FI17847 and *L. lactis* UKLc10.

42. A host cell according to Paragraph 40 wherein the host cell is a *Lactobacillus johnsonii* selected from the group consisting of *L. johnsonii* FI9785, *L. johnsonii* FI10744, *L. johnsonii* FI10836 and *L. johnsonii* FI10844.

43. A method for producing a polypeptide according to any one of Paragraphs 1 to 28 comprising culturing a population of host cells comprising a nucleic acid molecule according to Paragraph 29 or 30 or a vector according to any one of Paragraphs 31 to 33 under conditions in which the polypeptide is expressed, and isolating the polypeptide therefrom.

44. A pharmacological composition comprising:
(a) a polypeptide according to any one of Paragraphs 1 to 28;
(b) a nucleic acid molecule according to Paragraph 29 or 30;
(c) a vector according to any one of Paragraphs 31 to 33;
(d) a host according to any one of Paragraphs 34 to 42; and/or
(e) a bacteriophage capable of expressing a polypeptide according to the first aspect of the invention; and a pharmaceutically acceptable carrier, diluent or excipient.

45. A pharmacological composition according to Paragraph 44 comprising a polypeptide according to any one of Paragraphs 1 to 28.

46. A pharmacological composition according to Paragraph 44 or 45 for oral administration.

47. A pharmacological composition according to Paragraph 44 to 46 wherein the polypeptide is microencapsulated.

48. A pharmacological composition according to any one of Paragraphs 44 to 47 capable of delivering the polypeptide to the GI tract.

49. A pharmacological composition according to any one of Paragraphs 44 to 48 comprising a nucleic acid molecule according to Paragraph 29 or 30 and/or a vector according any one of Paragraphs 31 to 33.

50. A pharmacological composition according to any one of Paragraphs 44 to 48 comprising a host cell according to any one of Paragraphs 34 to 42.

51. A pharmacological composition according to Paragraph 50 comprising a non-pathogenic bacterial host cell which is genetically engineered to express a polypeptide according to any one of Paragraphs 1 to 28 and to release said polypeptide upon reaching a predetermined location within the GI tract.

52. A pharmacological composition according to any one of Paragraphs 44 to 51 comprising a bacteriophage capable of expressing a polypeptide according to any one of Paragraphs 1 to 28.

53. A pharmacological composition according to any one of Paragraphs 44 to 52 wherein the composition allows sustained or slow-release of the polypeptide within the GI tract.

54. A polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28 for use in medicine.

55. Use of a polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28 in the preparation of a medicament for killing and/or inhibiting/preventing the growth of microbial cells in a patient, wherein the microbial cells are selected from the group consisting of *Clostridium perfringens* cells and other bacterial cells susceptible to lysis with said endolysin.

56. A polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28 for use in killing and/or inhibiting/preventing the growth of microbial cells in a patient, wherein the microbial cells are selected from the group consisting of *Clostridium perfringens* cells and other bacterial cells susceptible to lysis with said endolysin.

57. A method for killing and/or inhibiting/preventing the growth of microbial cells in a patient the method comprising administering to the patient a polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28, wherein the microbial cells are selected from the group consisting of *Clostridium perfringens* cells and other bacterial cells susceptible to lysis with said endolysin.

58. Use of a polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28 in the preparation of a medicament for the treatment or prevention of a disease or condition associated with microbial cells in a patient, wherein the microbial cells are selected from the group consisting of *Clostridium perfringens* cells and other bacterial cells susceptible to lysis with said endolysin.

59. A polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28 for use in the treatment or prevention of a disease or condition associated with microbial cells in a patient, wherein the microbial cells are selected from the group consisting of *Clostridium perfringens* cells and other bacterial cells susceptible to lysis with said endolysin.

60. A method for the treatment or prevention of a disease or condition associated with microbial cells in a patient the method comprising administering to the patient polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28, wherein the microbial cells are selected from the group consisting of *Clostridium perfringens* cells and other bacterial cells susceptible to lysis with said endolysin.

61. Use of a polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28 for killing and/or inhibiting/preventing the growth of microbial cells in vitro and/or ex vivo, wherein the microbial cells are selected from the group consisting of *Clostridium perfringens* cells and other bacterial cells susceptible to lysis with said endolysin.

62. The use according to Paragraph 55 or 58, the polypeptide, nucleic acid, vector, host or bacteriophage for use according to Paragraph 56 or 59 the method according to Paragraph 57 or 60 or the use according to Paragraph 61 wherein the microbial cells are selected from the group consisting of *Clostridium perfringens* cells and other bacterial cells susceptible to lysis upon contact with a polypeptide of SEQ I D NO: 1.

63. The use according to Paragraph 55, 58 or 62, the polypeptide, nucleic acid, vector, host or bacteriophage for use according to Paragraph 56, 59 or 62, or the method according to Paragraph 57, 60 or 62 or the use according to Paragraph 61 or 62 wherein the microbial cells are *Clostridium perfringens* cells.

64. The use according to Paragraph 55, 58, 62 or 63; the polypeptide, nucleic acid, vector, host or bacteriophage for use according to Paragraph 56, 59, 62 or 63; or the method according to Paragraph 57, 60, 62 or 63, wherein the microbial cells are selected from the group consisting of *Clostridium perfringens* cells and other bacterial cells susceptible to lysis with the endolysin of SEQ ID NO: 1.

65. The use according to Paragraph 55, 58 or 62 to 64; the polypeptide, nucleic acid, vector, host or bacteriophage for use according to Paragraph 56, 59 or 62 to 64; or the method according to Paragraph 57, 60 or 62 to 64, wherein the polypeptide, nucleic acid, vector, host cell, bacteriophage or pharmacological composition is for use in an organism belonging to a taxonomic superclass or class selected from the group consisting of Chondrichthyes (cartilaginous fish), Osteichthyes (bony fish), Actinopterygii (ray-finned bony fish), Sarcopterygii (lobe-finned fish), Tetrapoda (four-limbed vertebrates), Amphibia (amphibians), Reptilia (reptiles), Ayes (birds) and Mammalia (mammals).

66. The use according to Paragraph 55, 58 or 62 to 65; the polypeptide nucleic acid, vector, host or bacteriophage for use according to Paragraph 56, 59 or 62 to 65; or the method according to Paragraph 57, 60 or 62 to 65, wherein the taxonomic class is Aves (birds).

67. The use according to Paragraph 66; the polypeptide, nucleic acid, vector, host or bacteriophage for use according to Paragraph 66; or the method according to Paragraph 66, for use in poultry.

68. The use according to Paragraph 67; the polypeptide, nucleic acid, vector, host or bacteriophage for use according to Paragraph 67; or the method according to Paragraph 67, wherein the poultry is selected from the group consisting of chicken, duck, goose, ostrich, pigeon, turkey, pheasant, guinea fowl, partridge and quail.

69. The use according to Paragraph 55, 58 or 62 to 65; the polypeptide the nucleic acid, vector, host or bacteriophage for use according to Paragraph 56, 59 or 62 to 65; or the method according to Paragraph 57, 60 or 62 to 65 wherein the taxonomic class is Mammalia (mammals).

70. The use according to Paragraph 69; the polypeptide, nucleic acid, vector, host or bacteriophage for use according to Paragraph 69; or the method according to Paragraph 69, wherein the mammal is selected from the group consisting of alpaca, banteng, bison, camel, cat, cattle, deer, dog, donkey, gayal, goat, guinea pig, horse, llama, mule, pig, rabbit, reindeer, sheep, water buffalo, yak and human.

71. The use according to Paragraph 70; the polypeptide, nucleic acid, vector, host or bacteriophage for use according to Paragraph 70; or the method according to Paragraph 70, wherein the mammal is human.

72. The use according to Paragraph 55, 58 or 62 to 71; the polypeptide nucleic acid, vector, host or bacteriophage for use according to Paragraph 56, 59 or 62 to 71; or the method according to Paragraph 57, 60 or 62 to 71, for the treatment of an existing disease or condition.

73. The use according to Paragraph 55, 58 or 62 to 71; the polypeptide nucleic acid, vector, host or bacteriophage for use according to Paragraph 56, 59 or 62 to 71; or the method according to Paragraph 57, 60 or 62 to 71 for prophylaxis.

74. The use according to Paragraph 73; the polypeptide, nucleic acid, vector, host or bacteriophage for use according to Paragraph 73; or the method according to Paragraph 73, wherein the prophylaxis is primary or secondary prophylaxis.

75. The use according to Paragraph 74; the polypeptide, nucleic acid, vector, host or bacteriophage for use according to Paragraph 74; or the method according to Paragraph 74, wherein the prophylactic use is primary prophylaxis.

76. The use according to Paragraph 55, 58 or 62 to 75; the polypeptide nucleic acid, vector, host or bacteriophage for use according to Paragraph 56, 59 or 62 to 75; or the method according to Paragraph 57, 60 or 62 to 75, wherein the polypeptide, nucleic acid, vector, host cell, bacteriophage or pharmacological composition is administered as a single dose.

77. The use according to Paragraph 55, 58 or 62 to 75; the polypeptide nucleic acid, vector, host or bacteriophage for use according to Paragraph 56, 59 or 62 to 75; or the method according to Paragraph 57, 60 or 62 to 75, wherein the polypeptide, nucleic acid, vector, host cell, bacteriophage or pharmacological composition is administered as a plurality of doses (for example, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more doses).

78. The use according to Paragraph 77; the polypeptide, nucleic acid, vector, host or bacteriophage for use according to Paragraph 77; or the method according to Paragraph 77, wherein the polypeptide, nucleic acid, vector, host cell, bacteriophage or pharmacological composition is administered in a frequency such that the polypeptide according to any one of Paragraphs 1-27 is continuously present in the GI tract of the patient.

79. The use according to Paragraph 55, 58 or 62 to 78; the polypeptide nucleic acid, vector, host or bacteriophage for use according to Paragraph 56, 59 or 62 to 78; or the method according to Paragraph 57, 60 or 62 to 78, wherein the polypeptide, nucleic acid, vector, host cell, bacteriophage or pharmacological composition is administered in a frequency sufficient to prevent occurrence or recurrence of a disease or condition associated with microbial cells in a patient, wherein the microbial cells are selected from the group consisting of *Clostridium perfringens* cells and other bacterial cells susceptible to lysis with endolysin of SEQ I D NO: 1.

80. The polypeptide, nucleic acid, vector, host cell, bacteriophage or pharmacological composition for use according to Paragraph 15 wherein the polypeptide, nucleic acid, vector, host cell, bacteriophage or pharmacological composition is administered in a frequency sufficient to prevent occurrence or recurrence of a disease or condition associated with microbial cells in a patient, wherein the microbial cells are selected from the group consisting of *Clostridium perfringens* cells.

81. The use according to Paragraph 55, 58 or 62 to 80; the polypeptide nucleic acid, vector, host or bacteriophage for use according to Paragraph 56, 59 or 62 to 80; or the method according to Paragraph 57, 60 or 62 to 80, wherein the polypeptide, nucleic acid, vector, host cell, bacteriophage or pharmacological composition is a host cell or pharmacological composition comprising the same.

82. The use according to Paragraph 55, 58 or 62 to 80; the polypeptide nucleic acid, vector, host or bacteriophage for use according to Paragraph 56, 59 or 62 to 80; or the method according to Paragraph 57, 60 or 62 to 80, wherein the polypeptide, nucleic acid, vector, host cell, bacteriophage or pharmacological composition is a host cell.

83. A kit for detecting the presence of microbial cells in a sample, the kit comprising a polypeptide according to any one of Paragraphs 1 to 27, a nucleic acid molecule according to Paragraph 27 or 28, a vector according to any one of Paragraphs 29 to 31 or a host according to any one of Paragraphs 32 to 39, a bacteriophage capable of expressing a polypeptide according to any one of Paragraphs 1 to 27, wherein the microbial cells are selected from the group consisting of *Clostridium perfringens* cells and other bacterial cells susceptible to lysis with said endolysin.

84. The kit according to Paragraph 83 wherein the microbial cells are *Clostridium perfringens* cells.

85. The kit according to Paragraph 83 or 84 wherein the microbial cells are *Clostridium perfringens* NCTC 3110 and/or NCTC 8238 cells.

86. The kit according to any one of Paragraphs 83 to 85 wherein the polypeptide is immobilised on a surface.

87. The kit according to any one of Paragraphs 83 to 86 wherein the sample is a cell sample.

88. The kit according to any one of Paragraphs 83 to 87 wherein the sample is derived from a swab taken from a surface to be tested for contamination with microbial cells.

89. The kit according to any one of Paragraphs 83 to 88 further comprising a negative control sample.

90. The kit according to any one of Paragraphs 83 to 89 further comprising a positive control sample.

91. Use of a polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28, in the preparation of a diagnostic agent for a disease or condition associated with microbial cells selected from the group consisting of *Clostridium perfringens* cells and other bacterial cells susceptible to lysis with said endolysin.

92. A polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28 for use in the diagnosis of a disease or condition associated with microbial cells selected from the group consisting of *Clostridium perfringens* cells and other bacterial cells susceptible to lysis with said endolysin.

93. Use of a polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28, for detecting the presence of microbial cells in a sample in vitro and/or ex vivo, wherein the microbial cells selected from the group consisting of *Clostridium perfringens* cells and other bacterial cells susceptible to lysis with said endolysin.

94. A method for the diagnosis of a disease or condition associated with microbial cells in a patient, the method comprising contacting a cell sample from a patient to be tested with a polypeptide according to any one of Paragraphs 1 to 28, a nucleic acid molecule according to Paragraph 29 or 30, a vector according to any one of Paragraphs 31 to 33 or a host according to any one of Paragraphs 34 to 42, or a bacteriophage capable of expressing a polypeptide according to any one of Paragraphs 1 to 28, and determining whether the cells in the sample have been lysed thereby, wherein the microbial cells are selected from the group consisting of *Clostridium perfringens* cells and other bacterial cells susceptible to lysis with said endolysin.

95. The use according to Paragraph 91, polypeptide for use according to Paragraph 92, use according to Paragraph 93 or method according to Paragraph 94 wherein the microbial cells are *Clostridium perfringens* cells.

96. The use according to Paragraph 91, polypeptide for use according to Paragraph 92, use according to Paragraph 93 or method according to Paragraph 94 wherein the microbial cells are *Clostridium perfringens* NCTC 3110 and/or NCTC 8238 cells.

97. An isolated polypeptide substantially as herein described with reference to the examples.

98. An isolated nucleic acid molecule substantially as herein described with reference to the examples.

99. A vector substantially as herein described with reference to the examples.

100. A host cell substantially as herein described with reference to the examples.

101. A method for producing a polypeptide substantially as herein described with reference to the examples.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated nucleic acid molecule encoding a fusion polypeptide,
wherein the fusion polypeptide comprises: i) a polypeptide having endolysin activity and comprising an amino acid sequence that has at least 90% sequence identity to the amino acid sequence of amino acids 18 to 134 of SEQ ID NO: 1; and ii) a polypeptide that is heterologous to the polypeptide of i).

2. The nucleic acid molecule according to claim 1 wherein the nucleic acid molecule comprises or consists of the nucleotide sequence of SEQ ID NO: 2.

3. A vector comprising the nucleic acid molecule according to claim 1.

4. The vector according to claim 3 wherein the vector is an expression vector.

5. The vector according to claim 3 wherein the vector is selected from the group consisting of pET15b and pACY184.

6. A bacterial host cell comprising the nucleic acid molecule according to claim 1.

7. The host cell according to claim 6 wherein the host cell is capable of expressing the fusion polypeptide.

8. The host cell according to claim 6 wherein the host cell is non-pathogenic.

9. The host cell according to claim 6 wherein the host cell is selected from the group consisting of cells of *Escherichia coli*, *Lactococcus* sp., *Bacteroides* sp., *Lactobacillus* sp., *Enterococcus* sp. and *Bacillus* sp.

10. The host cell according to claim 8 wherein the host cell is a *Lactococcus lactis* or *Lactobacillus johnsonii* cell.

11. The host cell according to claim 10 wherein the host cell is a *Lactococcus lactis* cell selected from the group consisting of *L. lactis* FI10676 and *L. lactis* UKLc10.

12. The host cell according to claim 10 wherein the host cell is a *Lactobacillus johnsonii* cell selected from the group consisting of *L. johnsonii* FI9785 and *L. johnsonii* FI10744.

13. An expression vector comprising a heterologous nucleic acid molecule encoding a polypeptide, wherein the polypeptide has endolysin activity and comprises an amino acid sequence that has at least 90% sequence identity to the amino acid sequence of amino acids 18 to 134 of SEQ ID NO: 1.

14. The expression vector according to claim 13 wherein the expression vector is selected from the group consisting of pET15b and pACY184.

15. A bacterial host cell comprising the expression vector according to claim 13.

16. The host cell according to claim 15 wherein the host cell is capable of expressing the polypeptide.

17. The host cell according to claim 15 wherein the host cell is non-pathogenic.

18. The host cell according to claim 15 wherein the host cell is selected from the group consisting of cells of *Escherichia coli*, *Lactococcus* sp., *Bacteroides* sp., *Lactobacillus* sp., *Enterococcus* sp. and *Bacillus* sp.

19. The host cell according to claim 18 wherein the host cell is a *Lactococcus lactis* or *Lactobacillus johnsonii* cell.

20. The host cell according to claim 19 wherein the host cell is a *Lactococcus lactis* cell selected from the group consisting of *L. lactis* FI10676 and *L. lactis* UKLc10.

21. The host cell according to claim 19 wherein the host cell is a *Lactobacillus johnsonii* cell selected from the group consisting of *L. johnsonii* FI9785 and *L. johnsonii* FI10744.

22. A non-pathogenic bacterial host cell comprising a heterologous nucleic acid molecule encoding a polypeptide, wherein the polypeptide has endolysin activity and comprises an amino acid sequence that has at least 90% sequence identity to the amino acid sequence of amino acids 18 to 134 of SEQ ID NO: 1.

23. The host cell according to claim 22 wherein the nucleic acid molecule comprises an expression vector selected from the group consisting of pET15b and pACY184.

24. The host cell according to claim 22 wherein the host cell is capable of expressing the polypeptide.

25. The host cell according to claim 22 wherein the host cell is selected from the group consisting of cells of *Escherichia coli*, *Lactococcus* sp., *Bacteroides* sp., *Lactobacillus* sp., *Enterococcus* sp. and *Bacillus* sp.

26. The host cell according to claim 25 wherein the host cell is a *Lactococcus lactis* or *Lactobacillus johnsonii* cell.

27. The host cell according to claim 26 wherein the host cell is a *Lactococcus lactis* cell selected from the group consisting of *L. lactis* FI10676 and *L. lactis* UKLc10.

28. The host cell according to claim 26 wherein the host cell is a *Lactobacillus johnsonii* cell selected from the group consisting of *L. johnsonii* FI9785 and *L. johnsonii* FI10744.

29. The nucleic acid molecule according to claim 1, wherein the fusion polypeptide further comprises an amino acid sequence that has at least 90% sequence identity to the amino acid sequence of amino acids 322 to 375 of SEQ ID NO: 1.

30. The nucleic acid molecule according to claim 1, wherein the fusion polypeptide further comprises an amino acid sequence that has at least 90% sequence identity to the amino acid sequence of amino acids 135 to 321 of SEQ ID NO: 1.

31. The nucleic acid molecule according to claim 1, wherein the polypeptide having endolysin activity comprises the amino acid sequence of SEQ ID NO: 1 and the fusion polypeptide is capable of binding specifically to cells of *Clostridium perfringens* and/or lysing cells of *Clostridium perfringens*.

32. The expression vector according to claim 13, wherein the polypeptide further comprises an amino acid sequence that has at least 90% sequence identity to the amino acid sequence of amino acids 322 to 375 of SEQ ID NO: 1.

33. The expression vector according to claim 13, wherein the polypeptide further comprises an amino acid sequence that has at least 90% sequence identity to the amino acid sequence of amino acids 135 to 321 of SEQ ID NO: 1.

34. The expression vector according to claim 13, wherein the polypeptide comprises the amino acid sequence of SEQ ID NO: 1 and is capable of binding specifically to cells of *Clostridium perfringens* and/or lysing cells of *Clostridium perfringens*.

35. The host cell according to claim 22, wherein the polypeptide further comprises an amino acid sequence that has at least 90% sequence identity to the amino acid sequence of amino acids 322 to 375 of SEQ ID NO: 1.

36. The host cell according to claim 22, wherein the polypeptide further comprises an amino acid sequence that has at least 90% sequence identity to the amino acid sequence of amino acids 135 to 321 of SEQ ID NO: 1.

37. The host cell according to claim 22, wherein the polypeptide comprises the amino acid sequence of SEQ ID NO: 1 and is capable of binding specifically to cells of *Clostridium perfringens* and/or lysing cells of *Clostridium perfringens*.

* * * * *

SEQUENCE LISTING

```
<160> NUMBER OF SEQ ID NOS: 19

<210> SEQ ID NO 1
<211> LENGTH: 377
<212> TYPE: PRT
<213> ORGANISM: Clostridium perfringens

<400> SEQUENCE: 1

Met Tyr Ile Asn Gln Ser Asn Ile Lys Phe Asn Gly Leu Arg Tyr Gly
1               5                   10                  15

Asn Asp Pro Asn Lys Ile Ile Ile His Asn Ala Asp Ala Thr Ser Cys
            20                  25                  30

Ser Val Tyr Asp Ile Asp Arg Trp His Lys Gly Asn Gly Trp Ser Gly
        35                  40                  45

Ile Gly Tyr Asp Tyr Phe Ile Arg Lys Glu Gly Ser Val Trp Thr Gly
    50                  55                  60

Arg Pro Glu Asn Ala Ile Gly Ala His Thr Ile Gly Gln Asn Ser Ser
65                  70                  75                  80

Ser Ile Gly Ile Cys Leu Glu Gly Ala Phe Met Arg Glu Lys Pro Thr
                85                  90                  95

Arg Ala Gln Leu Asn Ser Leu Tyr Glu Leu Ile Ala Asp Ile Arg Ala
            100                 105                 110

Arg Arg Gly Asn Leu Pro Val Tyr Gly His Lys Asp Phe Asn Asn Thr
        115                 120                 125

Asp Cys Pro Gly Ile Asn Phe Pro Leu Glu Gln Phe Lys Asn Asn Ser
    130                 135                 140

Tyr Arg Pro Thr Gly Gly Glu Ile Val Ser Asp Asn Gly Phe Tyr Arg
145                 150                 155                 160

Ser Asp Glu Glu Arg Thr Asn Ala Thr Ile Val Gly Glu Gly Asn Ile
                165                 170                 175

Glu Val Leu Asp Lys Asn Cys Lys Val Ile Glu Asn Arg Tyr Ile Ser
            180                 185                 190

Ser Leu Asp Arg Val Phe Val Leu Gly Ile Tyr Pro Ala Ser Lys Tyr
        195                 200                 205

Ile Glu Ile Ile Tyr Pro Ala Gly Asn Glu Lys Tyr His Ala Tyr Ile
    210                 215                 220

Ser Ile Glu Asn Tyr Ser Arg Ile Ser Phe Asp Tyr His Met Gln Tyr
225                 230                 235                 240

Lys Asn Asp Asn Gly Val Thr Tyr Val Trp Trp Asp Ser Glu Asp Val
                245                 250                 255

Asn Val Lys Glu His Asn Glu Glu Leu Gln Ala Asn Gln Lys Ala Ser
            260                 265                 270

Pro Met Tyr Arg Val Gly Lys Trp Leu Arg Val Thr Phe Tyr Arg Thr
        275                 280                 285

Asp Gly Thr Pro Ser Asp Gly Phe Val Arg Tyr Glu Gly Glu Gln Ala
    290                 295                 300

Val Lys Phe Tyr Glu Glu Glu Lys Ile Lys Glu Gly Ile Val Lys Val
```

```
                305                 310                 315                 320
Asn Thr Tyr Leu Asn Val Arg Asp Ser Ile Asn Gly Asn Ile Ile Gly
                    325                 330                 335

Lys Val Phe Asn Gly Glu Glu Val Ser Ile Ile Trp Thr Lys Asp Gly
                340                 345                 350

Trp Tyr Tyr Ile Asp Tyr Asn Thr Asn His Gly Lys Lys Arg Gly Tyr
            355                 360                 365

Val Ser Ser Lys Tyr Val Glu Glu Val
            370                 375

<210> SEQ ID NO 2
<211> LENGTH: 1134
<212> TYPE: DNA
<213> ORGANISM: Artificial Sequence
<220> FEATURE:
<223> OTHER INFORMATION: Sequence encoding endolysin (CP51L) of
      bacteriophage N&CP51 of Clostridium perfringens

<400> SEQUENCE: 2
atgtatataa atcaatcaaa tattaaattc aatggattaa gatatggaaa tgatcctaat      60
aaaataatta ttcataatgc agatgcaact tcatgtagtg tatatgatat agatagatgg     120
cataaaggaa atggatggag tggcataggc tatgattatt ttattagaaa agagggttca     180
gtttggactg gtagaccaga aaatgcaata ggagctcaca caataggtca aaacagttca     240
agtataggaa tttgcttaga aggggctttc atgagagaaa accaactag agcacaatta      300 aattctcttt atgagttaat tgcagatatt agagctagaa gaggtaactt acctgtatat     360
ggacataagg attttaataa tacagattgt ccaggaataa acttcccact agagcaattt     420
aaaaataatt catatagacc aactggagga gaaatagtat cagataatgg ctttttataga    480 agtgatgaag aaagaacaaa tgctacaata gttggggaag aaatattga agtattagat      540 aaaaattgta agttattga gaatagatat atatctagtt tggatagagt ttttgtatta      600
ggaatatatc cagcatctaa atatatagaa ataatttatc cagcaggaaa tgaaaaatat     660
catgcatata tttctataga aaactacagt agaatatctt ttgactacca tatgcaatat    720
aaaaatgata atggagttac ttatgtgtgg tgggattcag aggatgttaa tgttaaagag     780
cataatgaag aattacaggc gaatcaaaaa gcttctccaa tgtatagagt tggaaaatgg     840
ctaagagtaa cttttatag aactgatggt actccaagtg atggatttgt tcgttatgaa      900
ggagagcaag ctgtaaagtt ttatgaagag gaaaaaatta agagggtat agttaaagtt     960 aatacttatc ttaatgttag agatagtata aatggaaata ataggaaaa ggtatttaat    1020 ggtgaagaag tttcaataat atggactaaa gatgggtggt attacataga ttacaataca    1080
aatcacggaa agaaaagagg atatgtaagt tctaaatatg tagaagaagt atag          1134

<210> SEQ ID NO 3
<211> LENGTH: 138
<212> TYPE: PRT
<213> ORGANISM: Artificial Sequence
<220> FEATURE:
<223> OTHER INFORMATION: holin of N&CP51

<400> SEQUENCE: 3

Met Glu Asn Ile Phe Asp Tyr Leu Lys Met Gly Ile Val Ala Ile Gly
1               5                   10                  15

Thr Leu Phe Thr Trp Leu Leu Gly Ala Trp Asp Thr Pro Leu Val Ile
            20                  25                  30
```

```
Leu Ile Val Leu Met Ala Leu Asp Tyr Ile Thr Gly Ile Thr Lys Gly
         35                  40                  45
Tyr Val Asn Lys Asp Leu Ser Ser Asn Ile Gly Leu Lys Gly Ile Ala
 50                  55                  60
Arg Lys Gly Val Ile Phe Thr Ile Leu Ile Val Ala Val Met Leu Asp
 65                  70                  75                  80
Arg Leu Leu Asn Thr Gly Asn Trp Ile Phe Arg Thr Leu Val Cys Tyr
                 85                  90                  95
Phe Tyr Ile Ala Asn Glu Gly Ile Ser Ile Ile Glu Asn Ala Ser Glu
                100                 105                 110
Leu Gly Val Pro Val Pro Ser Lys Leu Lys Asn Ala Leu Ile Gln Leu
            115                 120                 125
Lys Glu Asp Lys Glu Asp His Lys Lys Leu
130                 135

<210> SEQ ID NO 4
<211> LENGTH: 11
<212> TYPE: DNA
<213> ORGANISM: Artificial Sequence
<220> FEATURE:
<223> OTHER INFORMATION: 11 bp core region of N&CP51 prophage genome

<400> SEQUENCE: 4
ctggacatgc t                                                          11

<210> SEQ ID NO 5
<211> LENGTH: 24
<212> TYPE: DNA
<213> ORGANISM: Artificial Sequence
<220> FEATURE:
<223> OTHER INFORMATION: Primer to amplify part of N&CP51 prophage
      genome

<400> SEQUENCE: 5
atagatctta taacgtctct cttg                                            24

<210> SEQ ID NO 6
<211> LENGTH: 22
<212> TYPE: DNA
<213> ORGANISM: Artificial Sequence
<220> FEATURE:
<223> OTHER INFORMATION: Primer to amplify part of N&CP51 prophage
      genome

<400> SEQUENCE: 6
tcacctatag ttttatttgg aa                                              22

<210> SEQ ID NO 7

<400> SEQUENCE: 7

000

<210> SEQ ID NO 8
<211> LENGTH: 27
<212> TYPE: DNA
<213> ORGANISM: Artificial Sequence
<220> FEATURE:
<223> OTHER INFORMATION: Primer to amplify endolysin gene of N&CP51

<400> SEQUENCE: 8
gaatgtcata tgtatataaa tcaatca                                         27
```

-continued

<210> SEQ ID NO 9
<211> LENGTH: 24
<212> TYPE: DNA
<213> ORGANISM: Artificial Sequence
<220> FEATURE:
<223> OTHER INFORMATION: Primer to amplify endolysin gene of N&CP51

<400> SEQUENCE: 9
actcgaggtg ggataattcc tacc 24

<210> SEQ ID NO 10
<211> LENGTH: 24
<212> TYPE: DNA
<213> ORGANISM: Artificial Sequence
<220> FEATURE:
<223> OTHER INFORMATION: Primer to amplify endolysin gene of N&CP51

<400> SEQUENCE: 10
tattgcatgt ggtagtcaaa agat 24

<210> SEQ ID NO 11
<211> LENGTH: 27
<212> TYPE: DNA
<213> ORGANISM: Artificial Sequence
<220> FEATURE:
<223> OTHER INFORMATION: Primer to amplify endolysin gene of N&CP51

<400> SEQUENCE: 11
ttgactacca catgcaatat aaaaatg 27

<210> SEQ ID NO 12
<211> LENGTH: 27
<212> TYPE: DNA
<213> ORGANISM: Artificial Sequence
<220> FEATURE:
<223> OTHER INFORMATION: Primer to amplify nisRK from L. lactis FI5876

<400> SEQUENCE: 12
cccgggagaa tcttaaagag tctaggg 27

<210> SEQ ID NO 13
<211> LENGTH: 23
<212> TYPE: DNA
<213> ORGANISM: Artificial Sequence
<220> FEATURE:
<223> OTHER INFORMATION: Primer to amplify nisRK from L. lactis FI5876

<400> SEQUENCE: 13
aaaaagtaat ccttagagat tac 23

<210> SEQ ID NO 14
<211> LENGTH: 377
<212> TYPE: PRT
<213> ORGANISM: Clostridium perfringens

<400> SEQUENCE: 14

```
Met Tyr Ile Asn Gln Ser Asn Ile Lys Phe Asn Gly Leu Asn Tyr Gly
1               5                   10                  15

Asn Asn Pro Asn Lys Ile Ile Ile His Asn Ala Asp His Pro Asn Cys
            20                  25                  30

Ser Val Tyr Asp Val Asp Arg Trp His Lys Gly Asn Gly Trp Ser Gly
        35                  40                  45

Ile Gly Tyr His Tyr Phe Ile Arg Lys Asp Gly Ser Val Trp Thr Gly
    50                  55                  60
```

Arg Pro Glu Asn Ala Lys Gly Ala His Thr Ile Gly Gln Asn Ser Ser
 65                  70                  75                  80

Ser Ile Gly Ile Cys Leu Glu Gly Ala Leu Met Arg Glu Lys Pro Thr
             85                  90                  95

Arg Ala Gln Leu Asn Ser Leu Tyr Tyr Leu Ile Ala Asp Ile Arg Ala
            100                 105                 110

Arg Arg Gly Asn Leu Pro Val Tyr Gly His Lys Asp Phe Asn Asn Thr
        115                 120                 125

Asp Cys Pro Gly Ala Asn Phe Pro Leu Glu Gln Phe Lys Asn Asn Ser
    130                 135                 140

Tyr Arg Pro Thr Gly Gly Thr Glu Ile Val Ser Asp Asn Gly Phe Tyr
145                 150                 155                 160

Ile Ser Asn Glu Glu Arg Glu Asn Ala Thr Ile Val Gly Gly Gly Asn
                165                 170                 175

Ile Glu Val Leu Asp Glu Lys Gly Asn Val Ile Gln Gly Arg His Ile
            180                 185                 190

Ser Ser Leu Asp Arg Val Phe Val Leu Gly Ile Tyr Pro Ser Arg Asn
        195                 200                 205

His Ile Glu Leu Ile Tyr Pro Gly Lys Asp Glu Lys Tyr His Ala Tyr
    210                 215                 220

Ile Ser Ile Glu Asn Tyr Ser Arg Leu Ser Phe Asp Tyr His Met Gln
225                 230                 235                 240

Tyr Lys Asn Asp Asp Gly Val Thr Tyr Val Trp Trp Asp Ser Lys Asn
                245                 250                 255

Val Asn Val Lys Asp His Asp Glu Glu Leu Gln Pro His Gln Lys Ala
            260                 265                 270

Ser Pro Met Tyr Arg Thr Asn Gly Trp Leu Arg Ile Thr Phe Tyr Arg
        275                 280                 285

Glu Asp Gly Thr Pro Ser Asp Gly Tyr Val Arg Tyr Glu Gly Glu Gln
    290                 295                 300

Lys Glu Arg Phe Tyr Arg Lys Gly Lys Val Val Asn Val Arg Thr Ser
305                 310                 315                 320

Leu Thr Val Arg Ala Gly Ala Gly Thr Asn Tyr Ser Ala Ile Gly Ser
                325                 330                 335

Leu Glu Pro Asn Glu Asn Val Asp Ile Leu Gly Lys Ala Glu Gly Trp
            340                 345                 350

Tyr Tyr Val Glu Tyr Asn Thr Lys Asn Glu Arg Lys Arg Gly Tyr Val
        355                 360                 365

Ser Glu Lys Tyr Ile Glu Ile Ile Gln
    370                 375

<210> SEQ ID NO 15
<211> LENGTH: 392
<212> TYPE: PRT
<213> ORGANISM: Clostridium perfringens

<400> SEQUENCE: 15

Met Asn Ile Lys Thr Asp Leu Thr Ser Val Asn Tyr Arg Asn Gly Arg
1               5                   10                  15

Asn Gly Asn Ser Ile Asp Tyr Ile Val Cys His Phe Thr Gly Asn Gln
            20                  25                  30

Asn Asp Lys Ala Ser Gly Asn Ala Asn Tyr Phe Arg Cys Val Asn Arg
        35                  40                  45

Gln Ala Ser Ala His Tyr Phe Val Asp Asp Asn Glu Ile Val Gln Val
    50                  55                  60

Val Arg Glu Gly Asp Thr Ser Trp His Cys Gly Asp Gly Asn Gly Arg
 65                  70                  75                  80

Tyr Gly Ile Thr Asn Ser Asn Ser Ile Gly Ile Glu Met Cys Ala Thr
                 85                  90                  95

Asn Gly Asp Ile Ser Glu Lys Thr Ile Glu Asn Thr Leu Trp Leu Val
            100                 105                 110

Lys Ser Leu Met Asn Lys Tyr Gly Ile Asp Ile Asp His Val Val Arg
        115                 120                 125

His Tyr Asp Ala Ser Arg Lys Cys Cys Pro Ser Pro Phe Ser Pro Asn
    130                 135                 140

Asn Trp Ser Arg Trp Trp Glu Phe Lys Glu Arg Leu Lys Gly Thr Val
145                 150                 155                 160

Glu Asn Ile Glu Val Thr Thr Gln Ser Thr Asn Gly Phe Tyr Glu Ser
                165                 170                 175

Asp Ile Glu Lys Thr Asn Ala Thr Ile Val Gly Leu Gly Asp Ile Glu
            180                 185                 190

Val Leu Asn Asp Lys Cys Glu Val Ile Lys Asp Arg Tyr Ile Ser Ser
        195                 200                 205

Leu Asp Arg Ile Tyr Val Leu Gly Ile Tyr Pro Ser Arg Asn Phe Ile
210                 215                 220

Glu Val Ile Tyr Gln Gly Lys Asp Lys Tyr His Ala Tyr Ile Asp
225                 230                 235                 240

Ile Lys Tyr Tyr Ser Arg Ile Ser Phe Asp Phe His Met Gln Tyr Gln
                245                 250                 255

Asn Asp Asp Gly Asp Thr Tyr Val Trp Trp Ser Ser Lys Asp Val Asn
            260                 265                 270

Lys Thr Glu Pro Asn Glu Ile Leu Ser Pro Asn Lys Lys Ala Ser Pro
        275                 280                 285

Met Tyr Arg Glu Asn Gly Trp Leu Arg Ile Thr Phe Tyr Arg Asp Asn
    290                 295                 300

Gly Val Ala Thr Asp Gly Phe Val Arg Tyr Glu Gly Glu Gln Ser Val
305                 310                 315                 320

Lys Phe Tyr Glu Glu Gly Lys Ile Lys Asp Gly Ile Val Lys Val Asn
                325                 330                 335

Thr Tyr Leu Asn Val Arg Asp Ser Ile Cys Gly Asn Ile Ile Gly Lys
            340                 345                 350

Val Phe Asn Gly Glu Glu Val Ser Ile Trp Thr Lys Asp Gly Trp
        355                 360                 365

Tyr Tyr Ile Glu Tyr Asn Thr Asn His Gly Lys Lys Arg Gly Tyr Val
370                 375                 380

Ser Ser Lys Tyr Val Glu Glu Val
385                 390

<210> SEQ ID NO 16
<211> LENGTH: 389
<212> TYPE: PRT
<213> ORGANISM: Clostridium perfringens

<400> SEQUENCE: 16

Met Lys Ile Asn Lys Arg Leu Ser Thr Thr Asn Val Thr Leu Asn Ala
1               5                   10                  15

Asn Asn Pro Lys His Ile Ile His Glu Thr Asp Asn Thr Ser Lys
            20                  25                  30

Gly Ala Gly Ala Glu Thr His Cys Lys Ala Gln Ala Asn Gly Asn Ile

```
                35                  40                  45
Gly Lys Ala Ser Val His Tyr Tyr Val Asp Asp Thr Gly Val Tyr Gln
 50                  55                  60

Ala Val Glu His Lys His Ala Thr Trp Asn Cys Gly Asp Gly Asn Asn
 65                  70                  75                  80

Arg Tyr Gly Ile Asn Asn Lys Asn Thr Ile Ser Ile Glu Ile Cys Val
                 85                  90                  95

Asn Ser Asp Ser Asp Tyr Asn Lys Ala Val Asp Asn Thr Val Glu Leu
            100                 105                 110

Val Arg Tyr Leu Lys Asn Gly Tyr Tyr Ser Asn Cys Gln Val Val Arg
        115                 120                 125

His Tyr Asp Ala Ser Arg Lys Asn Cys Pro Arg Arg Ile Leu Ala Asn
    130                 135                 140

Gly Tyr Trp Asn Thr Phe Leu Glu Arg Val Asn Ser Lys Asp Ser Ser
145                 150                 155                 160

Ser Gln Thr Pro Ala Asn Thr Ser Tyr Lys Gly Phe Tyr Glu Ser Ser
                165                 170                 175

Glu Thr Arg Thr Asn Ala Thr Leu Val Gly Glu Gly Ser Ile Lys Val
            180                 185                 190

Leu Asp Glu Glu Cys Asn His Val Ser Gly Arg Trp Ile Asp Ser Leu
        195                 200                 205

Asp Arg Leu Phe Val Ile Gly Ile Tyr Pro Ser Arg Lys Phe Ile Glu
    210                 215                 220

Val Val Tyr Pro Ala Gly Asp Lys Lys Tyr His Ala Tyr Ile Gly Ile
225                 230                 235                 240

Glu Tyr Tyr Asn Arg Ile Leu Phe Asp Tyr His Lys Glu Tyr Ile Asn
                245                 250                 255

Asp Asp Gly Val Thr Tyr Val Trp Trp Asn Ala Ser Asp Val Asn Val
            260                 265                 270

Lys Asp His Asn Glu Glu Leu Gln Pro Asn Gln Lys Ala Ser Pro Met
        275                 280                 285

Tyr Arg Thr Gly Glu Trp Leu Arg Ile Thr Phe Tyr Arg Glu Asn Gly
    290                 295                 300

Ile Pro Ser Asp Gly Tyr Val Arg Tyr Glu Gly Ser Gln Asn Lys Lys
305                 310                 315                 320

Phe Tyr Glu Asn Ile Gln Tyr Gly Ile Val Lys Val Asn Ser Ser Leu
                325                 330                 335

Asn Val Arg Glu Asn Pro Asn Gly Glu Val Ile Gly Ser Val Tyr Lys
            340                 345                 350

Asp Glu Lys Val Gln Val Leu Lys Glu Glu Asn Gly Trp Cys Tyr Ile
        355                 360                 365

Glu Tyr Ser Thr Ser Lys Gly Glu Lys Arg Gly Tyr Val Ser Ser Lys
    370                 375                 380

Tyr Ile Glu Leu Val
385

<210> SEQ ID NO 17
<211> LENGTH: 349
<212> TYPE: PRT
<213> ORGANISM: Clostridium perfringens

<400> SEQUENCE: 17

Met Lys Ile Ala Val Arg Gly Gly His Asn Phe Gln Ala Lys Gly Ala
 1               5                  10                  15
```

```
Ser Ala Leu Ile Asp Glu Thr Ile Glu Asp Arg Lys Val Lys Asp Ser
             20                  25                  30

Val Ile Leu Asn Leu Arg Lys Glu Gly His Glu Val Leu Asp Val Thr
         35                  40                  45

Pro Gly Asn Cys Asp Val Asn Thr Asp Leu Arg Tyr Gly Val Asn Lys
 50                  55                  60

Ala Glu Glu Trp Gly Ala Asp Leu Phe Ile Ser Ile His Phe Asp Lys
 65                  70                  75                  80

Ala Tyr Asp Ser Tyr Asn Gly Ala Leu Gly Thr Gly Thr Trp Ile Cys
                 85                  90                  95

Gly Ala Gly Gln Ala Glu Val Tyr Ala Arg Arg Ile Val Asn Ser
            100                 105                 110

Ile Ala Asn Gly Thr Gly Leu Arg Asn Arg Gly Val Lys Thr Asn Pro
        115                 120                 125

Lys Leu Tyr Glu Leu Arg Lys Thr Ser Met Pro Ala Val Ile Ile Glu
    130                 135                 140

Val Cys Phe Cys Glu Ala Thr Thr Asp Val Ser Ile Tyr Lys Ala Lys
145                 150                 155                 160

Gly Ser Asn Leu Ile Gly Glu Leu Ile Ala Glu Gly Ile Cys Asn Lys
                165                 170                 175

Asp Ile Lys Thr Asp Asn Ile Pro Ser Gln Thr Gln Ser Ser Val Ser
        180                 185                 190

Leu Asp Gly Phe Tyr Glu Ser Ser Glu Thr Arg Thr Asn Ala Thr Ile
    195                 200                 205

Val Gly Ala Gly Arg Ile Ser Val Leu Asn Lys Asn Cys Glu Pro Ile
    210                 215                 220

Pro Asn Arg Tyr Ile Asp Ser Leu Asp Arg Ile Phe Val Leu Gly Ile
225                 230                 235                 240

Tyr Pro Ser Leu Lys Phe Ile Glu Ile Val Tyr Pro Gly Ser Glu Lys
                245                 250                 255

Met Tyr His Ala Tyr Ile Asp Ile Glu Asn Tyr Asn Arg Ile Ser Phe
        260                 265                 270

Asp Tyr His Phe Gly Tyr His Asn Asp Gly Gly Asp Thr Tyr Val Trp
    275                 280                 285

Trp Asn Ser Asp Asp Val Asn Glu Lys Glu Pro Asp Glu Ile Leu Leu
290                 295                 300

Pro Asn Tyr Lys Ala Ser Pro Met Tyr Arg Thr Asn Gly Trp Leu Arg
305                 310                 315                 320

Ile Thr Phe Tyr Arg Ala Asp Gly Asn Pro Ser Asp Gly Tyr Val Arg
                325                 330                 335

Tyr Glu Gly Lys Gln Lys Glu Arg Phe Tyr Arg Ile Cys
        340                 345

<210> SEQ ID NO 18
<211> LENGTH: 419
<212> TYPE: PRT
<213> ORGANISM: Clostridium perfringens

<400> SEQUENCE: 18

Met Ser Lys Asn Ile Lys Lys Ile Ala Val Arg Gly Gly His Asn Phe
1               5                   10                  15

Gln Ala Thr Gly Ala Val Ala Leu Ile Gly Glu Thr Ser Glu Asp Arg
            20                  25                  30

Lys Val Lys Asp Ser Val Ile Val Tyr Leu Arg Gln Glu Gly Tyr Gln
        35                  40                  45
```

Val Leu Asp Val Thr Pro Gly Asn Cys Asp Gln Ile Thr Asp Leu Arg
 50                  55                  60

Tyr Gly Val Asn Lys Ala Glu Glu Trp Gly Ala Asp Leu Phe Ile Ser
 65                  70                  75                  80

Ile His Phe Asp Lys Ala Tyr Asp Ser Tyr Asn Gly Ala Leu Gly Thr
                 85                  90                  95

Gly Thr Trp Ile Tyr Gly Thr Gly Lys Ala Glu Val Tyr Ala Arg
            100                 105                 110

Arg Ile Val Asn Ser Ile Ala Ser Gly Thr Gly Leu Lys Asn Arg Gly
            115                 120                 125

Val Lys Thr Asn Ser Lys Leu Tyr Glu Leu Arg Asn Thr Ser Met Pro
130                 135                 140

Ala Val Ile Val Glu Val Cys Phe Cys Glu Ala Thr Thr Asp Val Ala
145                 150                 155                 160

Ile Tyr Lys Ala Lys Gly Pro Lys Leu Ile Gly Glu Leu Ile Ala Glu
                165                 170                 175

Gly Ile Cys Asn Lys Asp Ile His Thr Asp Asn Thr Pro Ser Leu Thr
            180                 185                 190

Pro Gln Asp Ser Val Ser Leu Asp Gly Phe Tyr Glu Ser Ser Glu Thr
            195                 200                 205

Arg Thr Asn Ala Thr Ile Val Gly Glu Gly Arg Ile Glu Val Leu Asn
210                 215                 220

Lys Asn Cys Gln Pro Ile Pro Asn Arg Tyr Ile Asp Ser Leu Asp Arg
225                 230                 235                 240

Ile Phe Val Leu Gly Ile Tyr Pro Ser Leu Lys Phe Ile Glu Val Val
                245                 250                 255

Tyr Pro Ala Ser Gly Lys Met Tyr His Ala Tyr Ile Asp Ile Glu Asn
            260                 265                 270

Tyr Asn Arg Ile Ser Phe Asp Tyr His Phe Gly Tyr His Asn Asp Gly
            275                 280                 285

Gly Asp Thr Tyr Val Trp Trp Asn Ser Asp Asp Val Asn Glu Lys Glu
290                 295                 300

Pro Asp Glu Ile Leu Leu Pro Asn Tyr Lys Ala Ser Pro Met Tyr Arg
305                 310                 315                 320

Thr Asn Gly Trp Leu Arg Ile Thr Phe Tyr Arg Ala Asp Gly Asn Pro
                325                 330                 335

Ser Asp Gly Tyr Val Arg Tyr Glu Gly Glu Gln Thr Glu Arg Phe Tyr
            340                 345                 350

Lys Lys Gly Glu Val Val Asn Val Arg Thr Ser Leu Thr Val Arg Lys
            355                 360                 365

Gly Pro Gly Thr Asn Tyr Ser Asn Ile Gly Ser Leu Glu Pro Asn Glu
370                 375                 380

Asn Val Asp Ile Leu Glu Met Ile Gly Glu Trp Tyr His Val Glu Tyr
385                 390                 395                 400

Asn Thr Asn Lys Gly Arg Lys Arg Gly Tyr Val Ser Ala Lys Tyr Ile
                405                 410                 415

Lys Glu Val

<210> SEQ ID NO 19
<211> LENGTH: 415
<212> TYPE: PRT
<213> ORGANISM: Clostridium perfringens

<400> SEQUENCE: 19

```
Met Lys Ile Ala Val Arg Gly Gly His Asn Phe Gln Ala Thr Gly Ala
1               5                   10                  15

Ala Ala Leu Ile Gly Glu Thr Ser Glu Asp Arg Lys Val Lys Asp Ser
                20                  25                  30

Val Ile Glu Cys Leu Arg Gln Glu Gly His Gln Val Leu Asp Val Thr
            35                  40                  45

Pro Gly Asn Cys Asp Gln Ile Thr Asp Leu Arg Tyr Gly Val Asn Lys
    50                  55                  60

Ala Glu Glu Trp Gly Ala Asp Leu Phe Ile Ser Ile His Phe Asp Lys
65              70                  75                  80

Ala Tyr Asp Ser Tyr Asn Gly Ala Leu Gly Thr Gly Thr Trp Ile Tyr
                85                  90                  95

Gly Thr Gly Gly Lys Ala Glu Val Tyr Ala Arg Arg Ile Val Asn Ser
            100                 105                 110

Ile Ala Asn Gly Thr Gly Leu Lys Asn Arg Gly Val Lys Thr Asn Ser
        115                 120                 125

Lys Leu Tyr Glu Leu Arg Asn Thr Ser Met Pro Ala Val Ile Val Glu
    130                 135                 140

Val Cys Phe Cys Glu Ala Thr Thr Asp Val Ala Ile Tyr Lys Ser Lys
145                 150                 155                 160

Gly Pro Lys Leu Ile Gly Glu Leu Ile Ala Glu Gly Ile Cys Asn Lys
                165                 170                 175

Asp Ile Ser Ser Asp Asn Thr Thr Asn Gln Thr Glu Gln Pro Ser Val
            180                 185                 190

Ser Leu Glu Gly Phe Tyr Glu Ser Glu Thr Arg Thr Asn Ala Thr
        195                 200                 205

Ile Val Gly Lys Gly Arg Ile Ala Val Leu Asn Lys Asn Cys Gln Pro
    210                 215                 220

Ile Pro Asp Arg Tyr Ile Asp Ser Leu Asp Arg Ile Phe Val Leu Gly
225                 230                 235                 240

Ile Tyr Pro Ser Leu Lys Phe Ile Glu Val Val Tyr Pro Ala Ser Gly
                245                 250                 255

Lys Met Tyr His Ala Tyr Ile Asp Ile Glu Asn Tyr Asn Arg Val Ser
            260                 265                 270

Phe Asp Tyr His Phe Gly Tyr His Asn Asp Asn Gly Asp Thr Tyr Val
        275                 280                 285

Trp Trp Asn Ser Asp Asp Val Ser Glu Lys Glu Pro Asp Glu Ile Leu
    290                 295                 300

Leu Pro Asn Tyr Lys Ala Ser Pro Met Tyr Arg Thr Asn Gly Trp Leu
305                 310                 315                 320

Arg Val Thr Phe Tyr Arg Ala Asp Gly Asn Pro Ser Asp Gly Tyr Val
                325                 330                 335

Arg Tyr Glu Gly Glu Gln Lys Glu Arg Phe Tyr Lys Lys Gly Lys Val
            340                 345                 350

Val Asn Val Arg Thr Ser Leu Thr Val Arg Lys Gly Pro Gly Thr Asn
        355                 360                 365

Tyr Ser Asn Ile Gly Ser Leu Glu Pro Asn Glu Lys Val Asp Ile Leu
    370                 375                 380

Glu Lys Val Glu Gly Trp Tyr Tyr Ile Glu Tyr Asn Ala Arg Asn Glu
385                 390                 395                 400

Arg Lys Arg Gly Tyr Val Ser Glu Lys Tyr Ile Glu Ile Ile Gln
                405                 410                 415
```